(12) United States Patent
Weiss et al.

(10) Patent No.: US 12,297,506 B2
(45) Date of Patent: May 13, 2025

(54) HIGH PERFORMANCE MULTI-INPUT MICRORNA SENSORS AND USES THEREOF

(71) Applicant: Massachusetts Institute of Technology, Cambridge, MA (US)

(72) Inventors: Ron Weiss, Newton, MA (US); Jin Huh, Watertown, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 392 days.

(21) Appl. No.: 17/688,985

(22) Filed: Mar. 8, 2022

(65) Prior Publication Data
US 2022/0282334 A1     Sep. 8, 2022

Related U.S. Application Data

(63) Continuation of application No. 15/665,156, filed on Jul. 31, 2017, now Pat. No. 11,359,247.

(51) Int. Cl.
| | |
|---|---|
| C12Q 1/6886 | (2018.01) |
| A61K 31/7125 | (2006.01) |
| C12N 15/113 | (2010.01) |
| C12Q 1/6811 | (2018.01) |
| C12Q 1/6897 | (2018.01) |

(52) U.S. Cl.
CPC ........ *C12Q 1/6886* (2013.01); *A61K 31/7125* (2013.01); *C12N 15/113* (2013.01); *C12Q 1/6811* (2013.01); *C12Q 1/6897* (2013.01); *C12N 2310/14* (2013.01); *C12Q 2525/204* (2013.01); *C12Q 2525/207* (2013.01); *C12Q 2600/136* (2013.01); *C12Q 2600/178* (2013.01)

(58) Field of Classification Search
None
See application file for complete search history.

(56) References Cited

U.S. PATENT DOCUMENTS

| | | |
|---|---|---|
| 9,458,509 B2 | 10/2016 | Benenson et al. |
| 11,339,395 B2 * | 5/2022 | Weiss ............. C12N 15/85 |
| 11,359,247 B2 * | 6/2022 | Weiss ............. C12N 15/113 |
| 2013/0009799 A1 | 1/2013 | Collins et al. |
| 2013/0202532 A1 | 8/2013 | Benenson et al. |
| 2017/0145426 A1 | 5/2017 | Xie et al. |
| 2019/0032141 A1 | 1/2019 | Weiss et al. |

FOREIGN PATENT DOCUMENTS

| | | |
|---|---|---|
| WO | WO 2015/165275 A1 | 11/2015 |
| WO | WO 2016/040395 A1 | 3/2016 |

OTHER PUBLICATIONS

Engineering a regulatory framework for synthetic self-amplifying RNA circuits, retrieved on-line https://hdl.handle.net/2144/23683, Boston University, pp. 1-133, Tyler Wagner dissertation (Year: 2017).*
Yeh et al. ACS Chem Biol. 14, 959-965 (Year: 2019).*
Lapique et al., Digital switching in a biosensor circuit via programmable timing of gene availability. Nat Chem Biol. Dec. 2014; 10(12):1020-7. doi: 10.1038/nchembio.1680. Epub Oct. 14, 2014. Supplemental Material, 3 pages.
Mazumder et al., Design and characterization of a dual-mode promoter with activation and repression capability for tuning gene expression in yeast. Nucleic Acids Res. Aug. 2014;42(14):9514-22. doi: 10.1093/nar/gku651. Epub Jul. 23, 2014.
Mohammadi et al., Automated Design of Synthetic Cell Classifier Circuits Using a Two-Step Optimization Strategy. Cell Syst. Feb. 22, 2017;4(2):207-218.e14. doi: 10.1016/j.cels.2017.01.003. Epub Feb. 8, 2017.
Schreiber et al., Model-guided combinatorial optimization of complex synthetic gene networks. Mol Syst Biol. Dec. 28, 2016;12(12):899(1-14). doi: 10.15252/msb.20167265.
Wroblewska et al., Mammalian synthetic circuits with RNA binding proteins for RNA-only delivery. Nat Biotechnol. Aug. 2015;33(8):839-41. doi: 10.1038/nbt.3301. Epub Aug. 3, 2015.
Xie et al., Multi-input RNAi-based logic circuit for identification of specific cancer cells. Science. Sep. 2, 2011;333(6047):1307-11. doi: 10.1126/science.1205527.

* cited by examiner

*Primary Examiner* — Brian Whiteman
(74) *Attorney, Agent, or Firm* — Wolf, Greenfield & Sacks, P.C.

(57) ABSTRACT

Provided herein are genetic circuits and cell state classifiers for detecting the microRNA profile of a cell. The cell state classifiers of the present disclosure are designed to incorporate multiple genetic circuits integrated together by transcriptional or translational control. Multiple inputs can be sensed simultaneously by coupling their detection to different portions of the genetic circuit such that the output molecule is produced only when the correct input profile of miRNAs is detected. The genetic circuits and cell state classifiers may be used in various applications (e.g., therapeutic or diagnostic applications).

17 Claims, 46 Drawing Sheets

Specification includes a Sequence Listing.

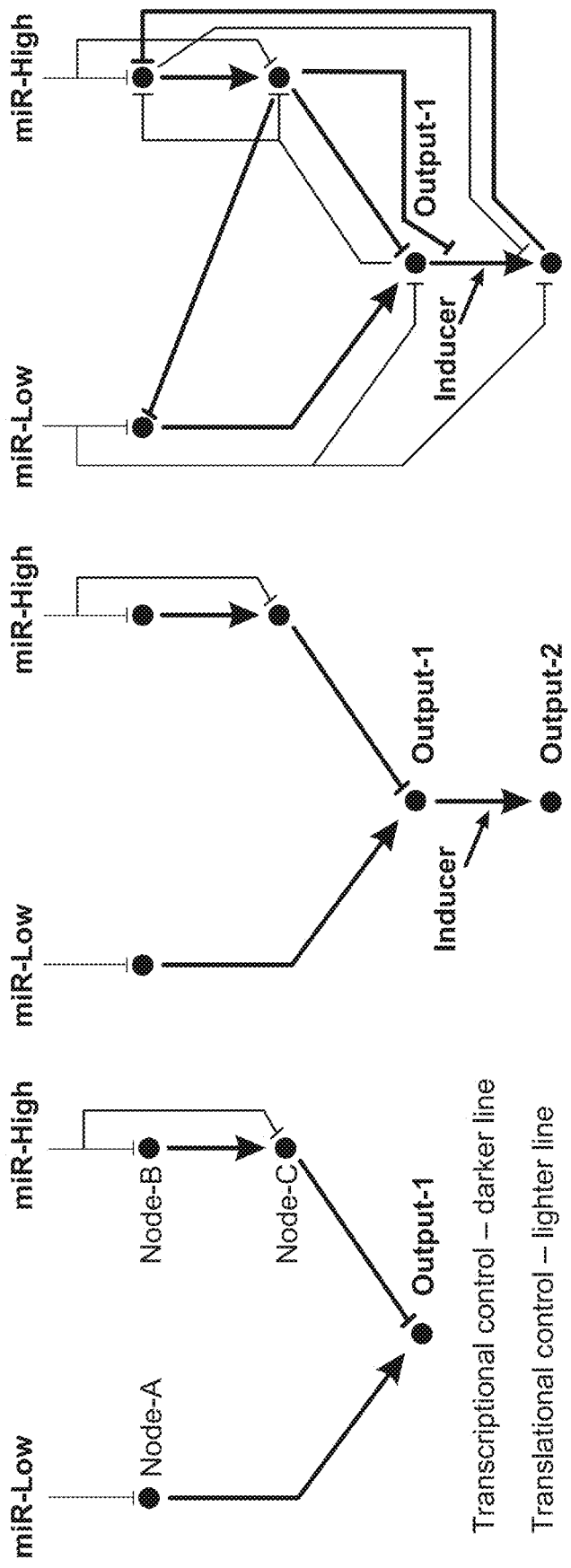

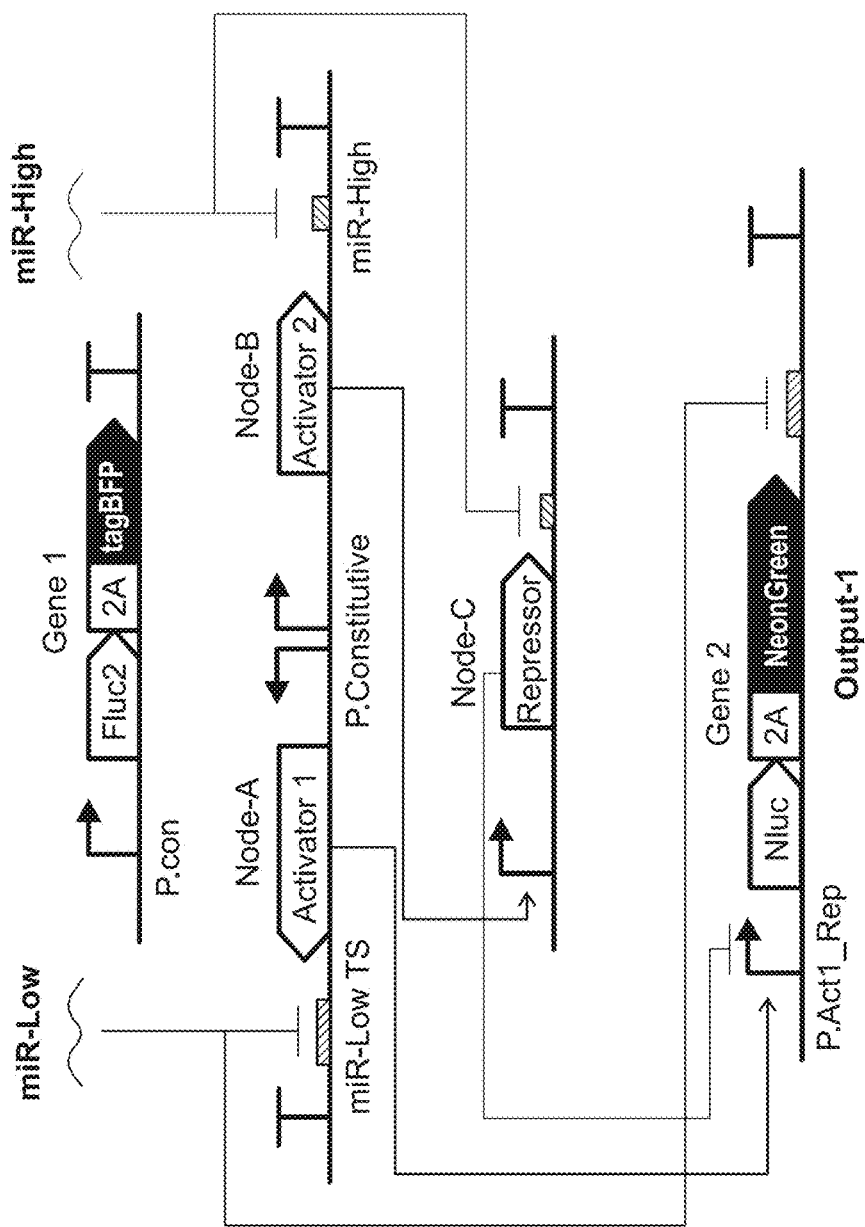
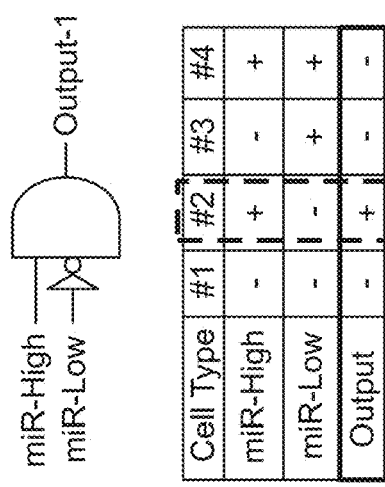
FIG. 2B
FIG. 2A

HIGH PERFORMANCE MULTI-INPUT MICRORNA SENSORS AND USES THEREOF

RELATED APPLICATION

This application is a continuation of U.S. patent application Ser. No. 15/665,156, filed Jul. 31, 2017, the entire contents of which are incorporated by reference herein.

GOVERNMENT SUPPORT

This invention was made with government support under R01 CA173712 and P50 GM098792 awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Mar. 7, 2022, is named M065670413US01-SEQ-NTJ and is 2,143 bytes in size.

BACKGROUND

The microRNA (miRNA) profile of each cell type varies and may serve as cellular input for a genetic circuit designed to detect the cell type of interest. The genetic circuit may also be designed such that an output molecule is expressed when a matching miRNA profile is detected. The sensitivity and specificity of the generic circuit to the input influences its performance. For therapeutic use of such genetic circuit, high performance circuits are desired.

SUMMARY

Provided herein are genetic circuits and cell state classifiers for detecting the microRNA profile of a cell, and methods of using such circuits and systems in various applications (e.g., therapeutic or diagnostic applications). The cell state classifiers of the present disclosure are designed to incorporate multiple genetic circuits integrated together by transcriptional or translational control. The microRNA profile of a certain cell is detected via engineered downregulation of the expression of an output molecule by these miRNAs (e.g., by incorporating target sites of the microRNA to be detected into genetic circuits that control the expression of the output molecule). Multiple inputs can be sensed simultaneously by coupling their detection to different portions of the genetic circuit such that the output molecule is produced only when the correct input profile of miRNAs is detected. In some embodiments, the genetic circuits described herein are used for the detection of a diseased cell (e.g., a cancer cell). In some embodiments, detection of the diseased cell (e.g., the cancer cell) is coupled with the expression of a detectable output molecule (e.g., a fluorescent protein) for diagnosing a disease (e.g., cancer). In some embodiments, detection of the diseased cell (e.g., a cancer cell) is coupled with the expression of a therapeutic molecule for treating a disease (e.g., cancer).

Accordingly, some aspects of the present disclosure provide cell state classifiers containing: (i) a first sensor circuit containing a promoter operably linked to a nucleotide sequence encoding a first activator and one or more target sites for a first set of microRNAs; (ii) a second sensor circuit containing: (a) a promoter operably linked to a nucleotide sequence encoding a second activator and one or more target sites for a second microRNA; (b) a promoter that is activated by the second activator of (ii)(a), operably linked to a nucleotide sequence encoding a first repressor and one or more target sites for the second microRNA of (ii)(a); wherein the second activator is different from the first activator, and (iii) a first signal circuit containing a first activatable/repressible promoter that is activated by the first activator of (i) or repressed by the first repressor of (iii), operably linked to a nucleotide sequence encoding a first output molecule and one or more target sites for any one of the first set of microRNAs of (i). In some embodiments, the cell state classifier contains a plurality of the second sensor circuit of (ii).

In some embodiments, the first signal circuit of (iii) further contains a nucleotide sequence encoding a third activator, operably linked to the first activatable/repressible promoter of (iii). In some embodiments, the cell state classifier further contains a second signal circuit containing a promoter that is activated by the third activator in the presence of an inducer, operably linked to a nucleotide sequence encoding a second output molecule. In some embodiments, the first signal sensor circuit of (iii) further contains a nucleotide sequence encoding a first regulatory microRNA, operably linked to the first activatable/repressible promoter of (iii) that is different from any of the first set of microRNAs or the second microRNA.

In some embodiments, (ii)(a) of the second sensor circuit further contains one or more target sites for the first regulatory microRNA. In some embodiments, the one or more target sites for the first regulatory microRNA is upstream and/or downstream of the nucleotide sequence encoding the second activator.

In some embodiments, (ii)(b) of the second sensor circuit further contains one or more target sites for the first regulatory microRNA. In some embodiments, the one or more target sites for the first regulatory microRNA is upstream and/or downstream of the nucleotide sequence encoding the first repressor.

In some embodiments, (ii)(a) of the second sensor circuit further contains a nucleotide sequence encoding a second regulatory microRNA operably linked to the promoter of (ii)(a), wherein the second regulatory microRNA is not the same as any of the first set of microRNAs, the second microRNA, or the first regulatory microRNA. In some embodiments, the second signal circuit further contains one or more target sites for the second regulatory microRNA.

In some embodiments, (ii)(a) of the second sensor circuit further contains multiple target sites for the second microRNA. In some embodiments, the multiple target sites for the second microRNA are upstream and/or downstream of the nucleotide sequence encoding the second activator.

In some embodiments, (ii)(b) of the second sensor circuit further contains multiple target sites for the second microRNA upstream of the nucleotide sequence encoding the first repressor. In some embodiments, the multiple target sites for the second microRNA is upstream and/or downstream of the nucleotide sequence encoding the first repressor.

In some embodiments, the cell state classifier described herein further contains a regulatory circuit containing a second activatable/repressible promoter that is activated by the third activator in the presence of an inducer and repressed by the first repressor, operably linked to a nucleotide encoding a second repressor and one or more target sites for the first set of microRNAs of (i). In some embodiments, the second repressor represses the promoter of (ii)(a). In some embodiments, the second signal circuit further contains one or more target sites for any one of the first set of microRNAs. In some embodiments, the promoter of the second signal circuit is a second activatable/repressible promoter that is activated by the third activator in the presence of an inducer and repressed by the first repressor. In some embodiments, the first repressor represses the promoter of (i).

In some embodiments, the cell state classifier described herein further contains a control circuit that contains a constitutive promoter operably linked to a nucleotide sequence encoding a control signal that is different from the first output molecule or the second output molecule.

In some embodiments, the first output molecule is a detectable molecule. In some embodiments, the second output molecule is a detectable molecule. In some embodiments, the detectable molecule is a protein or a RNA. In some embodiments, the protein is a fluorescent protein or an enzyme. In some embodiments, the protein is a fluorescent RNA.

In some embodiments, the first output molecule is a therapeutic molecule. In some embodiments, the second output molecule is a therapeutic molecule. In some embodiments, the therapeutic molecule is for treating cancer.

In some embodiments, the first activator is VP16GAL4. In some embodiments, the second activator is tTA. In some embodiments, the first repressor is BM3R1. In some embodiments, the second repressor is LmrA. In some embodiments, the first regulatory microRNA is miR-FF5. In some embodiments, the second regulatory microRNA is miR-FF3. In some embodiments, the second activatable/repressible promoter is pPhIF. In some embodiments, the first activatable/repressible promoter of (iii) is pUAS_BM3E1.

In some embodiments, the first sensor circuit, (ii)(a) of the second sensor circuit, (ii)(b) of the second circuit, and/or the first signal circuit further contains an insulator, an enhancer, one or more operators, a nucleotide sequence encoding one or more output molecules operably linked to the promoter of (i), (ii)(a), (ii)(b), and/or (iii), a nucleotide sequence encoding a microRNA, and/or a polyadenylation signal.

In some embodiments, the second signal circuit further contains an insulator, an enhancer, one or more operators, a nucleotide sequence encoding one or more output molecules operably linked to the promoter of the second signal circuit, a nucleotide sequence encoding a microRNA, and/or a polyadenylation signal.

In some embodiments, the regulatory circuit further contains an insulator, an enhancer, one or more operators, a nucleotide sequence encoding one or more output molecules operably linked to the promoter of the regulator circuit, a nucleotide sequence encoding a microRNA, and/or a polyadenylation signal.

In some embodiments, the control circuit further contains an insulator, an enhancer, one or more operators, a nucleotide sequence encoding one or more output molecules operably linked to the promoter of the control circuit, a nucleotide sequence encoding a microRNA, and/or a polyadenylation signal.

Other aspects of the present disclosure provide libraries of cell state classifiers described herein.

Cells containing the cell state classifiers described herein are also provided. In some embodiments, the cell is a prokaryotic cell. In some embodiments, the cell is a bacterial cell. In some embodiments, the cell is a eukaryotic cell. In some embodiments, the eukaryotic cell is a plant cell, an insect cell, or a mammalian cell. In some embodiments, the cell is a human cell. In some embodiments, the cell is a diseased cell. In some embodiments, the cell is a cancer cell.

In some embodiments, the cell does not express any one of the first set of microRNAs. In some embodiments, the cell expresses the second microRNA. In some embodiments, the cell expresses at least one of the first set of microRNAs and does not express the second microRNA. In some embodiments, the cell expresses at least one of the first set of microRNAs and expresses the second microRNA. In some embodiments, the cell does not express any one of the first set of microRNAs and does not express the second microRNA.

In another aspect, methods for designing and producing improved cell state classifiers and circuits are provided. In some embodiments, the rules stated in the descriptions of FIGS. 11A-11B to FIGS. 22A-22B can be used to design modifications of the cell state classifiers and circuits described herein. Using the rules described herein, one can design and test cell state classifiers and circuits having the same function but having increased performance. The rules to be applied include: additions of coherent feed-forward loop(s), replacing endogenous activation with synthetic activation, increasing performance by addition of miRNA repression sites on same target, addition of feedback loop(s), and/or addition of several connections at once to create a new node to replicate or replace some or all of the regulation of another node. In some instances, the higher performance is obtained via additions of redundant functions of the parts of the cell state classifiers and circuits. The improvements in cell state classifiers and circuits can be increased performance of the cell state classifiers and circuits, while keeping the same logic of the cell state classifiers and circuits. Improvements in performance include improvements in therapeutic index, specificity, ON/OFF, robustness, and resistance to mutation.

Other aspects of the present disclosure provide methods containing maintaining the cells described herein. In some embodiments, the method further contains detecting the first output molecule. In some embodiments, the method further contains providing the cell with the inducer and detecting the second output molecule. In some embodiments, the method further contains classifying the cell.

Other aspects of the present disclosure relate to methods containing delivering the cell state classifier described herein to a cell and detecting an output molecule.

Other aspects of the present disclosure provide methods of treating a disease or disorder, the method containing delivering the cell state classifier described herein to a cell, wherein the output molecule is a therapeutic molecule that treats the disease or disorder. In some embodiments, the cell is a diseased cell. In some embodiments, the cell is a cancer cell.

Other aspects of the present disclosure provide methods of diagnosing a disease or disorder, the method containing delivering the cell state classifier described herein to a cell. In some embodiments, the cell is a diseased cell. In some embodiments, the cell is a cancer cell. In some embodiments, the method further contains detecting a first output molecule. In some embodiments, the method further contains providing the cell with an inducer. In some embodiments, the method further containing detecting a second output molecule. In some embodiments, the expression of the first output molecule indicates the disease or disorder. In some embodiments, the lack of expression of the first output molecule indicates the disease or disorder. In some embodiments, the expression of the second output molecule indicates the disease or disorder. In some embodiments, the lack of expression of the second output molecule indicates the disease or disorder.

Other aspects of the present disclosure provide methods of treating a disease or disorder, containing administering an effective amount of a composition containing the cell state classifier described herein to a subject in need thereof, wherein the output molecule is a therapeutic molecule that treats the disease or disorder. Other aspects of the present disclosure provide methods of diagnosing a disease or disorder, containing administering an effective amount of a composition containing the cell state classifier described herein to a subject in need thereof. In some embodiments, the composition further contains a pharmaceutically acceptable carrier.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. For purposes of clarity, not every component may be labeled in every drawing.

FIGS. 1A-1C: Simplified classifier schematics. In the schematics, "nodes" represent transcriptional units that are regulated by transcription factors (activators and repressors) and microRNA (either endogenous or synthetic). "miR-Low" or "miR-High" represents endogenous microRNAs. Synthetic microRNAs are depicted as orange line coming out of nodes. miR-Low can be one or more microRNAs that all must be low in order for the output to be high. miR-High is a single microRNA that must be high in order for the output to be high. It is possible to require that multiple microRNAs be high by duplicating the miR-High branch (not depicted here). (FIG. 1A) Simplest topology of a multi-input microRNA classifier with one output. Node-A activates Output-1 (this activation is required). miR-Low degrades transcripts of Node A. An alternate "simplest" design is one where miR-Low degrades Output-1. Node-B activates Node-C, and Node-C represses Output-1. miR-High degrades transcripts of both Node-B and Node-C. Incorporation of Node-A creates a delay in the possible transcription of Output-1 following introduction of the circuit into a cell. This delay improves performance of the circuit following introduction of the circuit, especially in situations where miR-Low is low and miR-High is also low (and hence the output should be low too). In this case, it takes Node-B some time to be expressed and activate Node-C, which in turn represses Output-1. Thus, the delay in Node-A levels increasing to a level enough to activate Output-1 reduces the undesirable initial expression of Output-1. The additional redundant links (e.g., miR-Low repressing both Node-A and Output-1, miR-High repressing both Node-B and Node-C, and Node-B activating Output-1 indirectly thru Node-C and instead of direct activation) improve the ON/OFF performance of the circuit. (FIG. 1B) Topology of a two-step cell classifier. Output-2 is added to the classifier described in Panel A. Output-2 is activated only in the presence of both Output-1 and an external inducer. This topology allows multi-step gene activation where Output-1 is first expressed (only in the cell types of interest), and then the inducer is added to activate Output-2. As with the circuit in Panel A, miR-Low can alternatively repress Output-1 instead of Node-A in this simple design. (FIG. 1C) A robust two-step cell classifier. Redundant features provide enhanced performance and robustness. Feed-forward and feedback motifs are added to improve the ON or OFF states of Output-1 and Output-2. The additional features include the following: miR-Low now represses Output-2. Node-C represses Node-A. Output-1 node represses Node-B and Node-C. Node-B represses Output-2. Output-2 represses Node-B.

FIGS. 2A-2B: Diagram of a genetic circuit implementing the simplest classifier circuit. A more detailed description of the cell classifier from FIG. 1A is provided with specific transcriptional units. (FIG. 2A) A logic circuit and truth table depicting logic gates applicable to the cell state classifier described herein. Output molecule should be high when miR-Low is low and miR-High is high. The logic circuit depicts a NOT gate connected to an AND gate. (FIG. 2B) Directional elbow arrows show promoters, followed by genes, microRNA target sites, and terminators ("T"). 2A tags are used to transcriptionally link genes, which are translated together but are then spliced. Gene 1 and Gene 2 show the two fluorescent proteins expressed by the circuit. Gene 1, at the top of the diagram, constitutively expresses Fluc2 and tagBFP for bioluminescence and fluorescence respectively, and is used as the transfection marker. Activator 1, Activator 2, Repressor, and Nluc-2A-NeonGreen represent Node-A, Node-B, Node-C, and Output-1, respectively. Output-1 is only produced in Cell Type #2 (from the truth table in FIG. 2A) when miR-High is present and miR-Low is absent. Output-1 is regulated by a promoter that is both activated by Activator 1 and repressed by Repressor. Expression of Repressor is activated by Activator 2. MiR-Low target sites are incorporated at 3' UTR of both Activator 1 and Output-1. MiR-High target sites are incorporated at the 3' UTR of both Activator 2 and Repressor. In Cell Type #1, transcripts of Activator 2 and Repressor are not degraded by miR-High, and Repressor blocks expression of Output-1 and Activator 1 cannot activate Output-1. In Cell Type #2, transcripts of Activator 2 and Repressor are degraded by miR-High, and Activator 1 is free to activate Output-1. In Cell Type #3, transcripts of Activator 2 and Repressors are not degraded by miR-High, and Repressor blocks expression of Output-1. At the same time, Activator 1 and Output-1 transcripts are degraded by miR-Low. In Cell Type #4, transcripts of Activator 2 and Repressor are degraded by miR-High, and repressor cannot block expression of Output-1, but transcripts of Activator 1 and Output-1 are also degraded by miR-Low and cannot activate expression of Output-1.

(FIG. 6A) An example of a non-functional circuit variant, where there is no significant difference for circuit output between HEK293 and Vero22 cells. (FIG. 6B) An example of a highly functional circuit, showing >100 difference between circuit output when transfected in HEK293 and Vero22 cells, especially for highly transfected cells. (FIG. 6C) Nine other circuit behaviors are displayed below, with various ON/OFF performances.

(FIG. 7A) The signal intensity of Output-1 (Gene 2) was measured as a function of Gene 1 (on the X axis, serving here as transfection marker). As desired, Output-1 expression in Vero22 is higher than in HEK293. The addition of ABA results in some reduction of Output-1 expression in Vero22, possibly due to resource sharing that is now required to activate expression of Output-2 (Gene 3). (FIG. 7B) The signal intensity of Output-2 (Gene 3) was measured as a function of Gene 1 (serving as the transfection marker). As desired, addition of ABA resulted in a significant increase in Output-2 expression in Vero22 cells but not in HEK293 cells.

(FIG. 11A) A Coherent Feed-Forward Loop #1 is added to circuit 0. If X⊣Z, can add repression through an intermediate activator node: X⊣Y→Z. (FIG. 11B) An example of circuit 1. Certain elements shown, e.g. VP16GAL4, are not yet included in circuit logic. They are included in the DNA, but are not yet connected downstream. Hereafter, "⊣" indicates inhibition. "→" indicates activation.

(FIG. 12A) Endogenous activation is replaced with synthetic activation. If X is activated by endogenous promoter, it can be replaced with a synthetic activator such that Y: Y→X. (FIG. 12B) An example of circuit 2.

(FIG. 13A) A coherent Feed-Forward Loop #2 is then added to circuit 2. If X⊣Y→Z, can add direct repression from X to Z such that X⊣Z. (FIG. 13B) An example of circuit 3.

(FIG. 14A) A coherent Feed-Forward Loop #1 is then added to circuit 3. If X⊣Z, repression can be added through an intermediate activator node such that X⊣Y→Z. (FIG. 14B) An example of circuit 4.

(FIG. 15A) A coherent Feed-Forward Loop #2 is then added to circuit 4. If X⊣Y→Z, direct repression can be added from X to Z such that X⊣Z. (FIG. 15B) An example of circuit 5.

(FIG. 16A) A coherent Feed-Forward Loop #1 is then added to circuit 5. If X⊣Z, repression can be through an intermediate activator node such that X⊣Y→Z. (FIG. 16B) An example of circuit 6.

(FIG. 17A) Optimization of performance via the addition of miRNA repression sites on same target to circuit 6. This does not change logic circuit. (FIG. 17B) An example of circuit 7.

(FIG. 18A) Feedback Loop #1 is then added to circuit 7. If X⊣Y, then Y repression of X can be added such that Y⊣X. (FIG. 18B) An example of circuit 8.

(FIG. 19A) Feedback Loop #2 is then added to circuit 8. If X⊣Y, then Y repression of X can be added through an intermediate activator Z such that Y⊣Z→X. (FIG. 19B) An example of circuit 9.

(FIG. 20A) A coherent Feed-Forward Loop #3 is then added to circuit 9. If X→Y⊣Z, direct repression of X on Z can be added such that X⊣Z (Note that X→Y is transcriptional control with transcriptional factors, and X⊣Z is translational control with miRNA). (FIG. 20B) An example of circuit 10.

(FIG. 21A) The addition of several connections to circuit 10 at once creates Node F, which represses Node B, replicating most of the regulation of node E. (FIG. 21B) An example of circuit 11.

(FIG. 22A) A coherent Feed-Forward Loop #3 is then added to circuit 11. If X→Y⊣Z, direct repression of X on Z can be added such that X⊣Z (Note that X→Y is transcriptional control with transcriptional factors and X⊣Z is translational control with miRNA). (FIG. 22B) An example of circuit 12.

* In FIGS. 9-22B, black circle with a letter (e.g., A, B, etc.) indicates a gene product (e.g., an activator, a repressor, or an output molecule), "♥" indicates "OR," "♥" indicates "OR/NOT,"⇢ indicates activation; and ⇠ indicates inhibition; bolded lines indicate additional regulatory circuits that was added based on the previous design; crossing of two lines does not mean connection.

(FIG. 24A) Cell classification with multiple biomarkers. Multiple biomarkers are sometimes needed as a single biomarker may not be sufficient to identify a single cell type from many others. A cell may be classified as cancer cell type X by the cell state classifier if "(A & B) are HIGH". A logic gate may be integrated into the cell state classifier such that the cell state classifier identifies a cell as cancer cell type X and X' if "(A & B) are HIGH" OR "(E & B) are HIGH". (FIGS. 24B-24D) A bio-computer to distinguish cancer cells (Hela) versus non-cancer cells.

DETAILED DESCRIPTION OF CERTAIN EMBODIMENTS

Described herein are cell state classifiers that can detect the microRNA profile of a cell and classify the cell accordingly. A "cell state classifier," as used herein, refers to a system with multiple genetic circuits integrated together by transcriptional or translational control, which is able to sense a microRNA profile (e.g., one or more microRNAs) in a cell and produce an output molecule (e.g., a detectable molecule or a therapeutic molecule) accordingly. A "microRNA profile," as used herein, refers to the expression levels of one or more microRNAs in a cell or a cell type. The microRNA profile may contain expression levels of microRNAs that have no expression or lower expression (e.g., at least 30% lower), and/or expression levels of microRNAs that express or have higher expression (e.g., at least 30% higher) in a cell or a cell type, compared to another cell or a different cell type, respectively. MicroRNAs that have no expression or lower expression is referred to herein as "microRNA-low" or "miR-low," while microRNAs that express or have high expression is referred to herein as "microRNA-high" or "miR-high."

In part, the cell state classifier of the present disclosure is designed to detect miRNA by incorporating target sites of the miRNA to be detected into different genetic circuits (e.g., sensor circuit and/or signal circuit). Expression of the microRNA leads to the degradation of mRNAs encoding the molecules that are produced by these circuits (e.g., activators, repressors, or output molecules), thus leading to different signal output by the cell state classifier, which may be detected and used for classifying the cell.

Multiple inputs (e.g., microRNAs) can be sensed simultaneously by coupling their detection to different portions of the genetic circuit such that the output molecule is produced only when the correct input profile of miRNAs is detected. The cell state classifier may be used in various applications. In some embodiments, the genetic circuits described herein may be used for the detection of a diseased cell (e.g., a cancer cell). In some embodiments, detection of the diseased cell (e.g., the cancer cell) may be achieved via the expression of a detectable output molecule (e.g., a fluorescent protein) upon detection of a matching microRNA profile. As such, the cell state classifier of the present disclosure may be used for diagnosing a disease (e.g., cancer). In some embodiments, detection of the diseased cell (e.g., a cancer cell) may be coupled with the expression of a therapeutic molecule for treating a disease (e.g., cancer). Further, to evaluate the performance of the cell state classifiers described herein, a large combinatorial library of circuit variants are generated and the performance of each circuit variant may be evaluated in living cell assays.

Figure 9:
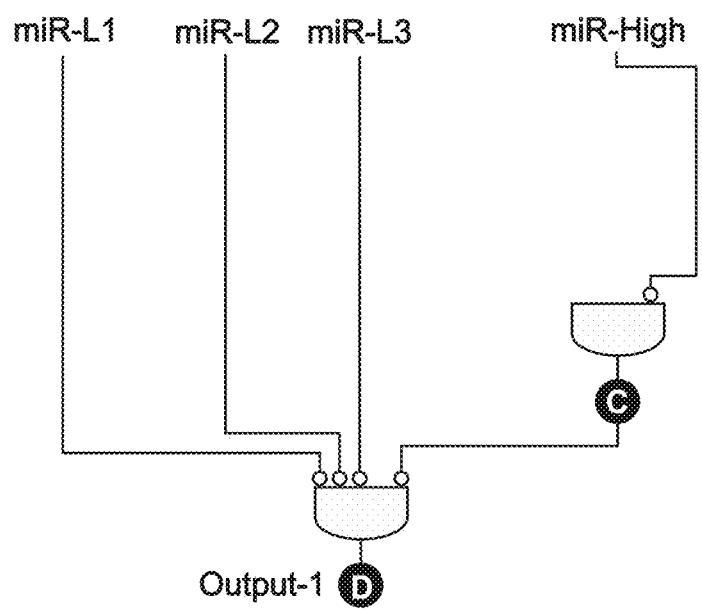
FIG. 9: Schematic of a "minimal" cell state classifier circuit.
Figure 10:
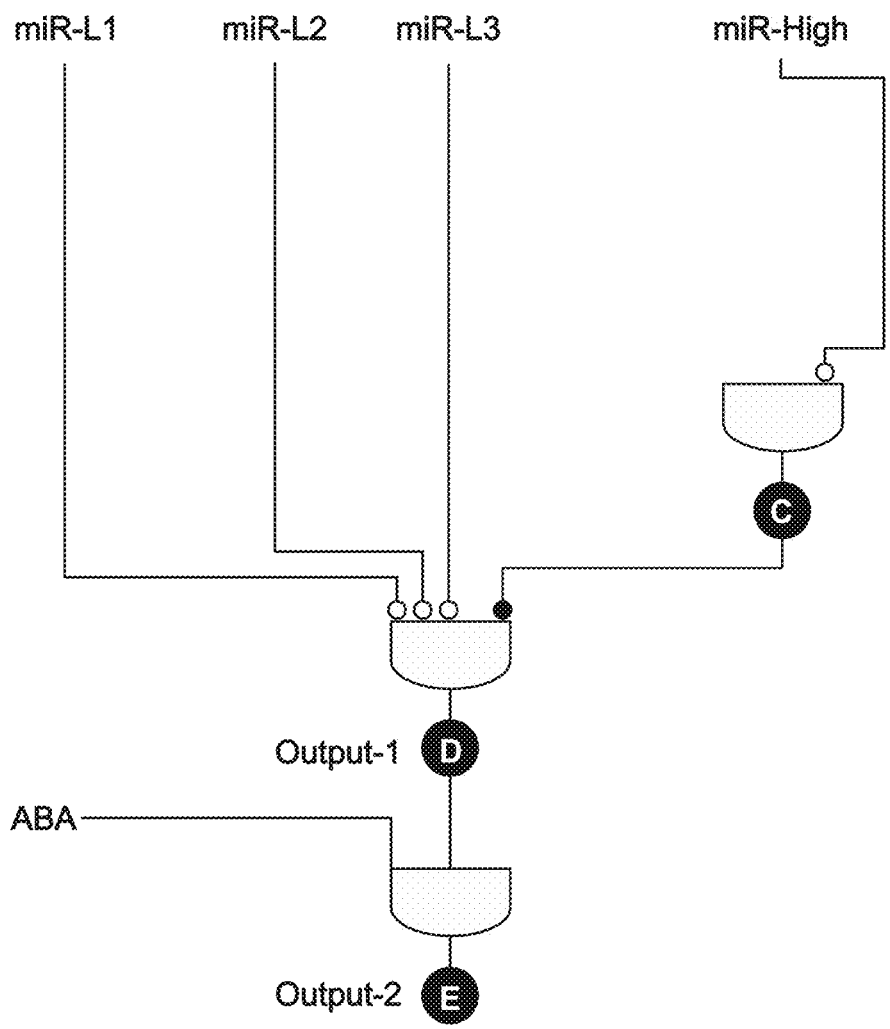
FIG. 10: Schematic of Circuit 0. A "Minimal" cell classifier with 2 output molecules.
Figure 11A:
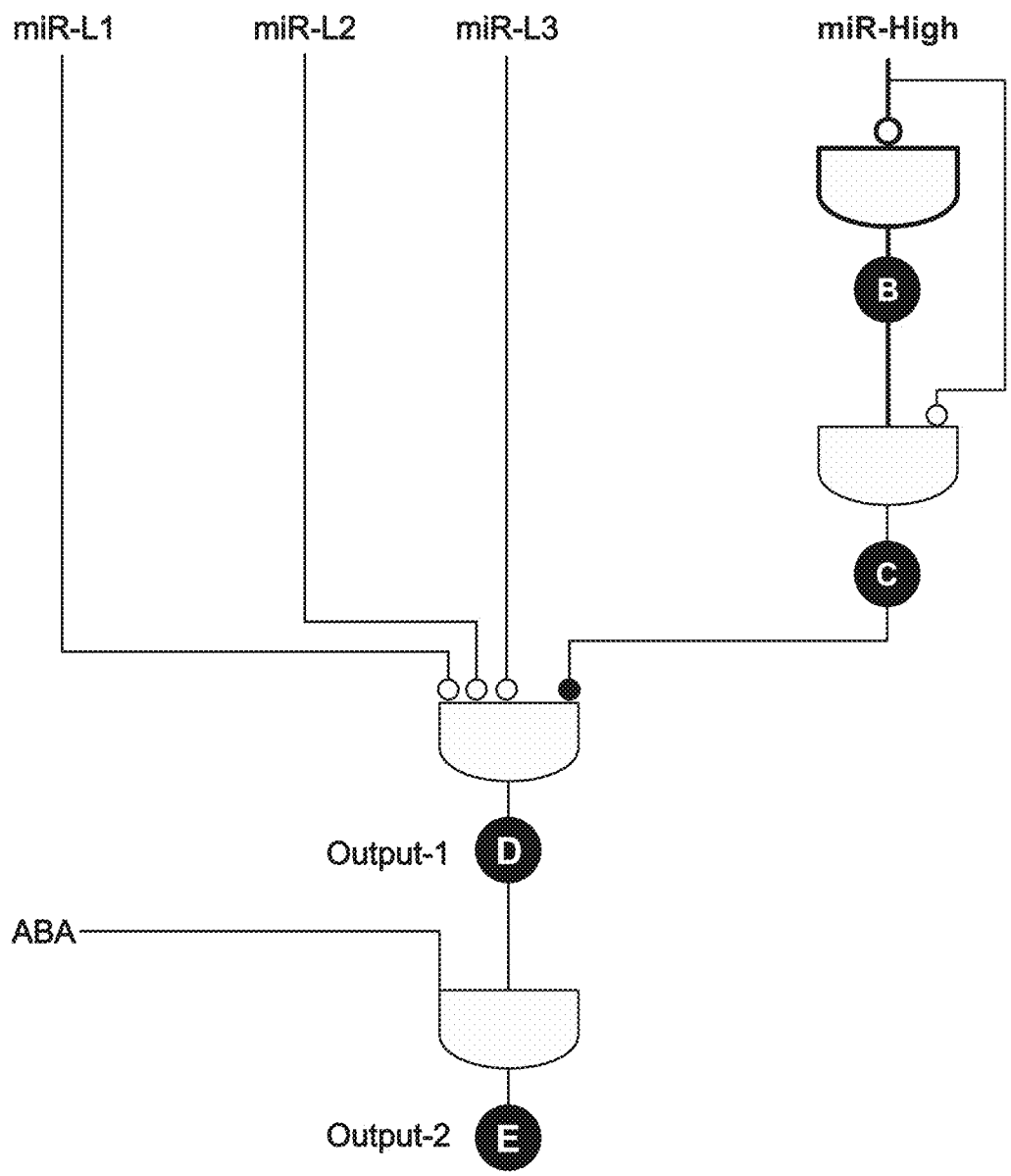
FIGS. 11A-11B: Schematics of Circuit 1.
Figure 11B:
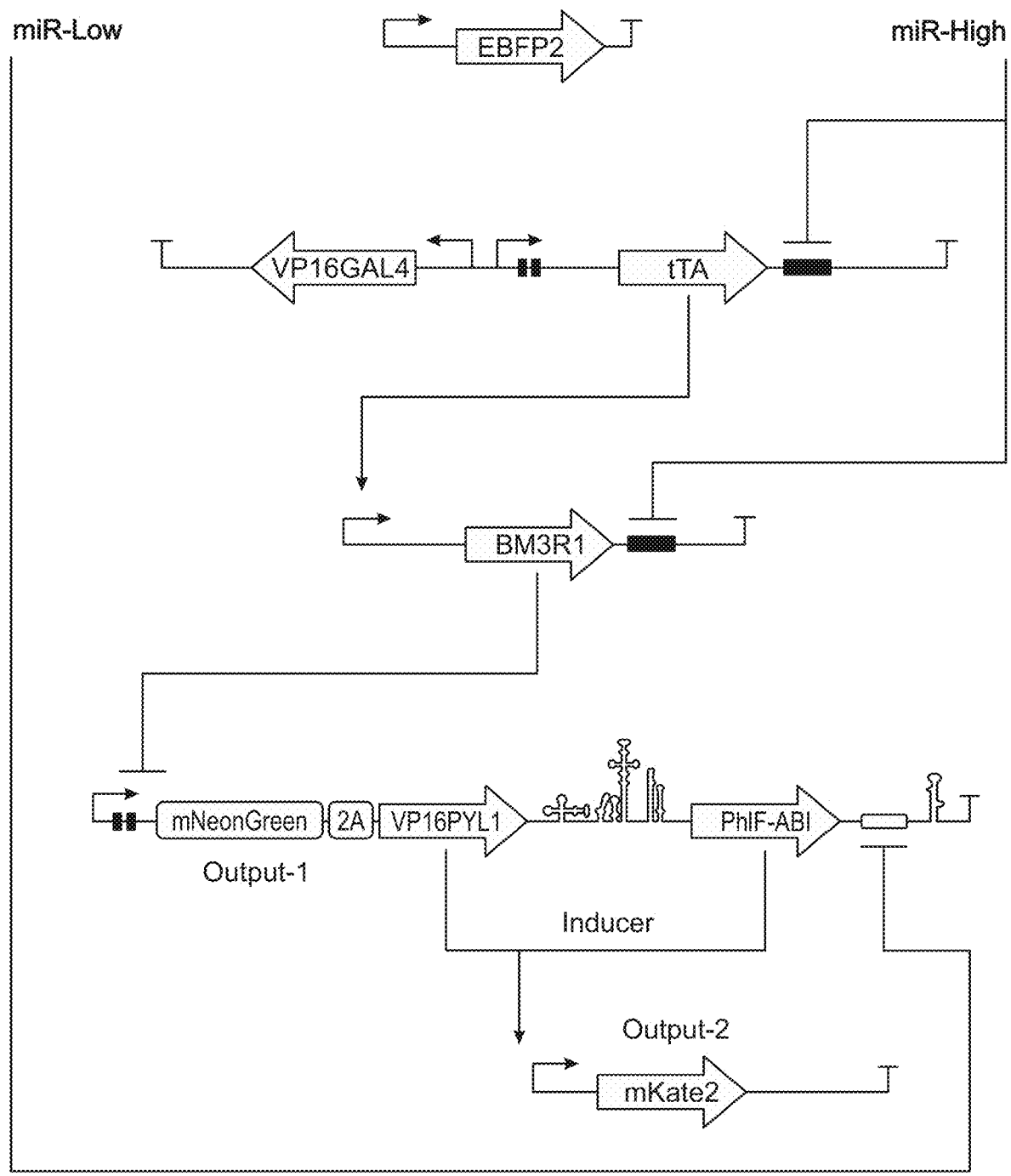
Figure 12A:
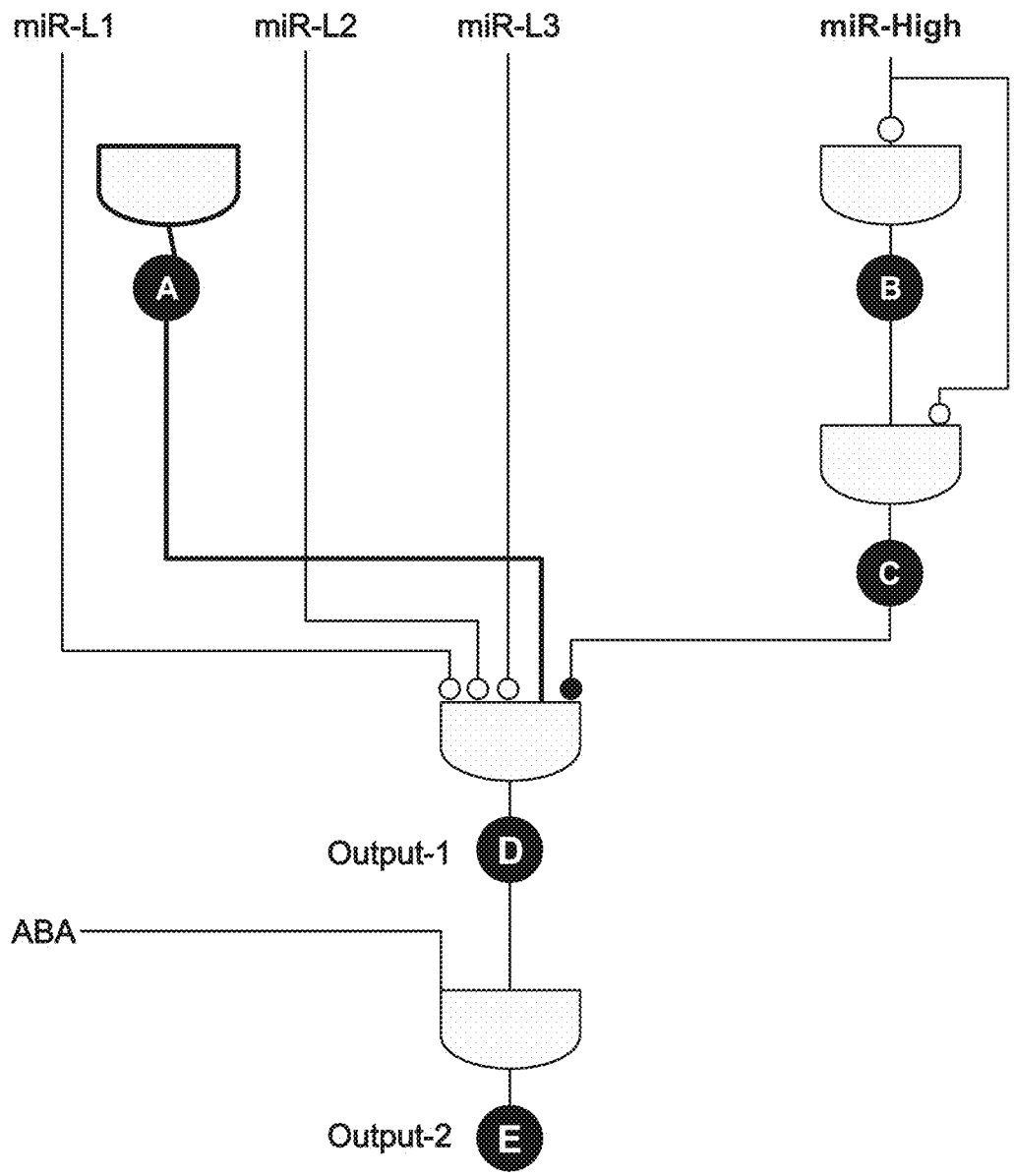
FIGS. 12A-12B: Schematics of Circuit 2.
Figure 12B:
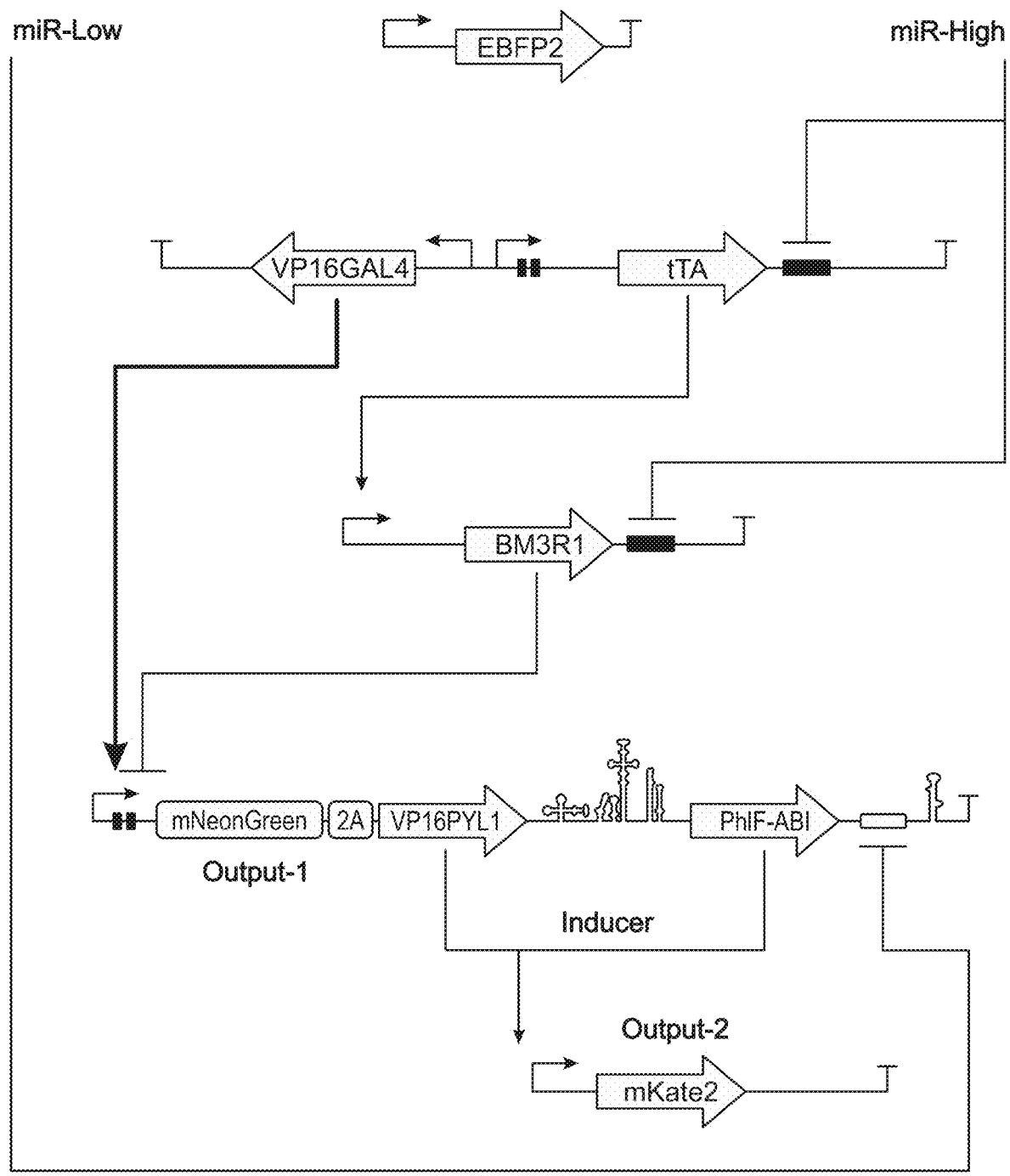
Figure 13A:
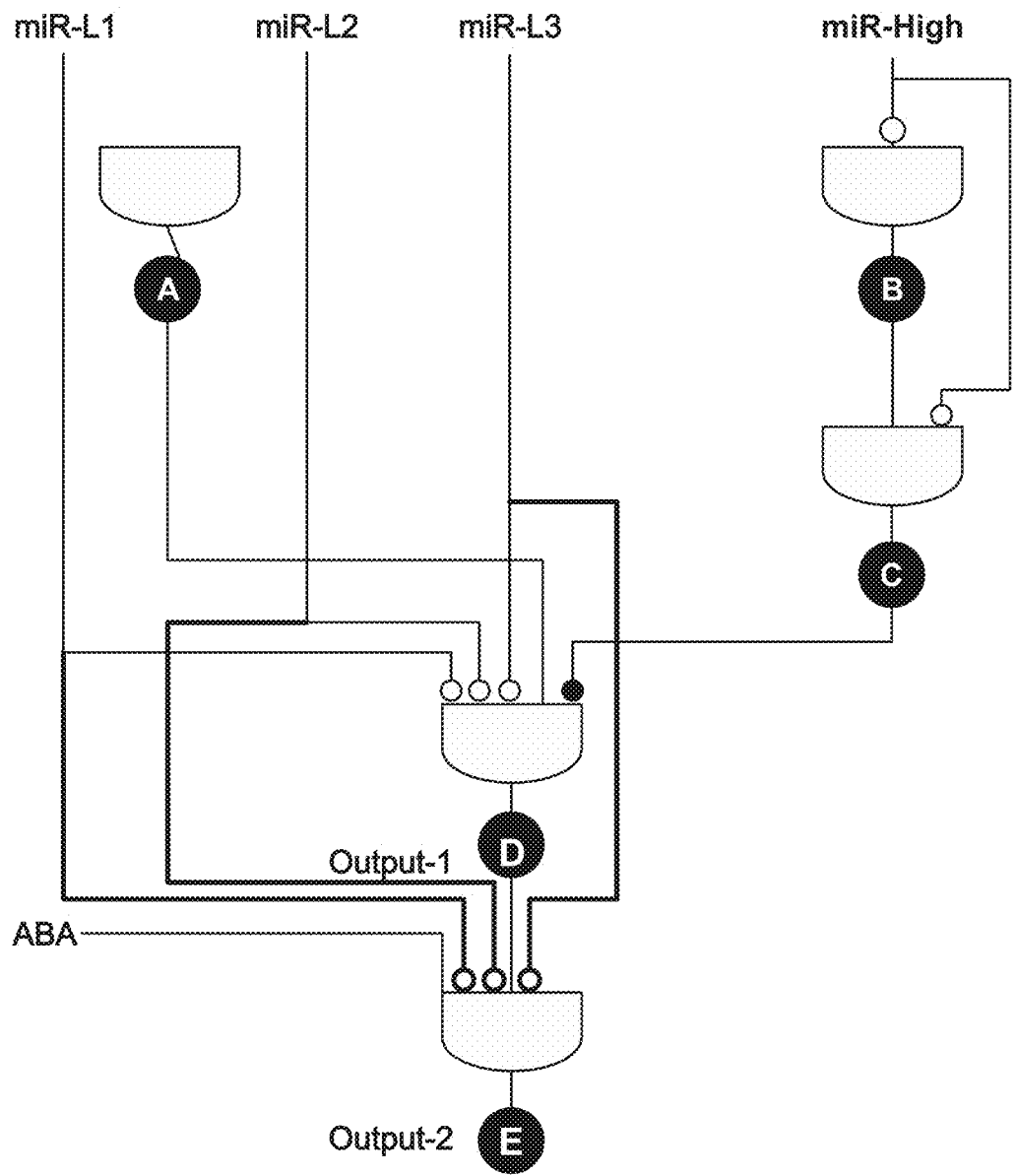
FIGS. 13A-13B: Schematics of Circuit 3.
Figure 13B:
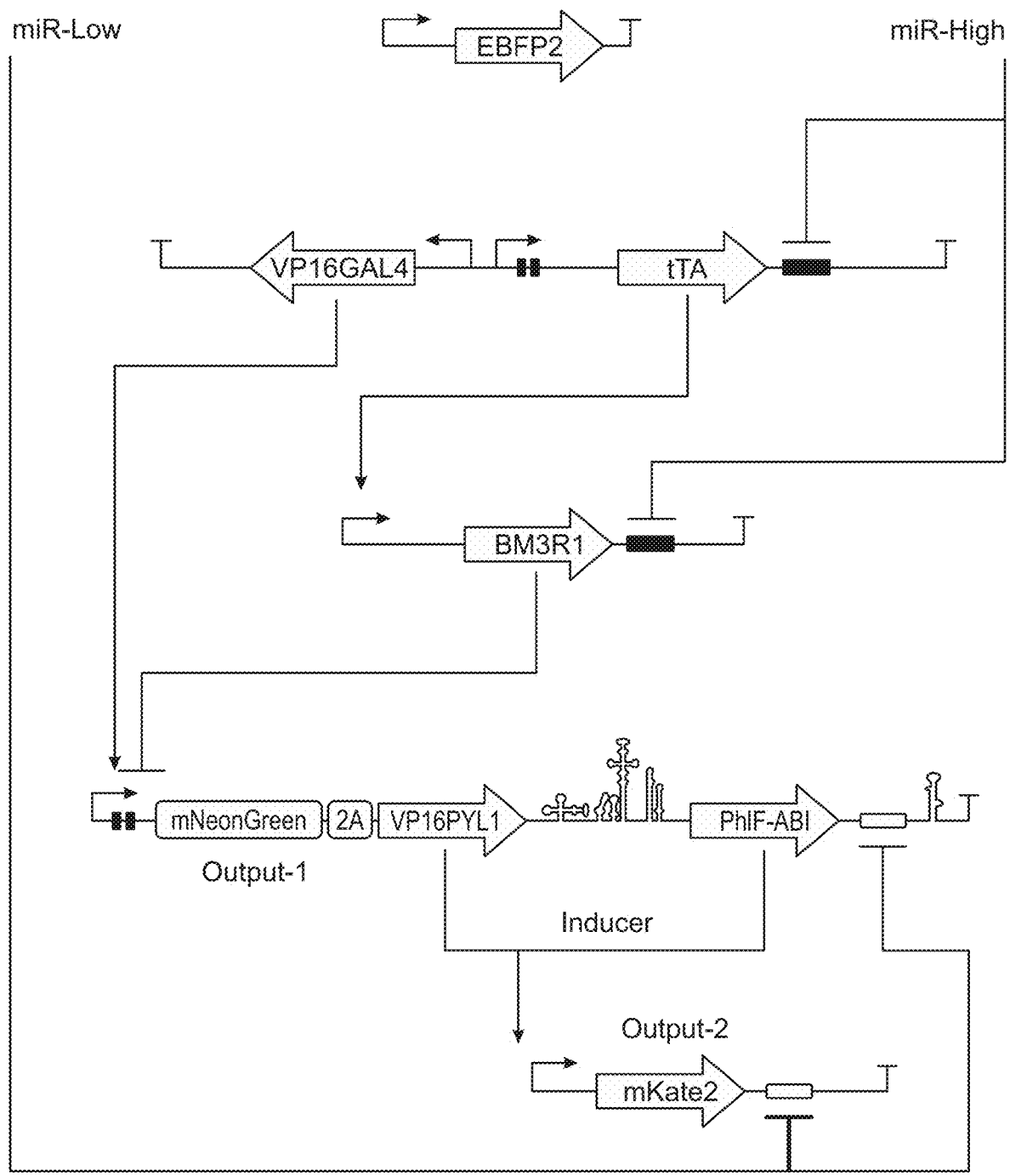
Figure 14A:
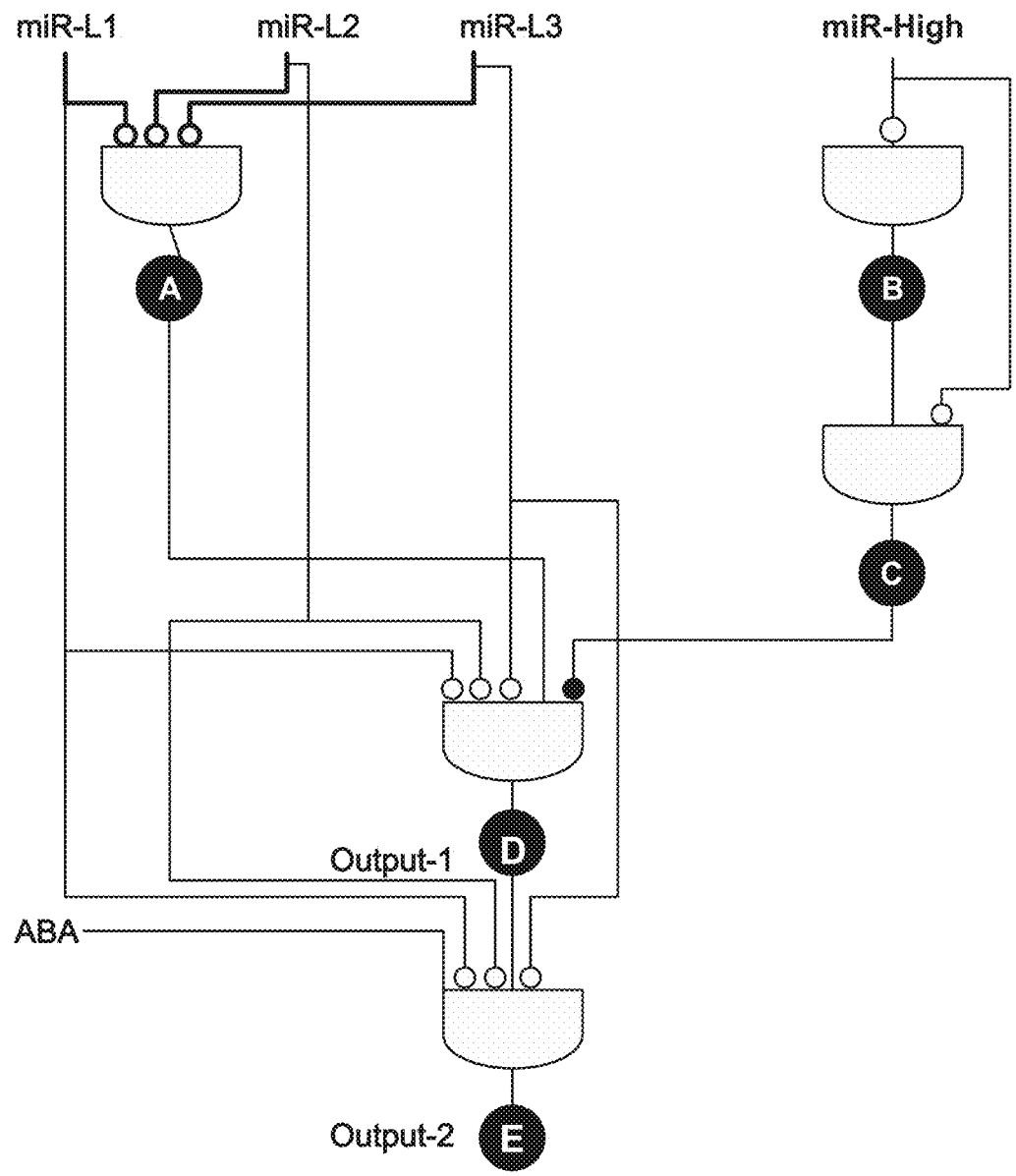
FIGS. 14A-14B: Schematics of Circuit 4.
Figure 14B:
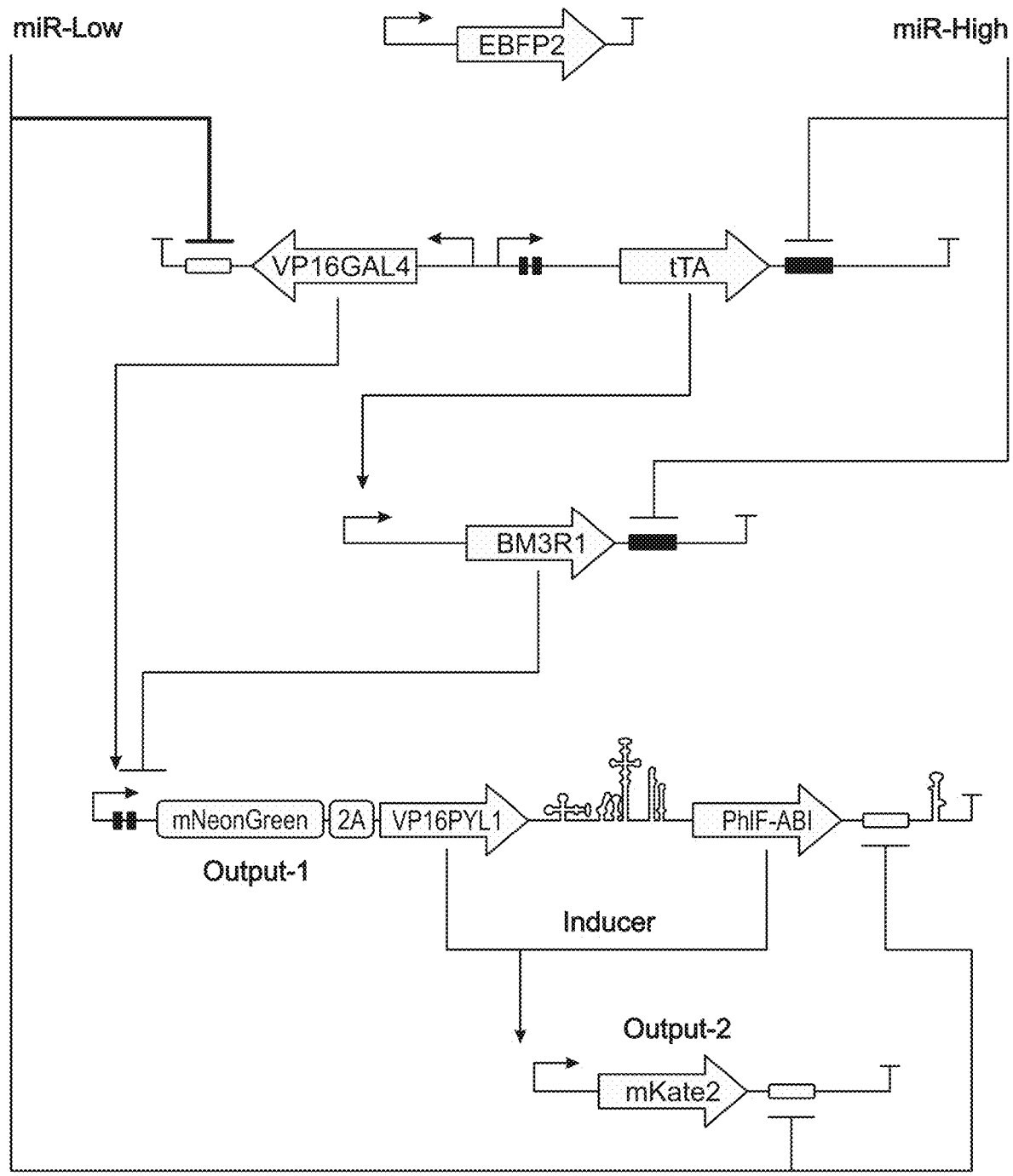
Figure 15A:
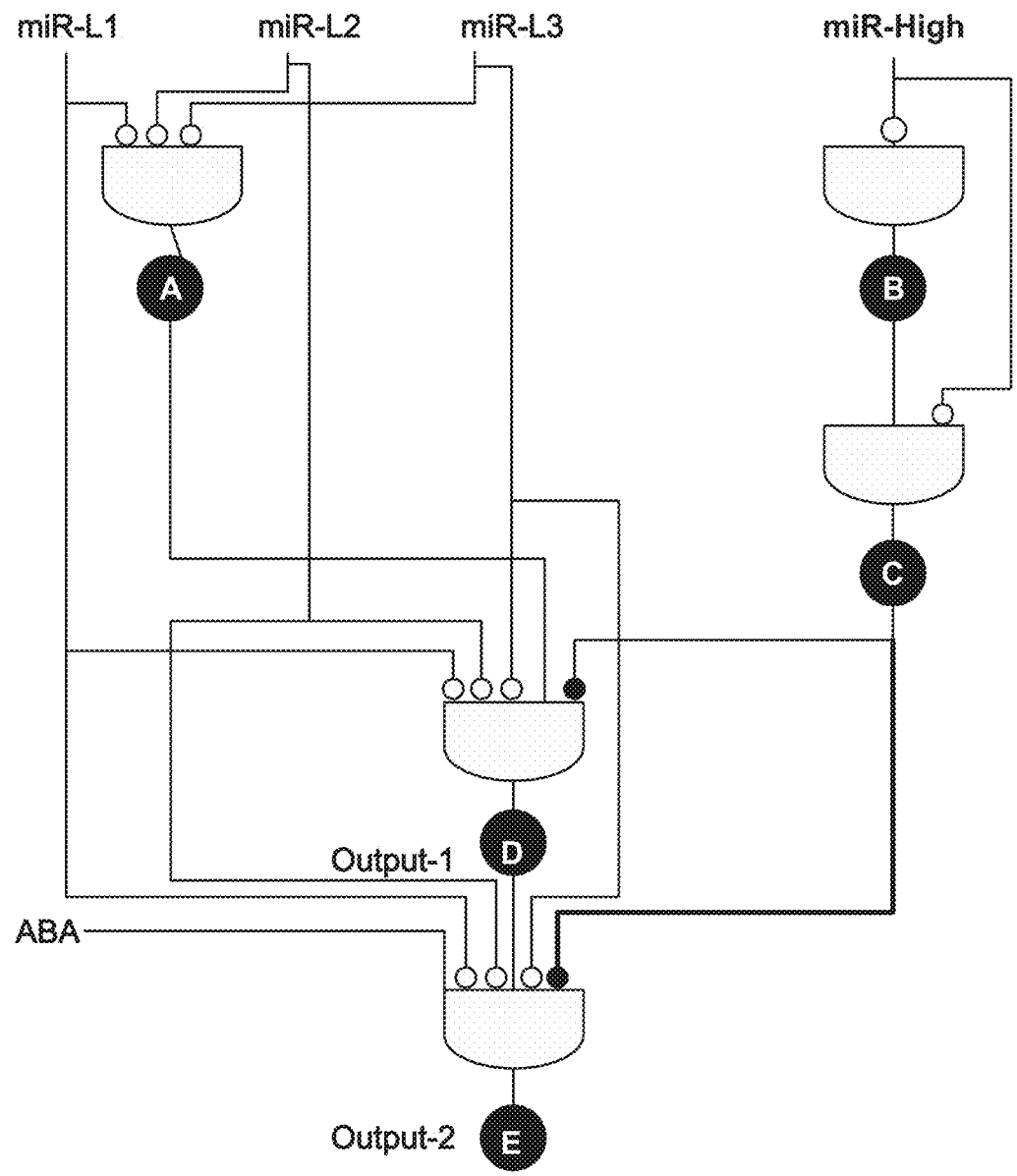
FIGS. 15A-15B: Schematics of Circuit 5.
Figure 15B:
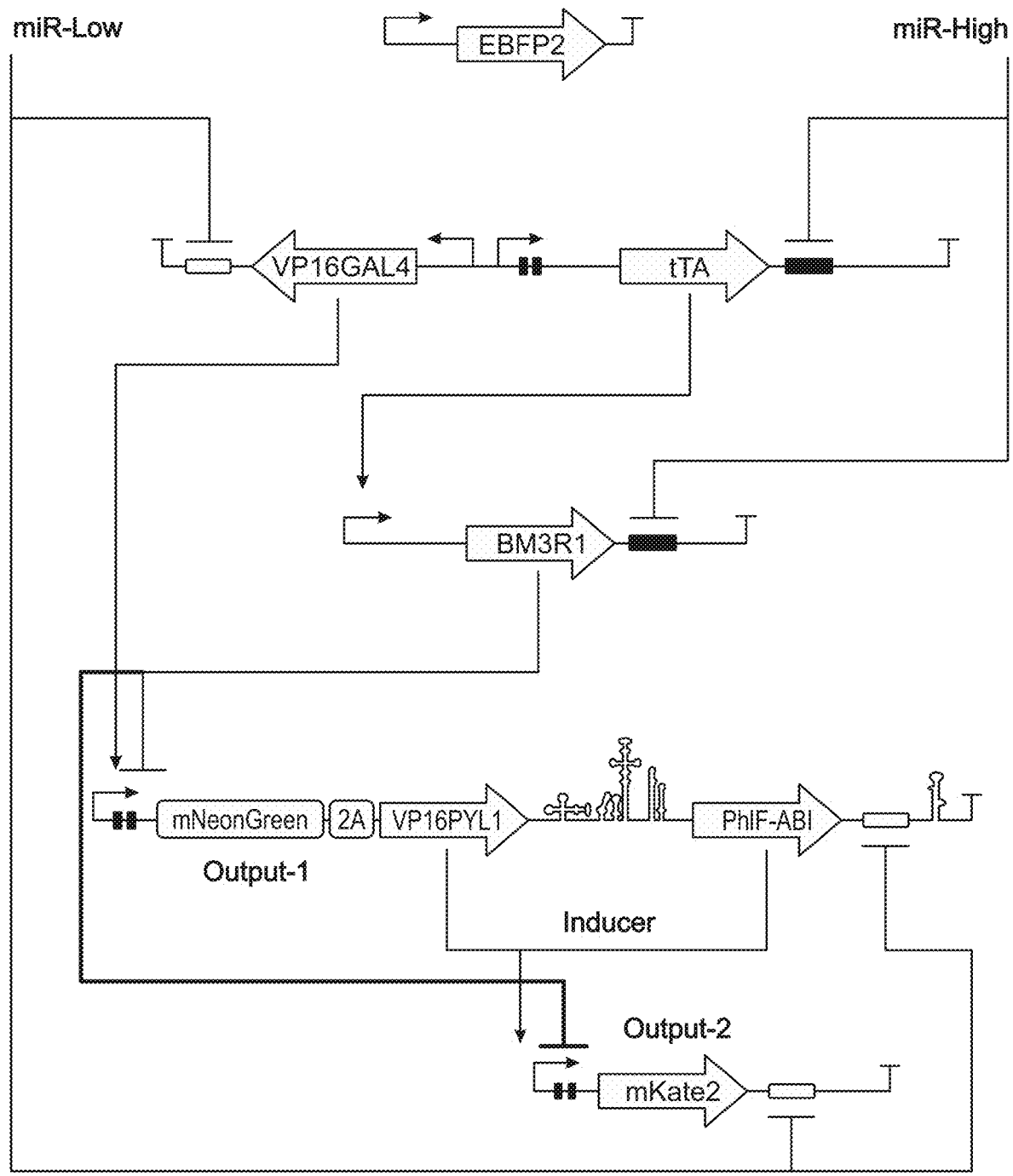
Figure 16A:
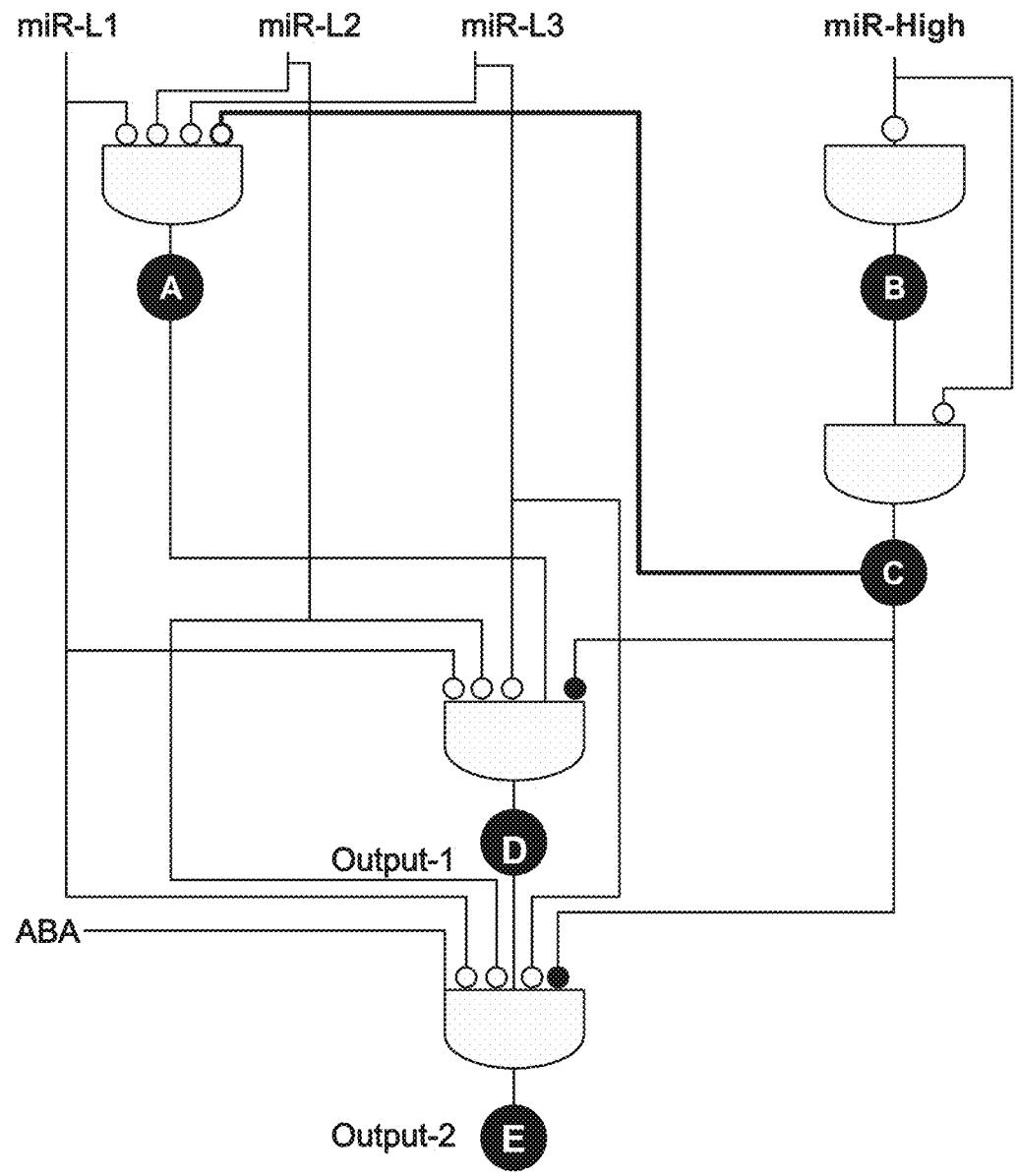
FIGS. 16A-16B: Schematics of Circuit 6.
Figure 16B:
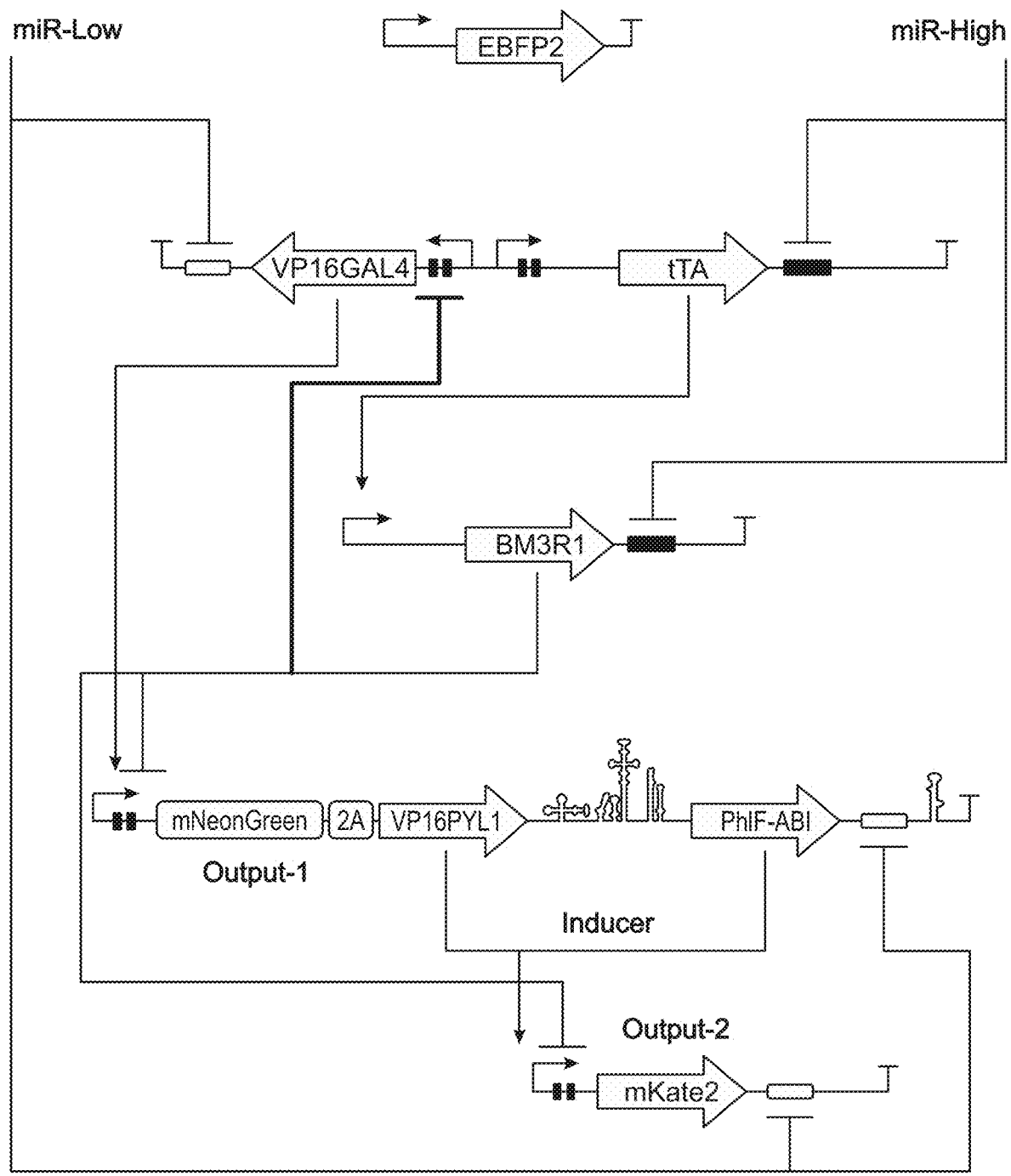
Figure 17A:
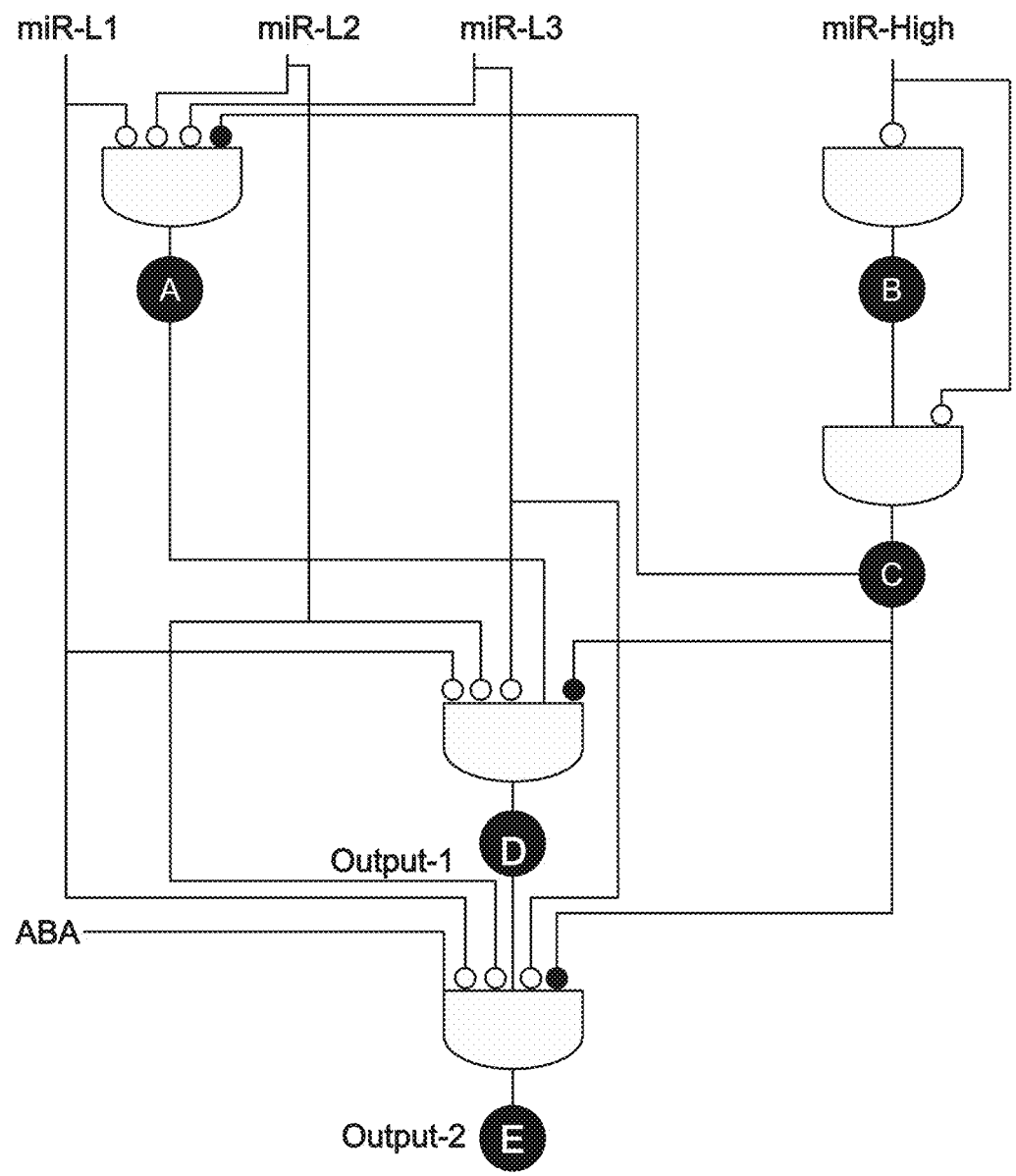
FIGS. 17A-17B: Schematics of Circuit 7.
Figure 17B:
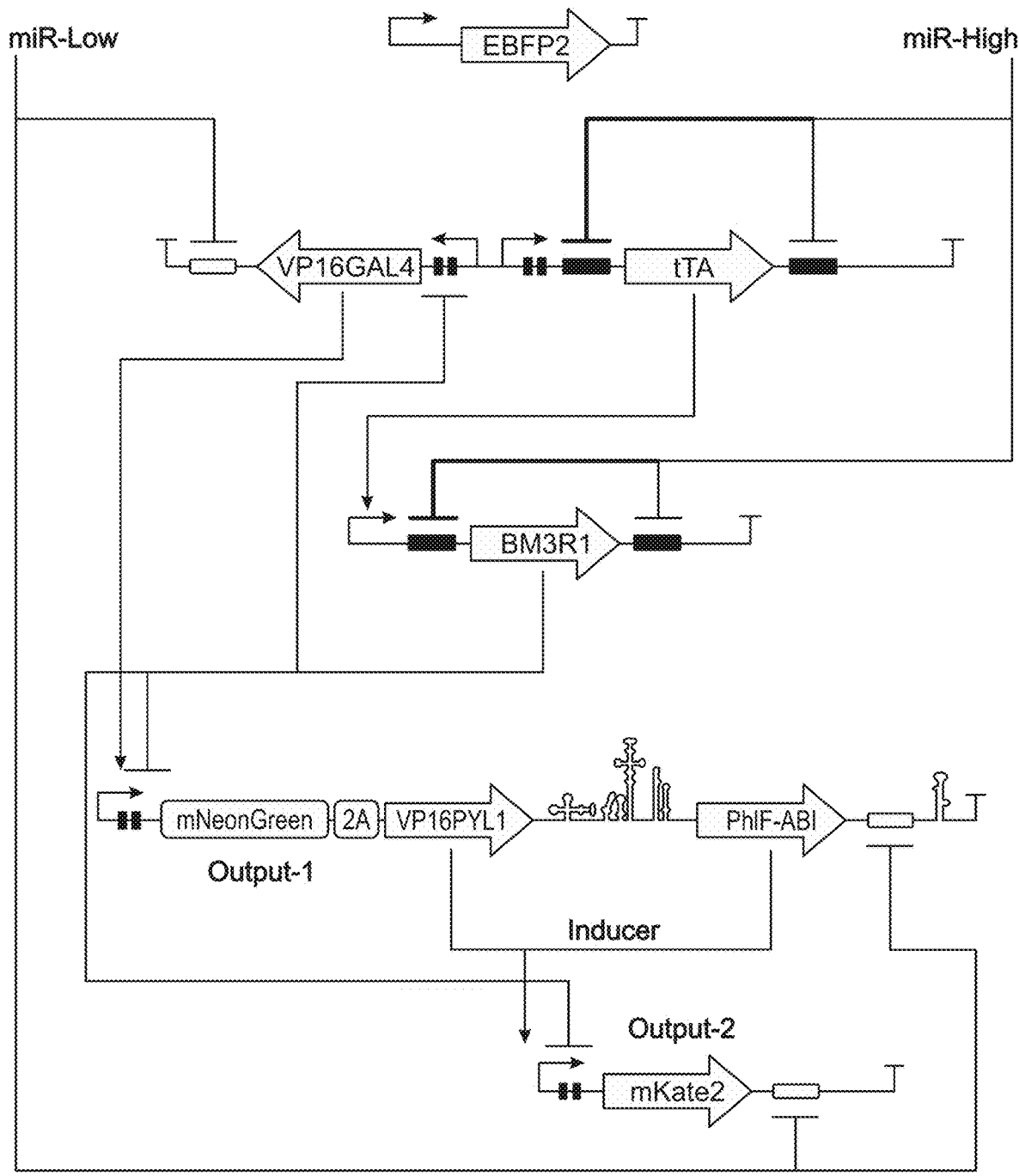
Figure 20A:
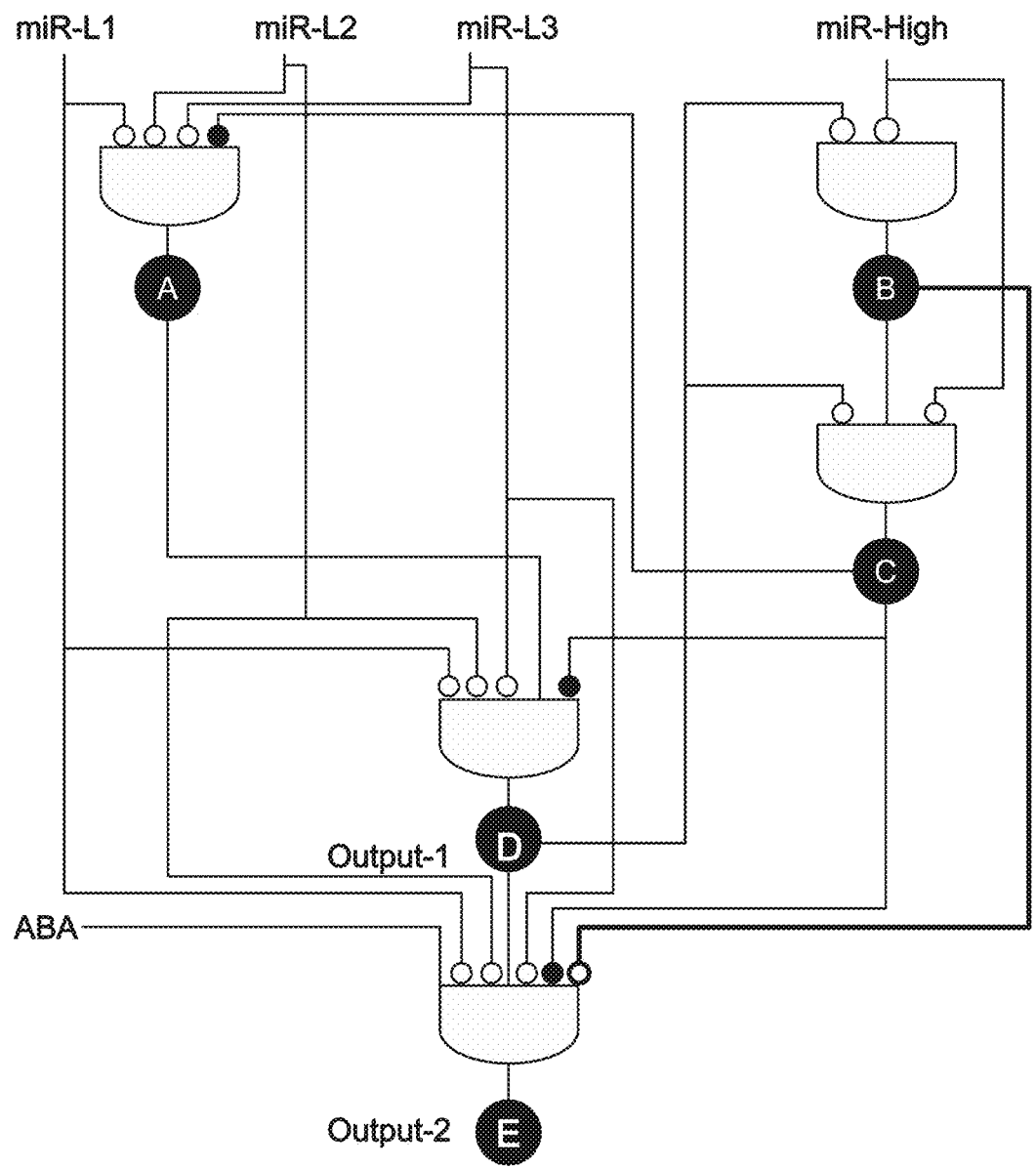
FIGS. 20A-20B: Schematics of Circuit 10.
Figure 20B:
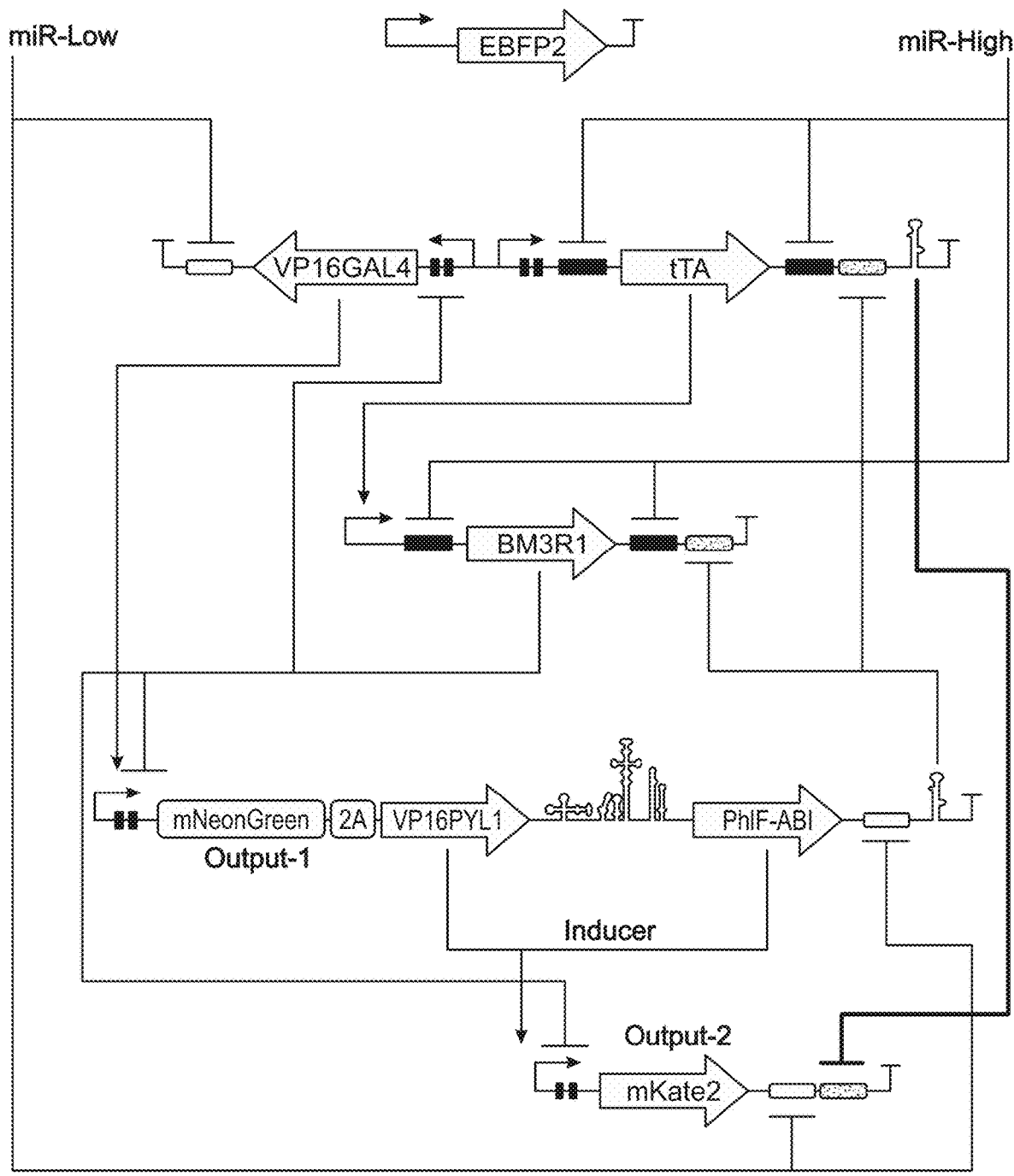
Figure 21A:
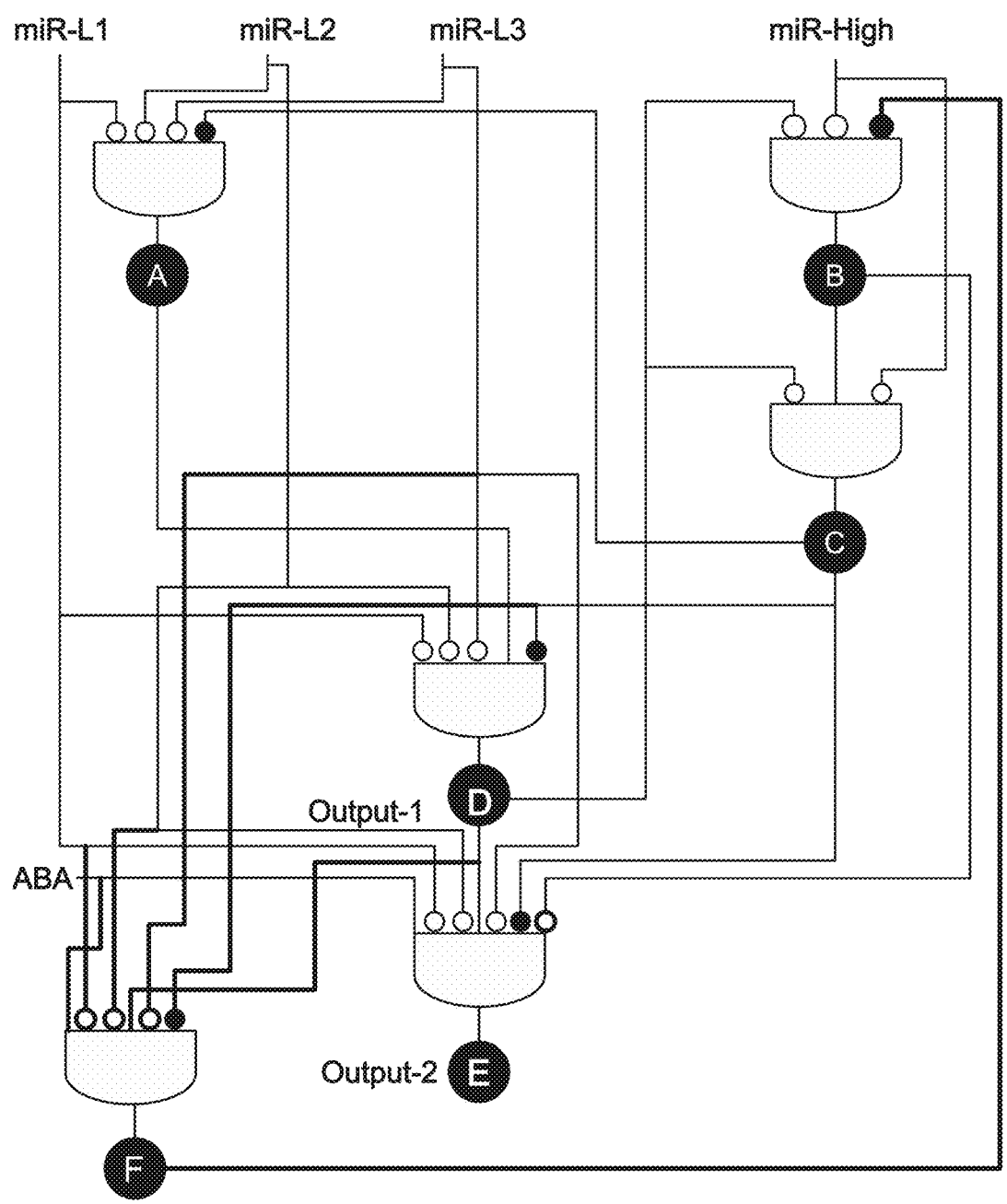
FIGS. 21A-21B: Schematics of Circuit 11.
Figure 21B:
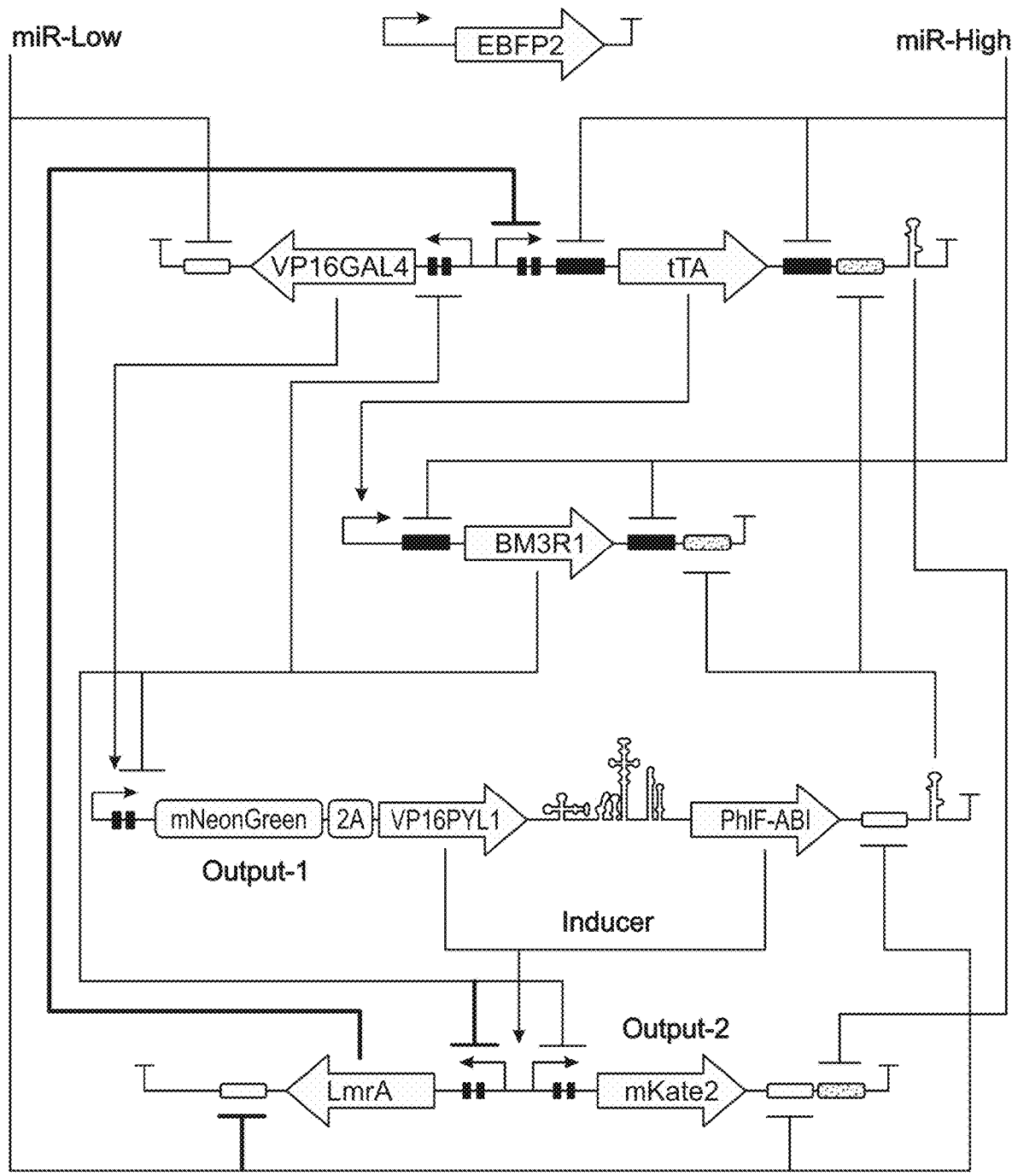
Figure 22A:
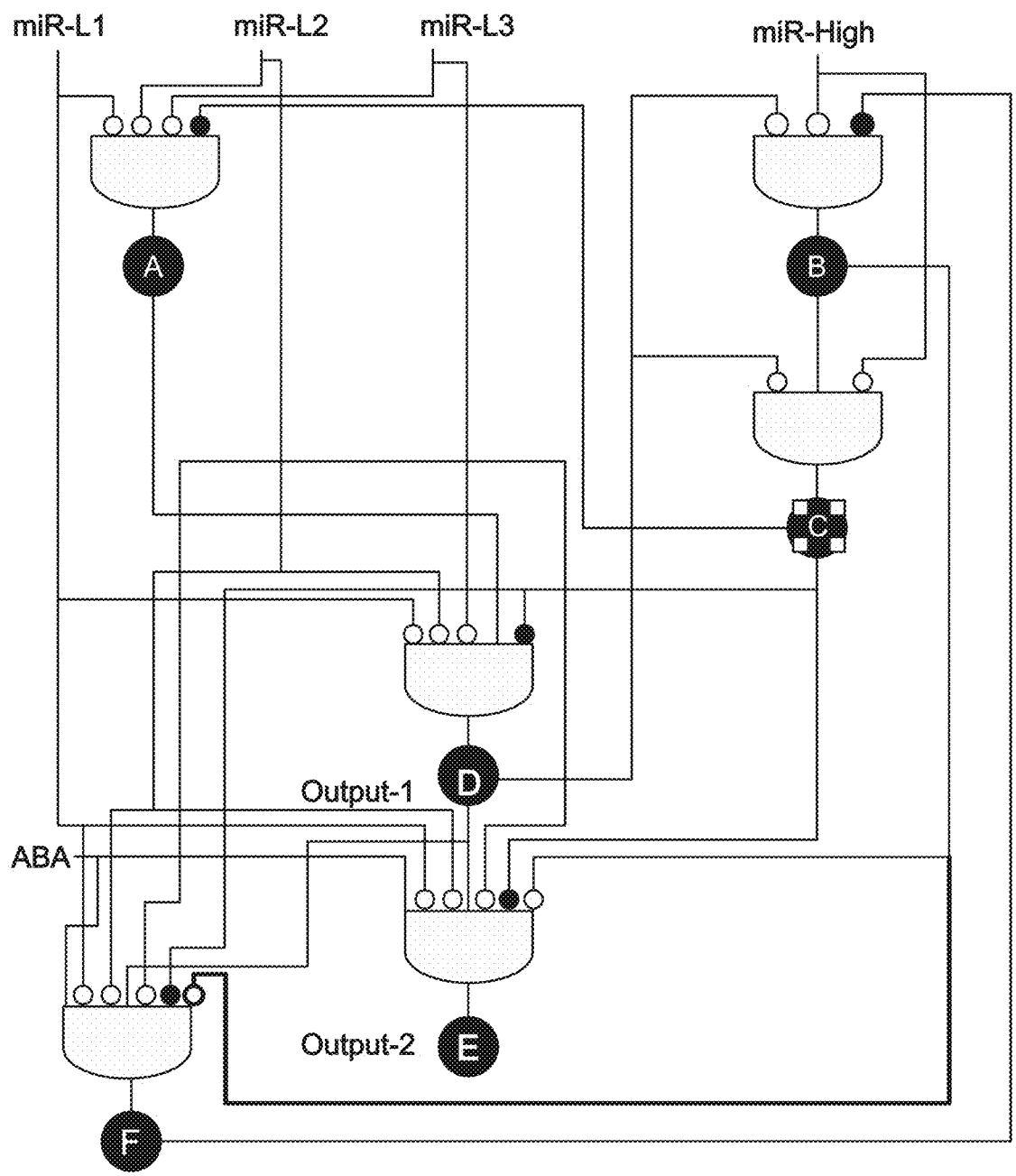
FIGS. 22A-22B: Schematics of Circuit 12.
Figure 22B:
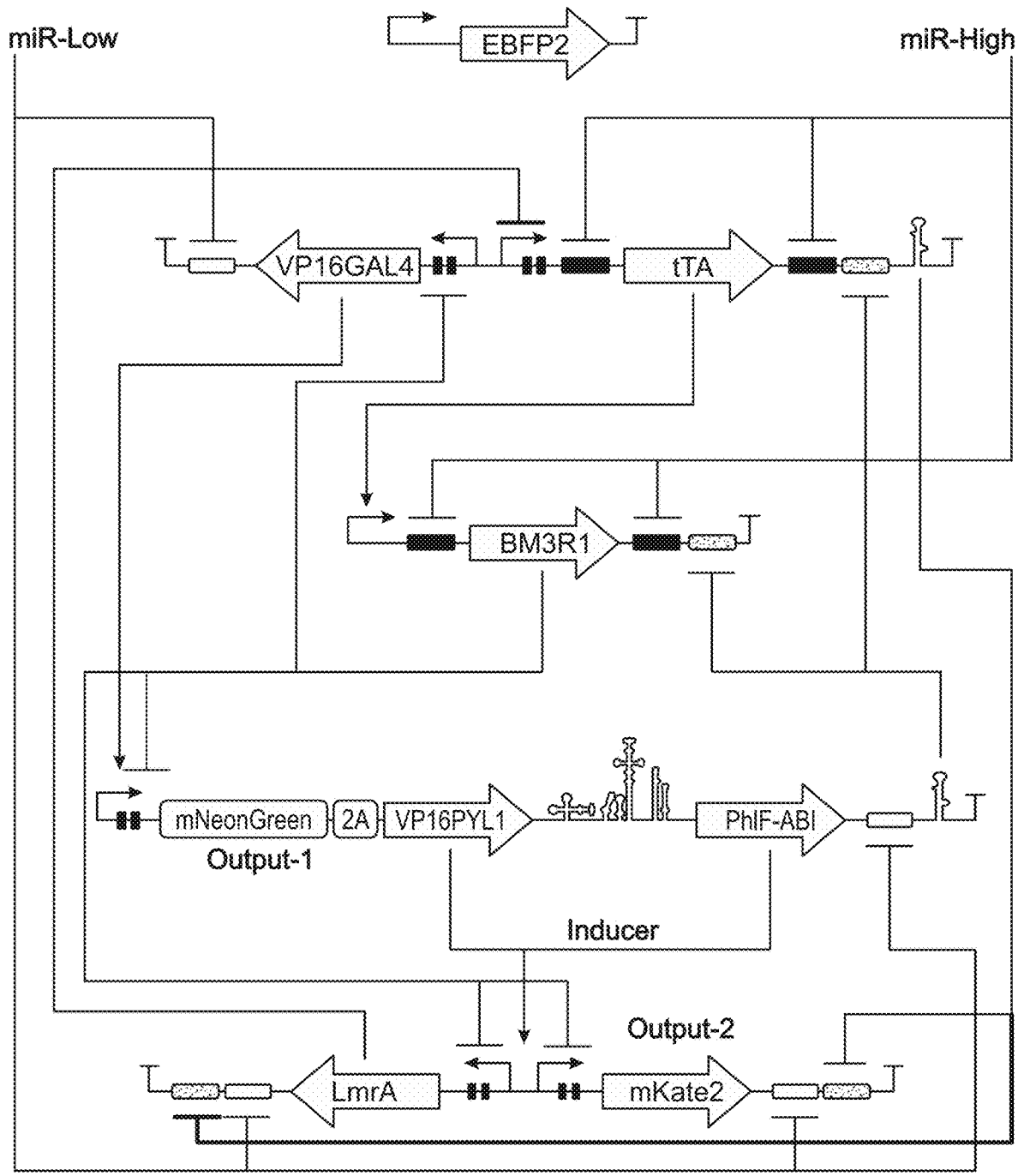

Genetic systems designed to detect microRNA expression in a cell and to classify the cell accordingly have been described in the art. The cell state classifiers described herein are superior to the genetic systems previously described, e.g., having improved specificity, sensitivity, and/or signal robustness. For example, Xie et al. (WO/2015165275) describes a genetic circuit that senses the expression of an microRNA (FIG. 20 of Xie et al.), and a genetic circuit that detects both microRNA-high and microRNA-low with one feedback loop incorporated (FIG. 9 of Xie et al.). However, Xie et al.'s cell state classifier design differs because it does not include the various regulatory elements included in the cell state classifiers described herein, which make the cell state classifier more tunable. Further, Benenson et al. (U.S. Pat. No. 9,458,509) describes a high-input detector module for classifying a cell based on microRNA expression, but Benenson et al. cell state classifier does not use an activatable/repressible promoter in its signal circuit, in contrast to the cell state classifiers described herein. Benenson et al. also does not describe the various feedforward/feedback loops included in the cell state classifiers described herein. These and other improvements in the cell state classifiers described herein confer performance advantages over previous cell state classifiers.

Components of the Cell State Classifier

The cell state classifier described herein comprises various genetic circuits (also termed "circuits") that perform different functions. A "genetic circuit" is a functional unit of the cell state classifier. The genetic circuits of the present disclosure may function in sensing the microRNA profile, producing output molecules, producing control signal, or regulating the signals sensed or produced by the cell state classifier.

In some embodiments, the cell state classifier comprises one or more (e.g., 1, 2, 3, 4, 5, 6, 7, 8, 9, 10, or more) sensor circuits. A "sensor circuit" is a genetic circuit that detects the microRNA profile of the cell. Different types of sensor circuits are used in the cell state classifier for detecting microRNA-high and microRNA-low. Sensor circuits comprise microRNA target sites for the microRNAs to be detected.

The cell state classifier comprises a first sensor circuit that detects a first set of (e.g., 1, 2, 3, 4, 5, 6, 7, 8, 9, 10, or more) microRNAs that do not express or express at a low (e.g., undetectable by the cell state classifier) level in a cell. Such first set of microRNAs are referred to as "microRNA-low" or "miR-low" herein. The first sensor circuit is also referred to interchangeably herein as the "microRNA-low sensor" or "miR-low sensor." As described herein, the first sensor circuit comprises one or more (e.g., 1, 2, 3, 4, 5, 6, 7, 8, 9, 10, or more) target sites of any one or more of the first set of microRNAs (microRNA-low) to be detected. One first sensor circuit may be used for the detection of one or multiple (e.g., 2, 3, 4, 5, 6, 7, 8, 9, 10, or more) microRNAs from the first set of microRNAs (microRNA-low). The first sensor circuit further comprises a promoter operably linked to a nucleotide sequence encoding a first activator. In some embodiments, the first microRNA target sites are downstream of the nucleotide sequence encoding the first activator. In some embodiments, the first microRNA target sites are upstream of the nucleotide sequence encoding the first activator. In some embodiments, the first microRNA target sites are downstream and upstream of the nucleotide sequence encoding the first activator. In some embodiments, the promoter of the first sensor circuit is a constitutive promoter. In some embodiments, the promoter of the first sensor circuit is an inducible promoter.

The cell state classifier comprises a second sensor circuit that detects a second set of (e.g., 1, 2, 3, 4, 5, 6, 7, 8, 9, 10, or more) microRNA that expresses at a high level (e.g., expression level is detectable by the cell state classifier or high) in a cell. Such second microRNA are referred to as "microRNA-high" or "miR-high" herein. The second sensor circuit is also referred to interchangeably herein as the "microRNA-high sensor" or "miR-high sensor." The second sensor circuit comprises two parts that are linked together via transcriptional control. The first part of the second sensor circuit comprises one or more (e.g., 1, 2, 3, 4, 5, 6, 7, 8, 9, 10, or more) target sites of the second microRNA (microRNA-high), and a promoter operably linked to a nucleotide sequence encoding a second activator, which is different from the first activator of the first sensor circuit. In some embodiments, the second microRNA target sites are downstream of the nucleotide sequence encoding the second activator. In some embodiments, the second microRNA target sites are upstream of the nucleotide sequence encoding the second activator. In some embodiments, the second microRNA target sites are downstream and upstream of the nucleotide sequence encoding the second activator. In some embodiments, the promoter of the first part of the second sensor circuit is a constitutive promoter. In some embodiments, the promoter of the first part of the second sensor circuit is an inducible promoter.

The second part of the second sensor circuit comprises one or more (e.g., 1, 2, 3, 4, 5, 6, 7, 8, 9, 10, or more) target sites of the second microRNA (microRNA-high), and a promoter that is activated by the second activator, operably linked to a nucleotide sequence encoding a first repressor. In some embodiments, the second microRNA target sites are downstream of the nucleotide sequence encoding the first repressor. In some embodiments, the second microRNA target sites are upstream of the nucleotide sequence encoding the first repressor. In some embodiments, the second microRNA target sites are downstream and upstream of the nucleotide sequence encoding the first repressor.

The first part and the second part of the second sensor circuit are linked via transcriptional control, in that the expression of the first activator leads to the expression of the first repressor. Further, the first part and the second part of the second sensor circuit both respond directly to the second microRNA via the target sites of the second microRNA. In some embodiments, the first repressor represses the promoter of the first sensor circuit.

In some embodiments, the cell state classifier is able to detect more than one of the second microRNA (microRNA-high). The detection of each microRNA-high requires a separate second sensor circuit. As such, in some embodiments, the cell state classifier of the present disclosure comprises a plurality (e.g., 2, 3, 4, 5, 6, 7, 8, 9, 10, or more) of the second sensor circuit, each second sensor circuit detects the expression of one second microRNA.

The cell state classifier described herein further comprises a first signal circuit. A "signal circuit," as used herein, refers to a genetic circuit that responds to the sensor circuits and in turn produces an output molecule. The first signal circuit of the present disclosure comprises one or more (e.g., 1, 2, 3, 4, 5, 6, 7, 8, 9, 10, or more) target sites for any one or more of the first set of microRNAs (microRNA-low), and a first activatable/repressible promoter operably linked to a nucleotide sequence encoding a first output molecule. In some embodiments, the first microRNA target sites are downstream of the nucleotide sequence encoding the first output molecule. In some embodiments, the first microRNA target sites are upstream of the nucleotide sequence encoding the first output molecule. In some embodiments, the first microRNA target sites are downstream and upstream of the nucleotide sequence encoding the first output molecule. An "activatable/repressible" promoter is a promoter that can be activated (e.g., by an activator) to drive the expression of the nucleotide sequence that it is operably linked to, and can be repressed (e.g., by a repressor) to repress the expression of the nucleotide sequence that it is operably linked to. The first activatable/repressible promoter of the present disclosure is activated by the first activator of the first sensor circuit or repressed by the first repressor of the second sensor circuit.

In some embodiments, the first sensor circuit produces the first output molecule when a matching microRNA profile is present. In some embodiments, the first output molecule is a detectable molecule. As such, detection of the first output molecule is an indication that a matching miRNA profile is present in a cell.

In some embodiments, another layer of control may be integrated into the cell state classifier such that a detectable output molecule is only expressed when a matching microRNA profile is present and when an inducer (e.g., an external inducer) is added. For example, the first signal circuit of the present disclosure may further comprise a nucleotide sequence encoding a third activator, operably linked to the first activatable/repressible promoter. Further, the cell state classifier may comprise a second signal circuit comprising a promoter that is activated by the third activator in the presence of an inducer, operably linked to a nucleotide sequence encoding a second output molecule. As such, the second output molecule only expresses when the third activator and the inducer are both present. In some embodiments, the promoter of the second signal circuit may be a second activatable/repressible promoter that is activated by the third activator in the presence of an inducer and repressed by the first repressor.

In some embodiments, the second signal circuit further comprises one or more (e.g., 1, 2, 3, 4, 5, 6, 7, 8, 9, 10, or more) target sites for any one or more of the first set of microRNA (microRNA-low). In some embodiments, the target sites for any one of the first set of microRNA (microRNA-low) are downstream of the nucleotide sequence encoding the second output molecule. In some embodiments, the target sites for any one of the first set of microRNA (microRNA-low) are upstream of the nucleotide sequence encoding the second output molecule. In some embodiments, the target sites for any one of the first set of microRNA (microRNA-low) are downstream and upstream of the nucleotide sequence encoding the second output molecule.

In some embodiments, additional regulatory elements may be added to the cell state classifier to enhance its performance (e.g., sensitivity, specificity, and/or robustness). In some embodiments, such regulatory elements may be feed-forward and/or feed-back transcriptional regulation loops. For example, in some embodiments, the first signal circuit further comprises a nucleotide sequence encoding a first regulatory microRNA. The first regulatory microRNA is different from any one of the first set of microRNAs or the second set of microRNAs. Further, one or more target sites of the first regulatory microRNA may be placed into the first part of the second sensor circuit. In some embodiments, the target sites of the first regulatory microRNA are downstream of the nucleotide sequence encoding the second activator. In some embodiments, the target sites of the first regulatory microRNA are upstream of the nucleotide sequence encoding the second activator. In some embodiments, the target sites of the first regulatory microRNA are downstream and upstream of the nucleotide sequence encoding the second activator.

In some embodiments, the second part of the second sensor circuit further comprises one or more target sites (e.g., 1, 2, 3, 4, 5, 6, 7, 8, 9, 10, or more) for the first regulatory microRNA. In some embodiments, the target sites of the first regulatory microRNA are downstream of the nucleotide sequence encoding the first repressor. In some embodiments, the target sites of the first regulatory microRNA are upstream of the nucleotide sequence encoding the first repressor. In some embodiments, the target sites of the first regulatory microRNA are downstream and upstream of the nucleotide sequence encoding the first repressor.

In some embodiments, the first part of the second sensor circuit further comprises a nucleotide sequence encoding a second regulatory microRNA, operably linked to the promoter of the first part of the second sensor circuit. The second regulatory microRNA is not the same as any of the first set of microRNAs, the second microRNA, or the first regulatory microRNA. One or more (e.g., 1, 2, 3, 4, 5, 6, 7, 8, 9, 10, or more) target sites of the second regulatory microRNA may be placed in the second signal circuit. In some embodiments, the target sites of the second regulatory microRNA are downstream of the nucleotide sequence encoding the second activator. In some embodiments, the target sites of the second regulatory microRNA are upstream of the nucleotide sequence encoding the second activator. In some embodiments, the target sites of the second regulatory microRNA are downstream and upstream of the nucleotide sequence encoding the second activator.

In some embodiments, the cell state classifier further comprises a regulatory circuit. The regulator circuit comprises a second activatable/repressible promoter operably linked to a nucleotide encoding a second repressor and one or more target sites for any one of the first set of microRNAs (microRNA-low). In some embodiments, the second activatable/repressible promoter is activated by the third activator in the presence of an inducer and repressed by the first repressor. In some embodiments, the second repressor represses the promoter of the first part of the second sensor circuit.

In some embodiments, the cell state classifier of the present disclosure further comprises a control circuit. A "control circuit" refers to a circuit that produces a constant signal independent of the input (e.g., the microRNA profile of a cell) and may be used to control for variations caused by other factors other than the microRNA profile, e.g., transfection, cellular health, etc. The control circuit comprises a constitutive promoter operably linked to a nucleotide sequence encoding a control signal that is different from the first output molecule or the second output molecule. The control signal is typically a detectable molecule such as a fluorescent molecule.

Genetic Elements and Combinatorial Library of Circuit Variants

Further provided herein are the various genetic elements used in the genetic circuits of the cell state classifier. A "genetic element" refers to a particular nucleotide sequence that has a role in nucleic acid expression (e.g., promoter, enhancer, terminator) or encodes a discrete product of a genetic circuit (e.g., an activator, a repressor, a microRNA, or an output molecule).

The first and second sensor circuits of the cell state classifier "senses" microRNAs via microRNA target sites present in the sensor circuits. A "microRNA" or "miRNA" is a small non-coding RNA molecule that functions in RNA silencing and post-transcriptional regulation of gene expression (e.g., as described in Ambros et al., *Nature* 431 (7006): 350-5, 2004; and Bartel et al., *Cell.* 136 (2): 215-33, 2004). A microRNA may be 15-30 nucleotides in length. For example, a microRNA may be 15-30, 15-25, 15-20, 20-30, 20-25, or 25-30 nucleotides in length. In some embodiments, a microRNA may be 16-24 nucleotides in length. In some embodiments, a microRNA may be 20-24 nucleotides in length. In some embodiments, a microRNA may be 15, 16, 17, 18, 19, 20, 21, 22, 23, 24, 25, 26, 27, 28, 29, or 30 nucleotides in length.

A "microRNA target site" is a nucleotide sequence that is complementary to the nucleotide sequence of the microRNA. Naturally, microRNA targeting sites exist in messenger RNAs (mRNA), typically in the 3' untranslated regions of mRNAs. Binding of the microRNA to its target site in via sequence complementarity leads to silencing of an output molecule either via degrading the mRNA or suppressing translation of the mRNA (e.g., as described in Bartel et al., *Cell* 136 (2): 215-33 (2009), incorporated herein by reference) containing the microRNA binding sites. Herein, when microRNA target sites are referred in the context of the genetic circuits (i.e., in a context of DNA), it intends to mean the nucleotide sequence that encodes the microRNA target sites in the mRNA that is produced from the genetic circuit. As described herein, designated microRNA target sites are placed either upstream or downstream, or both, of a coding sequence in genetic circuits. As such, when a mRNA of such coding sequence is produced from the genetic circuit, the microRNA target sites are present in the 5' UTR or 3' UTR, or both 5' and 3' UTRs in the mRNA. Including microRNA target sides in multiple non-coding regions of a mRNA strengths the inhibitory effect of the microRNA on the gene encoded by the mRNA.

One skilled in the art is familiar with the mechanism of gene silencing by microRNAs. For example, in the cell state classifiers of the present disclosure, if a microRNA is expressed and a sensor circuit (e.g., the first or second sensor circuit) comprise one or more (e.g., 1, 2, 3, 4, 5, 6, 7, 8, 9, 10, or more) targets sites of the microRNA (either upstream or downstream of the coding sequence, or both), the microRNA can bind to the target sites in the mRNA produced by the sensor circuit and mediate the degradation of the mRNA, thus reducing the expression of the protein encoded by the mRNA (translational control). In some embodiments, expression of the protein encoded by the mRNA is reduced by at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 99-fold, or more compared to when the microRNA is not present. In some embodiments, expression of the protein encoded by the mRNA is no more than 1%, no more than 5%, no more than 10%, no more than 20%, no more than 30%, no more than 40%, no more than 50%, no more than 60%, no more than 70%, no more than 80% of the output molecule when the microRNA is not present. In some embodiments, a higher/lower level of the microRNA results in a higher/lower decrease in the protein encoded by the mRNA containing the microRNA target sites.

Information about the sequences, origins, and functions of known microRNAs maybe found in publically available databases (e.g., mirbase.org/, all versions, as described in Kozomara et al., *Nucleic Acids Res* 2014 42:D68-D73; Kozomara et al., *Nucleic Acids Res* 2011 39:D152-D157; Griffiths-Jones et al., *Nucleic Acids Res* 2008 36:D154-D158; Griffiths-Jones et al., *Nucleic Acids Res* 2006 34:D140-D144; and Griffiths-Jones et al., *Nucleic Acids Res* 2004 32:D109-D111, including the most recently released version miRBase 21, which contains "high confidence" microRNAs). Non-limiting examples of microRNAs that are expressed in cells and are able to be detected by the cell state classifier are: FF4, FF5, let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a.

In some embodiments, the microRNA detected using the cell state classifier of the present disclosure is selected from: hsa-let-7a-2-3p, hsa-let-7a-3p, hsa-let-7a-5p, hsa-let-7b-3p, hsa-let-7b-5p, hsa-let-7c-5p, hsa-let-7d-3p, hsa-let-7d-5p, hsa-let-7e-3p, hsa-let-7e-5p, hsa-let-7f-1-3p, hsa-let-7f-2-3p, hsa-let-7f-5p, hsa-let-7g-3p, hsa-let-7g-5p, hsa-let-7i-5p, hsa-miR-1, hsa-miR-1-3p, hsa-miR-1-5p, hsa-miR-100-3p, hsa-miR-100-5p, hsa-miR-101-3p, hsa-miR-101-5p, hsa-miR-103a-2-5p, hsa-miR-103a-3p, hsa-miR-105-3p, hsa-miR-105-5p, hsa-miR-106a-3p, hsa-miR-106a-5p, hsa-miR-106b-3p, hsa-miR-106b-5p, hsa-miR-107, hsa-miR-10a-3p, hsa-miR-10a-5p, hsa-miR-10b-3p, hsa-miR-10b-5p, hsa-miR-1185-1-3p, hsa-miR-1185-2-3p, hsa-miR-1185-5p, hsa-miR-122a-5p, hsa-miR-1249-3p, hsa-miR-1249-5p, hsa-miR-124a-3p, hsa-miR-125a-3p, hsa-miR-125a-5p, hsa-miR-125b-1-3p, hsa-miR-125b-2-3p, hsa-miR-125b-5p, hsa-miR-126-3p, hsa-miR-126-5p, hsa-miR-127-3p, hsa-miR-1271-3p, hsa-miR-1271-5p, hsa-miR-1278, hsa-miR-128-1-5p, hsa-miR-128-2-5p, hsa-miR-128-3p, hsa-miR-1285-3p, hsa-miR-1285-5p, hsa-miR-1287-3p, hsa-miR-1287-5p, hsa-miR-129-1-3p, hsa-miR-129-2-3p, hsa-miR-129-5p, hsa-miR-1296-3p, hsa-miR-1296-5p, hsa-miR-1304-3p, hsa-miR-1304-5p, hsa-miR-1306-3p, hsa-miR-1306-5p, hsa-miR-1307-3p, hsa-miR-1307-5p, hsa-miR-130a-3p, hsa-miR-130b-3p, hsa-miR-130b-5p, hsa-miR-132-3p, hsa-miR-132-5p, hsa-miR-133a-3p, hsa-miR-133a-5p, hsa-miR-133b, hsa-miR-134-3p, hsa-miR-134-5p, hsa-miR-135a-3p, hsa-miR-135a-5p, hsa-miR-135b-3p, hsa-miR-135b-5p, hsa-miR-136-3p, hsa-miR-136-5p, hsa-miR-138-1-3p, hsa-miR-138-5p, hsa-miR-139-3p, hsa-miR-139-5p, hsa-miR-140-3p, hsa-miR-140-5p, hsa-miR-141-3p, hsa-miR-141-5p, hsa-miR-142-3p, hsa-miR-142-5p, hsa-miR-143-3p, hsa-miR-143-5p, hsa-miR-144-3p, hsa-miR-144-5p, hsa-miR-145-5p, hsa-miR-146a-3p, hsa-miR-146a-5p, hsa-miR-147a, hsa-miR-148a-3p, hsa-miR-148a-5p, hsa-miR-148b-3p, hsa-miR-148b-5p, hsa-miR-149-3p, hsa-miR-144-3p, hsa-miR-150-3p, hsa-miR-150-5p, hsa-miR-151a-3p, hsa-miR-151a-5p, hsa-miR-152-3p, hsa-miR-152-5p, hsa-miR-154-3p, hsa-miR-154-5p, hsa-miR-155-3p, hsa-miR-155-5p, hsa-miR-15a-3p, hsa-miR-15a-5p, hsa-miR-15b-3p, hsa-miR-15b-5p, hsa-miR-16-1-3p, hsa-miR-16-2-3p, hsa-miR-16-5p, hsa-miR-17-3p, hsa-miR-17-5p, hsa-miR-181a-3p, hsa-miR-181a-5p, hsa-miR-181b-2-3p, hsa-miR-181b-5p, hsa-miR-181c-5p, hsa-miR-181d-3p, hsa-miR-181d-5p, hsa-miR-182-3p, hsa-miR-182-5p, hsa-miR-183-3p, hsa-miR-183-5p, hsa-miR-185-3p, hsa-miR-185-5p, hsa-miR-186-3p, hsa-miR-186-5p, hsa-miR-188-3p, hsa-miR-188-5p, hsa-miR-18a-3p, hsa-miR-18a-5p, hsa-miR-18b-5p, hsa-miR-1908-3p, hsa-miR-1908-5p, hsa-miR-190a-3p, hsa-miR-190a-5p, hsa-miR-191-3p, hsa-miR-191-5p, hsa-miR-1910-3p, hsa-miR-1910-5p, hsa-miR-192-3p, hsa-miR-192-5p, hsa-miR-193a-3p, hsa-miR-193a-5p, hsa-miR-193b-3p, hsa-miR-193b-5p, hsa-miR-194-3p, hsa-miR-194-5p, hsa-miR-195-3p, hsa-miR-195-5p, hsa-miR-196a-3p, hsa-miR-196a-5p, hsa-miR-196b-3p, hsa-miR-196b-5p, hsa-miR-197-3p, hsa-miR-197-5p, hsa-miR-199a-3p, hsa-miR-199a-5p, hsa-miR-199b-3p, hsa-miR-199b-5p, hsa-miR-19a-3p, hsa-miR-19a-5p, hsa-miR-19b-1-5p, hsa-miR-19b-2-5p, hsa-miR-19b-3p, hsa-miR-200a-3p, hsa-miR-200a-5p, hsa-miR-200b-3p, hsa-miR-200b-5p, hsa-miR-200c-3p, hsa-miR-200c-5p, hsa-miR-202-3p, hsa-miR-202-5p, hsa-miR-203a-3p, hsa-miR-203a-5p, hsa-miR-204-5p, hsa-miR-208b-3p, hsa-miR-208b-5p, hsa-miR-20a-3p, hsa-miR-20a-5p, hsa-miR-20b-3p, hsa-miR-20b-5p, hsa-miR-21-5p, hsa-miR-210-3p, hsa-miR-210-5p, hsa-miR-211-3p, hsa-miR-211-5p, hsa-miR-2116-3p, hsa-miR-2116-5p, hsa-miR-212-3p, hsa-miR-214-3p, hsa-miR-215-5p, hsa-miR-217, JG miR-218-1-3p, hsa-miR-218-5p, hsa-miR-219a-1-3p, hsa-miR-219a-2-3p, hsa-miR-219a-5p, hsa-miR-219b-3p, hsa-miR-219b-5p, hsa-miR-22-3p, hsa-miR-22-5p, hsa-miR-221-3p, hsa-miR-221-5p, hsa-miR-222-3p, hsa-miR-222-5p, hsa-miR-223-3p, hsa-miR-223-5p, hsa-miR-23a-3p, hsa-miR-23a-5p, hsa-miR-23b-3p, hsa-miR-24-1-5p, hsa-miR-25-3p, hsa-miR-25-5p, hsa-miR-26a-1-3p, hsa-miR-26a-2-3p, hsa-miR-26a-5p, hsa-miR-26b-5p, hsa-miR-27a-3p, hsa-miR-27a-5p, hsa-miR-27b-3p, hsa-miR-27b-5p, hsa-miR-28-3p, hsa-miR-28-5p, hsa-miR-296-3p, hsa-miR-296-5p, hsa-miR-299-3p, hsa-miR-299-5p, hsa-miR-29a-3p, hsa-miR-29a-5p, hsa-miR-29b-1-5p, hsa-miR-29b-3p, hsa-miR-29c-3p, hsa-miR-301a-3p, hsa-miR-301a-5p, hsa-miR-301b-3p, hsa-miR-301b-5p, hsa-miR-302a-3p, hsa-miR-302a-5p, hsa-miR-302b-5p, hsa-miR-302c-3p, hsa-miR-302c-5p, hsa-miR-3065-3p, hsa-miR-3065-5p, hsa-miR-3074-3p, hsa-miR-3074-5p, hsa-miR-30a-3p, hsa-miR-30a-5p, hsa-miR-30b-3p, hsa-miR-30b-5p, hsa-miR-30c-1-3p, hsa-miR-30c-2-3p, hsa-miR-30c-5p, hsa-miR-30d-3p, hsa-miR-30d-5p, hsa-miR-30e-3p, hsa-miR-30e-5p, hsa-miR-31-3p, hsa-miR-31-5p, hsa-miR-3130-3p, hsa-miR-3130-5p, hsa-miR-3140-3p, hsa-miR-3140-5p, hsa-miR-3144-3p, hsa-miR-3144-5p, hsa-miR-3158-3p, hsa-miR-3158-5p, hsa-miR-32-3p, hsa-miR-32-5p, hsa-miR-320a, hsa-miR-323a-3p, hsa-miR-323a-5p, hsa-miR-324-3p, hsa-miR-324-5p, hsa-miR-326, hsa-miR-328-3p, hsa-miR-328-5p, hsa-miR-329-3p, hsa-miR-329-5p, hsa-miR-330-3p, hsa-miR-330-5p, hsa-miR-331-3p, hsa-miR-331-5p, hsa-miR-335-3p, hsa-miR-335-5p, hsa-miR-337-3p, hsa-miR-337-5p, hsa-miR-338-3p, hsa-miR-338-5p, hsa-miR-339-3p, hsa-miR-339-5p, hsa-miR-33a-3p, hsa-miR-33a-5p, hsa-miR-33b-3p, hsa-miR-33b-5p, hsa-miR-340-3p, hsa-miR-340-5p, hsa-miR-342-3p, hsa-miR-342-5p, hsa-miR-345-3p, hsa-miR-345-5p, hsa-miR-34a-3p, hsa-miR-34a-5p, hsa-miR-34b-3p, hsa-miR-34b-5p, hsa-miR-34c-3p, hsa-miR-34c-5p, hsa-miR-3605-3p, hsa-miR-3605-5p, hsa-miR-361-3p, hsa-miR-361-5p, hsa-miR-3613-3p, hsa-miR-3613-5p, hsa-miR-3614-3p, hsa-miR-3614-5p, hsa-miR-362-3p, hsa-miR-362-5p, hsa-miR-363-3p, hsa-miR-363-5p, hsa-miR-365a-3p, hsa-miR-365a-5p, hsa-miR-365b-3p, hsa-miR-365b-5p, hsa-miR-369-3p, hsa-miR-369-5p, hsa-miR-370-3p, hsa-miR-370-5p, hsa-miR-374a-3p, hsa-miR-374a-5p, hsa-miR-374b-3p, hsa-miR-374b-5p, hsa-miR-375, hsa-miR-376a-2-5p, hsa-miR-376a-3p, hsa-miR-376a-5p, hsa-miR-376c-3p, hsa-miR-376c-5p, hsa-miR-377-3p, hsa-miR-377-5p, hsa-miR-378a-3p, hsa-miR-378a-5p, hsa-miR-379-3p, hsa-miR-379-5p, hsa-miR-381-3p, hsa-miR-381-5p, hsa-miR-382-3p, hsa-miR-382-5p, hsa-miR-409-3p, hsa-miR-409-5p, hsa-miR-411-3p, hsa-miR-411-5p, hsa-miR-412-3p, hsa-miR-421, hsa-miR-423-3p, hsa-miR-423-5p, hsa-miR-424-3p, hsa-miR-424-5p, hsa-miR-425-3p, hsa-miR-425-5p, hsa-miR-431-3p, hsa-miR-431-5p, hsa-miR-432-5p, hsa-miR-433-3p, hsamiR-433-5p, hsa-miR-449a, hsa-miR-449b-5p, hsa-miR-450a-1-3p, hsa-miR-450a-2-3p, hsa-miR-450a-5p, hsa-miR-450b-3p, hsa-miR-450b-5p, hsa-miR-451a, hsa-miR-452-3p, hsa-miR-4524a-3p, hsa-miR-4524a-5p, hsa-miR-4536-3p, hsa-miR-4536-5p, hsa-miR-454-3p, hsa-miR-454-5p, hsa-miR-4707-3p, hsa-miR-4707-5p, hsa-miR-4755-3p, hsa-miR-4755-5p, hsa-miR-4787-3p, hsa-miR-4787-5p, hsa-miR-483-3p, hsa-miR-483-5p, hsa-miR-484, hsa-miR-485-3p, hsa-miR-485-5p, hsa-miR-487b-3p, hsa-miR-487b-5p, hsa-miR-488-3p, hsa-miR-488-5p, hsa-miR-489-3p, hsa-miR-490-3p, hsa-miR-490-5p, hsa-miR-491-3p, hsa-miR-491-5p, hsa-miR-493-3p, hsa-miR-493-5p, hsa-miR-494-3p, hsa-miR-494-5p, hsa-miR-495-3p, hsa-miR-495-5p, hsa-miR-497-3p, hsa-miR-497-5p, hsa-miR-498, hsa-miR-5001-3p, hsa-miR-5001-5p, hsa-miR-500a-3p, hsa-miR-500a-5p, hsa-miR-5010-3p, hsa-miR-5010-5p, hsa-miR-503-3p, hsa-miR-503-5p, hsa-miR-504-3p, hsa-miR-504-5p, hsa-miR-505-3p, hsa-miR-505-5p, hsa-miR-506-3p, hsa-miR-506-5p, hsa-miR-508-3p, hsa-miR-508-5p, hsa-miR-509-3-5p, hsa-miR-509-3p, hsa-miR-509-5p, hsa-miR-510-3p, hsa-miR-510-5p, hsa-miR-512-5p, hsa-miR-513c-3p, hsa-miR-513c-5p, hsa-miR-514a-3p, hsa-miR-514a-5p, hsa-miR-514b-3p, hsa-miR-514b-5p, hsa-miR-516b-5p, hsa-miR-518c-3p, hsa-miR-518f-3p, hsa-miR-5196-3p, hsa-miR-5196-5p, hsa-miR-519a-3p, hsa-miR-519a-5p, hsa-miR-519c-3p, hsa-miR-519e-3p, hsa-miR-520c-3p, hsa-miR-520f-3p, hsa-miR-520g-3p, hsa-miR-520h, hsa-miR-522-3p, hsa-miR-525-5p, hsa-miR-526b-5p, hsa-miR-532-3p, hsa-miR-532-5p, hsa-miR-539-3p, hsa-miR-539-5p, hsa-miR-542-3p, hsa-miR-542-5p, hsa-miR-543, hsa-miR-545-3p, hsa-miR-545-5p, hsa-miR-548a-3p, hsa-miR-548a-5p, hsa-miR-548ar-3p, hsa-miR-548ar-5p, hsa-miR-548b-3p, hsa-miR-548d-3p, hsa-miR-548d-5p, hsa-miR-548e-3p, hsa-miR-548e-5p, hsa-miR-548h-3p, hsa-miR-548h-5p, hsa-miR-548j-3p, hsa-miR-548j-5p, hsa-miR-548o-3p, hsa-miR-548o-5p, hsa-miR-548v, hsa-miR-551b-3p, hsa-miR-551b-5p, hsa-miR-552-3p, hsa-miR-556-3p, hsa-miR-556-5p, hsa-miR-561-3p, hsa-miR-561-5p, hsa-miR-562, hsa-miR-567, hsa-miR-569, hsa-miR-570-3p, hsa-miR-570-5p, hsa-miR-571, hsa-miR-574-3p, hsa-miR-574-5p, hsa-miR-576-3p, hsa-miR-576-5p, hsa-miR-577, hsa-miR-579-3p, hsa-miR-579-5p, hsa-miR-582-3p, hsa-miR-582-5p, hsa-miR-584-3p, hsa-miR-584-5p, hsa-miR-589-3p, hsa-miR-589-5p, hsa-miR-590-3p, hsa-miR-590-5p, hsa-miR-595, hsa-miR-606, hsa-miR-607, hsa-miR-610, hsa-miR-615-3p, hsa-miR-615-5p, hsa-miR-616-3p, hsa-miR-616-5p, hsa-miR-617, hsa-miR-619-5p, hsa-miR-624-3p, hsa-miR-624-5p, hsa-miR-625-3p, hsa-miR-625-5p, hsa-miR-627-3p, hsa-miR-627-5p, hsa-miR-628-3p, hsa-miR-628-5p, hsa-miR-629-3p, hsa-miR-629-5p, hsa-miR-630, hsa-miR-633, hsa-miR-634, hsa-miR-635, hsa-miR-636, hsa-miR-640, hsa-miR-642a-3p, hsa-miR-642a-5p, hsa-miR-643, hsa-miR-645, hsa-miR-648, hsa-miR-6503-3p, hsa-miR-6503-5p, hsa-miR-651-3p, hsa-miR-651-5p, hsa-miR-6511a-3p, hsa-miR-6511a-5p, hsa-miR-652-3p, hsa-miR-652-5p, hsa-miR-653-5p, hsa-miR-654-3p, hsa-miR-654-5p, hsa-miR-657, hsa-miR-659-3p, hsa-miR-660-3p, hsa-miR-660-5p, hsa-miR-664b-3p, hsa-miR-664b-5p, hsa-miR-671-3p, hsa-miR-671-5p, hsa-miR-675-3p, hsa-miR-675-5p, hsa-miR-7-1-3p, hsa-miR-7-5p, hsa-miR-708-3p, hsa-miR-708-5p, hsa-miR-744-3p, hsa-miR-744-5p, hsa-miR-758-3p, hsa-miR-758-5p, hsa-miR-765, hsa-miR-766-3p, hsa-miR-766-5p, hsa-miR-767-3p, hsa-miR-767-5p, hsa-miR-769-3p, hsa-miR-769-5p, hsa-miR-802, hsa-miR-873-3p, hsa-miR-873-5p, hsa-miR-874-3p, hsa-miR-874-5p, hsa-miR-876-3p, hsa-miR-876-5p, hsa-miR-885-3p, hsa-miR-885-5p, hsa-miR-887-3p, hsa-miR-887-5p, hsa-miR-9-3p, hsa-miR-9-5p, hsa-miR-92a-1-5p, hsa-miR-92a-2-5p, hsa-miR-92a-3p, hsa-miR-92b-3p, hsa-miR-92b-5p, hsa-miR-93-3p, hsa-miR-93-5p, hsa-miR-941, hsa-miR-942-3p, hsa-miR-942-5p, hsa-miR-96-3p, hsa-miR-96-5p, hsa-miR-98-3p, hsa-miR-98-5p, hsa-miR-99a-3p, hsa-miR-99a-5p, hsa-miR-99b-3p, and hsa-miR-99b-5p.

In some embodiments, the cell state classifier of the present disclosure may be used in a bacterial cell. Though naturally-occurring bacterial cells lack true miRNAs (e.g., as described in Tjaden et al., Nucleic Acids Res. 34 (9): 2791-802), short non-coding RNA sequences have been identified in bacterial genome that broadly have comparable function as eukaryotic miRNAs. Such bacterial short non-coding RNAs function similarly as the miRNAs of the present disclosure and may be detected by the cell state classifier described herein.

For classifying a cell type (e.g., a cancer cell), one skilled in the art is familiar with the microRNAs that express specifically in such cell type but not in other cell types, and their respective nucleotide sequences. One skilled in the art is also familiar with the designing the target sites for the microRNA to be detected. Non-limiting, exemplary microRNA and respective target site sequences are provided in Table 1.

TABLE 1

Exemplary Synthetic microRNA and Target Sites

| microRNA Name | Nucleotide Sequence Encoding microRNA | SEQ ID NO: | Target Sequence | SEQ ID NO: |
|---|---|---|---|---|
| FF3 | TTTGTATTCAGCCCATATCG | 1 | AACGATATGGGCTGAATACAAA | 6 |
| FF4 | TTTAATTAAAGACTTCAAGCG | 2 | CCGCTTGAAGTCTTTAATTAAA | 7 |
| FF5 | TAATTGTCAAATCAGAGTGC | 3 | AAGCACTCTGATTTGACAATTA | 8 |
| FF6 | TTTATGAGGAATCTCTTTGG | 4 | AACCAAAGAGATTCCTCATAAA | 9 |
| T1 | TTCGAAGTATTCCGCGTACG | 5 | CACGTACGCGGAATACTTCGAA | 10 |

One or more (e.g., 1, 2, 3, 4, 5, 6, 7, 8, 9, 10, or more) target sites of the microRNAs to be detected by the cell state classifier are placed in each circuit (e.g., first or second sensor circuit, first or second signal circuit, etc.) in a non-coding region, e.g., upstream and/or downstream of the nucleotide sequence encoding the protein that is produced by the circuit (e.g., activator, repressor, or output molecule). Being "upstream" means the microRNA target sites are placed 5' of the nucleotide sequence encoding the protein that is produced by the circuit (e.g., activator, repressor, or output molecule). Being "downstream" means the microRNA target sites are placed 3' of the nucleotide sequence encoding the protein that is produced by the circuit (e.g., activator, repressor, or output molecule).

In some embodiments, one or more (e.g., 1, 2, 3, 4, 5, 6, 7, 8, 9, 10, or more) microRNA target sites are placed upstream of and is immediately adjacent to (no nucleotides in between) the nucleotide sequence encoding the protein that is produced by the circuit (e.g., activator, repressor, or output molecule). In some embodiments, one or more (e.g., 1, 2, 3, 4, 5, 6, 7, 8, 9, 10, or more) microRNA target sites are placed upstream of and is separated by a nucleotide spacer from the nucleotide sequence encoding the protein that is produced by the circuit (e.g., activator, repressor, or output molecule). In some embodiments, the nucleotide spacer may be 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used.

In some embodiments, one or more (e.g., 1, 2, 3, 4, 5, 6, 7, 8, 9, 10, or more) microRNA target sites are placed downstream of and is immediately adjacent to (no nucleotides in between) the nucleotide sequence encoding the protein that is produced by the circuit (e.g., activator, repressor, or output molecule). In some embodiments, one or more (e.g., 1, 2, 3, 4, 5, 6, 7, 8, 9, 10, or more) microRNA target sites are placed downstream of and is separated by a nucleotide spacer from the nucleotide sequence encoding the protein that is produced by the circuit (e.g., activator, repressor, or output molecule). In some embodiments, the nucleotide spacer may be 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used.

In some embodiments, one or more (e.g., 1, 2, 3, 4, 5, 6, 7, 8, 9, 10, or more) microRNA target sites are placed upstream and downstream of and is immediately adjacent (no nucleotides in between) to the nucleotide sequence encoding the protein that is produced by the circuit (e.g., activator, repressor, or output molecule). In some embodiments, one or more (e.g., 1, 2, 3, 4, 5, 6, 7, 8, 9, 10, or more) microRNA target sites are placed upstream and downstream of and is separated by a nucleotide spacer from the nucleotide sequence encoding the protein that is produced by the circuit (e.g., activator, repressor, or output molecule). In some embodiments, the nucleotide spacer may be 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used. In some embodiments, placing multiple microRNA target sites at different locations of each circuit strengthens (e.g., by at least 30%) the inhibitory effect of the microRNA on the product of the circuit. When multiple microRNA target sites are used, there may be a nucleotide spacer (e.g., a nucleotide spacer of 1, 2, 3, 4, 5, 6, 7, 8, 9, or 10 nucleotides long), or no space between each target site.

An "activator," as used herein, refers to a transcriptional activator. The terms "activator" or "transcriptional activator" are used interchangeably herein. A transcriptional activator is a protein that increases gene transcription of a gene or set of genes. Most activators function by binding sequence-specifically to a DNA site located in or near a promoter and making protein-protein interactions with the general transcription machinery (RNA polymerase and general transcription factors), thereby facilitating the binding of the general transcription machinery to the promoter.

A "repressor," as used herein, refers to a transcriptional repressor. The terms "repressor" or "transcriptional repressor" are used interchangeably herein. A transcriptional repressor is a DNA- or RNA-binding protein that inhibits the expression of one or more genes by binding to the operator or associated silencers. A DNA-binding repressor blocks the attachment of RNA polymerase to the promoter, thus preventing transcription of the genes into messenger RNA. An RNA-binding repressor binds to the mRNA and prevents translation of the mRNA into protein.

The expression of the activators and repressors of the present disclosure are activated or repressed in response to other elements of the cell state classifier (i.e., the presence or absence of microRNA, or the presence or absence of another activator or repressor). The activators and repressors, once expressed, can activate or repress the expression of other elements in the cell state classifier (e.g., an output molecule).

Herein, the expression of a gene is considered to be "activated" by an activator if the expression of the genes is at least 20% higher in the presence of the activator, compared to without the activator. For example, the expression of a gene is considered to be activated by an activator if the expression of the genes is at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or higher in the presence of the activator, compared to without the activator. In some embodiments, the expression of a gene is considered to be activated by an activator if the expression of the genes is 20%, 30%, 40%, 50%, 60%, 70%, 80%, 90%, 100%, 2-fold, 5-fold, 10-fold, 100-fold, 1000-fold, or higher in the presence of the activator, compared to without the activator.

Conversely, the expression of a gene is considered to be "repressed" by a repressor if the expression of the gene is at least 20% lower in the presence of the repressor, compared to without the repressor. For example, the expression of a gene is considered to be repressed by a repressor if the expression of the genes is at least 20%, at least 30%, at least 40%, at least 50%, at least 60%, at least 70%, at least 80%, at least 90%, at least 95%, at least 99% or lower in the presence of the repressor, compared to without the repressor. In some embodiments, the expression of a gene is considered to be repressed by a repressor if the expression of the genes is 20%, 30%, 40%, 50%, 60%, 70%, 80%, 90%, 95%, 99%, or even 100% in the presence of the repressor, compared to without the repressor.

One skilled in the art is able to choose the transcriptional activators or repressors for use in accordance with the present disclosure. Public databases are available for known or predicted transcriptional regulators, e.g., transcriptionfactor.org.

An "output molecule," as used herein, refers to a signal produced by the cell state classifier after detecting the microRNA profile (e.g., a matching microRNA profile). The cell state classifier of the present disclosure is designed such that the output molecule is expressed when a matching microRNA profile is detected. In some embodiments, the output molecule has a basal expression level and the expression level increases (e.g., by at least 20%) when a matching microRNA profile is detected, compared to when a non-matching microRNA profile is detected. For example, the expression level of the output molecule may be at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or higher when a matching microRNA profile is detected, compared to when a non-matching microRNA profile is detected. In some embodiments, the expression level of the output molecule is 20%, 30%, 40%, 50%, 60%, 70%, 80%, 90%, 100%, 2-fold, 5-fold, 10-fold, 100-fold, 1000-fold, or higher when a matching microRNA profile is detected, compared to when a non-matching microRNA profile is detected.

The output molecule, in some embodiments, is a detectable protein. In some embodiments, a detectable protein is a fluorescent protein. A fluorescent protein is a protein that emits a fluorescent light when exposed to a light source at an appropriate wavelength (e.g., light in the blue or ultraviolet range). Suitable fluorescent proteins that may be used in accordance with the present disclosure include, without limitation, eGFP, eYFP, eCFP, mKate2, mCherry, mPlum, mGrape2, mRaspberry, mGrape1, mStrawberry, mTangerine, mBanana, and mHoneydew. In some embodiments, a detectable protein is an enzyme that hydrolyzes an substrate to produce a detectable signal (e.g., a chemiluminescent signal). Such enzymes include, without limitation, beta-galactosidase (encoded by LacZ), horseradish peroxidase, or luciferase. In some embodiments, the output molecule is a fluorescent RNA. A fluorescent RNA is an RNA aptamer that emits a fluorescent light when bound to a fluorophore and exposed to a light source at an appropriate wavelength (e.g., light in the blue or ultraviolet range). Suitable fluorescent RNAs that may be used as an output molecule in the sensor circuit of the present disclosure include, without limitation, Spinach and Broccoli (e.g., as described in Paige et al., Science Vol. 333, Issue 6042, pp. 642-646, 2011, incorporated herein by reference).

In some embodiments, the output molecule is a therapeutic molecule. A "therapeutic molecule" is a molecule that has therapeutic effects on a disease or condition, and may be used to treat a diseases or condition. Therapeutic molecules of the present disclosure may be nucleic acid-based or protein or polypeptide-based.

In some embodiments, nucleic acid-based therapeutic molecule may be an RNA interference (RNAi) molecule (e.g., a microRNA, siRNA, or shRNA) or an nucleic acid enzyme (e.g., a ribozyme). RNAi molecules and there use in silencing gene expression are familiar to those skilled in the art. In some embodiments, the RNAi molecule targets an oncogene. An oncogene is a gene that in certain circumstances can transform a cell into a tumor cell. An oncogene may be a gene encoding a growth factor or mitogen (e.g., c-Sis), a receptor tyrosine kinase (e.g., EGFR, PDGFR, VEGFR, or HER2/neu), a cytoplasmic tyrosine kinase (e.g., Src family kinases, Syk-ZAP-70 family kinases, or BTK family kinases), a cytoplasmic serine/threonine kinase or their regulatory subunits (e.g., Raf kinase or cyclin-dependent kinase), a regulatory GTPase (e.g., Ras), or a transcription factor (e.g., Myc). In some embodiments, the oligonucleotide targets Lipocalin (Lcn2) (e.g., a Lcn2 siRNA). One skilled in the art is familiar with genes that may be targeted for the treatment of cancer.

Non-limiting examples of protein or polypeptide-based therapeutic molecules include enzymes, regulatory proteins (e.g., immuno-regulatory proteins), antigens, antibodies or antibody fragments, and structural proteins. In some embodiments, the protein or polypeptide-based therapeutic molecules are for cancer therapy.

Suitable enzymes (for operably linking to a synthetic promoter) for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase,), esterases (e.g. sterol esterase), disaccharidases (e.g., sucrase, lactase, beta-galactosidase, maltase, isomaltase), DNases, and RNases.

Non-limiting examples of antibodies and fragments thereof include: bevacizumab (AVASTIN®), trastuzumab (HERCEPTIN®), alemtuzumab (CAMPATH®, indicated for B cell chronic lymphocytic leukemia,), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-05, IOR-T6 (anti-CD1), IOR EGF/R3, celogovab (ONCOSCINT® OV103), epratuzumab (LYMPHOCIDE®), pemtumomab (THERAGYN®), Gliomab-H (indicated for brain cancer, melanoma). In some embodiments, the antibody is an antibody that inhibits an immune check point protein, e.g., an anti-PD-1 antibody such as pembrolizumab (Keytruda®) or nivolumab (Opdivo®), or an anti-CTLA-4 antibody such as ipilimumab (Yervoy®). Other antibodies and antibody fragments may be operably linked to a synthetic promoter, as provided herein.

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1. Other transcription factors may be operably linked to a synthetic promoter, as provided herein.

As used herein, an immunoregulatory protein is a protein that regulates an immune response. Non-limiting examples of immunoregulatory include: antigens, adjuvants (e.g., flagellin, muramyl dipeptide), cytokines including interleukins (e.g., IL-2, IL-7, IL-15 or superagonist/mutant forms of these cytokines), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunoregulatory proteins may be operably linked to a synthetic promoter, as provided herein.

As used herein, an antigen is a molecule or part of a molecule that is bound by the antigen-binding site of an antibody. In some embodiments, an antigen is a molecule or moiety that, when administered to or expression in the cells of a subject, activates or increases the production of antibodies that specifically bind the antigen. Antigens of pathogens are well known to those of skill in the art and include, but are not limited to parts (coats, capsules, cell walls, flagella, fimbriae, and toxins) of bacteria, viruses, and other microorganisms. Examples of antigens that may be used in accordance with the disclosure include, without limitation, cancer antigens, self-antigens, microbial antigens, allergens and environmental antigens. Other antigens may be operably linked to a synthetic promoter, as provided herein.

In some embodiments, the antigen of the present disclosure is a cancer antigen. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-05. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, CD20 and c-erbB-2. Other cancer antigens may be operably linked to a synthetic promoter, as provided herein.

In some embodiments, a protein or polypeptide-based therapeutic molecule is a fusion protein. A fusion protein is a protein comprising two heterologous proteins, protein domains, or protein fragments, that are covalently bound to each other, either directly or indirectly (e.g., via a linker), via a peptide bond. In some embodiments, a fusion protein is encoded by a nucleic acid comprising the coding region of a protein in frame with a coding region of an additional protein, without intervening stop codon, thus resulting in the translation of a single protein in which the proteins are fused together.

Figure 3:
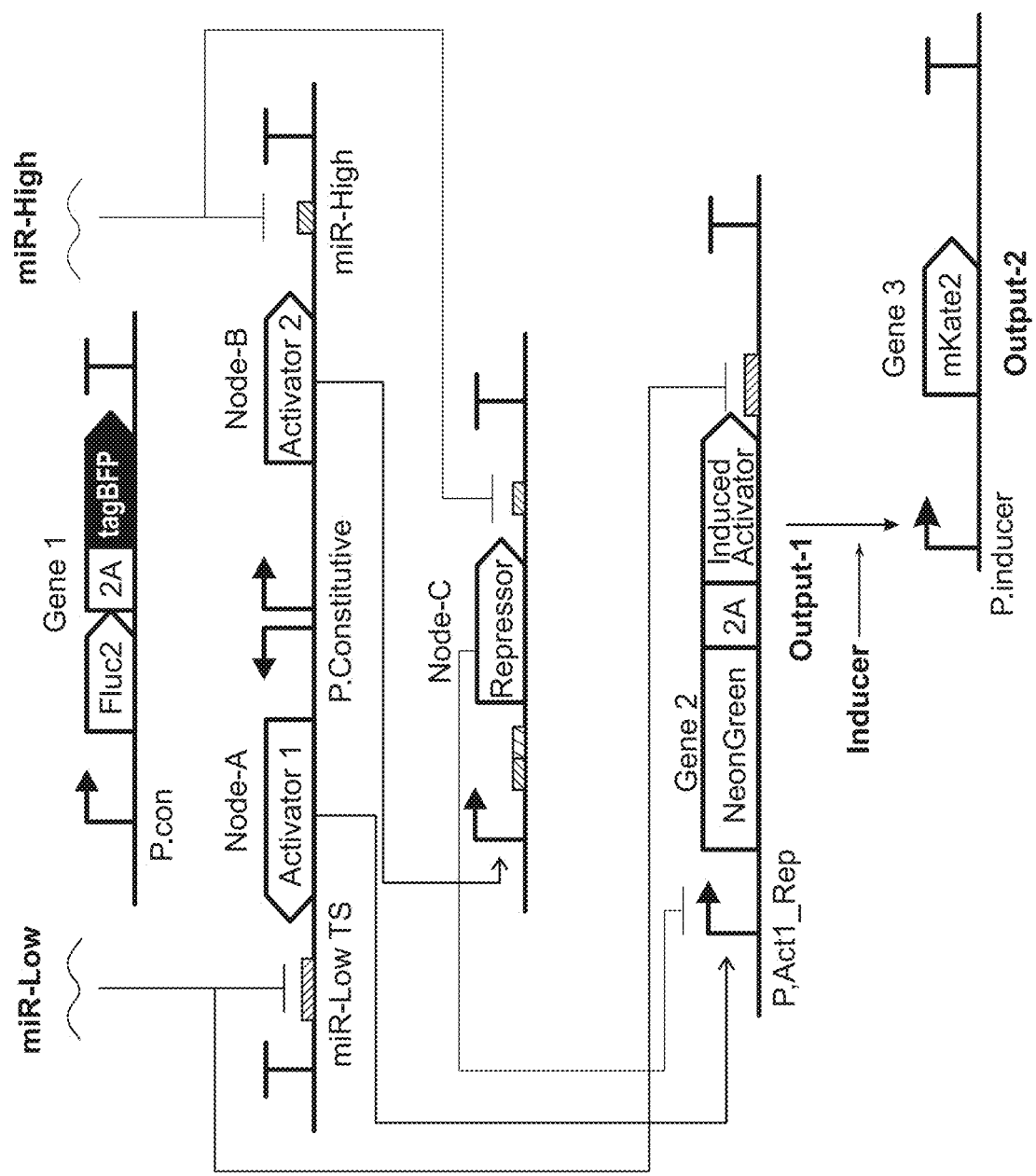
FIG. 3: Diagram of a two-step cell classifier. Output-2 is added to the design described in FIG. 2, such that the presence of both Output-1 and an inducer is required to activate Output-2. Output-2 is controlled by activation of a classifier and external inducer. To achieve this, the Induced Activator is co-expressed with Output-1's NeonGreen and activates Output2 promoter when an inducer is present. A non-limiting example of an Induced Activator and its cognate inducer is rtTA and Dox, respectively.

In some embodiments, one or more output molecules are produced by the cell state classifier (e.g., the first or second signal circuit). As such, the first and/or second signal circuit comprises a nucleotide sequence encoding one or more output molecules. In some embodiments, the nucleotide sequence encoding different output molecules are linked by linkers. In some embodiments. In some embodiments, the linker is a nucleotide sequence encoding a self-cleaving peptide (e.g., the 2A tag). As such, the one or more output molecules are translated as one signal polypeptide and the self-cleaving linker is cleaved after translation, producing two individual output molecules. One skilled in the art is familiar with such self-cleaving peptides and methods of using them (e.g., as described in Kim et al., PLoS ONE 6(4): e18556, incorporated herein by reference). In some embodiments, the output molecule comprises a detectable protein and a therapeutic molecule. In some embodiments, the output molecule comprises a detectable protein and an induced activator (e.g., "output-1" in FIG. 3).

An induced activator is a transcriptional activator that activates the expression of a gene in the presence of an inducer. In some embodiments, the third activator of the cell state classifier described herein is an induced activator. An "inducer" is a molecule that regulates gene expression by binding to repressors or activators. In some embodiments, inducers function by binding and disabling repressors. The binding of the inducer to the repressor prevents the repressor from binding to the operator. RNA polymerase can then begin to transcribe operon genes. In some embodiments, inducers function by binding to activators (e.g., an induced activator). An induced activator binds to an inducer and the complex binds to the activation sequence and activates one or more target genes. Removing the inducer stops transcription. In some embodiments, the induced activator and the inducer may be selected from "chemically-inducible dimerization (CID)" systems (e.g., as described in DeRose et al., *Pflugers Arch.* 465(3): 409-417, 2013, incorporated herein by reference), or "chemically-induced proximity (CIP)" systems (e.g., as described in Liang et al., *Sci Signal.* 15; 4(164):rs2, 2011, incorporated herein by reference). For example, the plant hormone S-(+)-abscisic acid (ABA) induces the dimerization of its binding proteins PYLI or ABI. As such, fusion of ABI to DNA binding domain (e.g., LmrA) results an induced activator as described herein, whose transcriptional activation activity depends on the presence of the inducer ABA. Any known protein-inducer pairs of the CID system may be used herein. In some embodiments, the induced activator is PhlF-ABI, LmrA-ABI, ABI-PhlF, ABI-LmrA, NLS-PhlF-ABI, NLS-LmrA-ABI, NLS-ABI-PhlF, NLS-ABI-LmrA, PhlF-ABI-NLS, LmrA-ABI-NLS, ABI-PhlF-NLS, ABI-LmrA-NLS, and the inducer is abscisic acid (ABA).

A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof. A promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter. In some embodiments, using inducible promoters in the genetic circuits of the cell state classifier results in the conditional expression or a "delayed" expression of a gene product.

The administration or removal of an inducer signal results in a switch between activation and inactivation of the transcription of the operably linked nucleic acid sequence. Thus, the active state of a promoter operably linked to a nucleic acid sequence refers to the state when the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, an inducer signal of the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters.

In some embodiments, an inducer signal of the present disclosure is anhydrotetracycline (aTc), which is a derivative of tetracycline that exhibits no antibiotic activity and is designed for use with tetracycline-controlled gene expression systems, for example, in bacteria.

In some embodiments, an inducer signal of the present disclosure is isopropyl β-D-1-thiogalactopyranoside (IPTG), which is a molecular mimic of allolactose, a lactose metabolite that triggers transcription of the lac operon, and it is therefore used to induce protein expression where the gene is under the control of the lac operator. IPTG binds to the lac repressor and releases the tetrameric repressor from the lac operator in an allosteric manner, thereby allowing the transcription of genes in the lac operon, such as the gene coding for beta-galactosidase, a hydrolase enzyme that catalyzes the hydrolysis of β-galactosides into monosaccharides. The sulfur (S) atom creates a chemical bond which is non-hydrolyzable by the cell, preventing the cell from metabolizing or degrading the inducer. IPTG is an effective inducer of protein expression, for example, in the concentration range of 100 μM to 1.0 mM. Concentration used depends on the strength of induction required, as well as the genotype of cells or plasmid used. If lacIq, a mutant that over-produces the lac repressor, is present, then a higher concentration of IPTG may be necessary. In blue-white screen, IPTG is used together with X-gal. Blue-white screen allows colonies that have been transformed with the recombinant plasmid rather than a non-recombinant one to be identified in cloning experiments.

Other inducible promoter systems are known in the art and may be used in accordance with the present disclosure.

In some embodiments, inducible promoters of the present disclosure are from prokaryotic cells (e.g., bacterial cells). Examples of inducible promoters for use prokaryotic cells include, without limitation, bacteriophage promoters (e.g. Pls1con, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated *E. coli* promoters such as positively regulated σ70 promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rhl), Pu, FecA, pRE, cadC, hns, pLas, pLux), σS promoters (e.g., Pdps), σ32 promoters (e.g., heat shock) and σ54 promoters (e.g., glnAp2); negatively regulated *E. coli* promoters such as negatively regulated σ70 promoters (e.g., Promoter (PRM+), modified lamdba Prm promoter, TetR-TetR-4C P(Las) TetO, P(Las) CIO, P(Lac) IQ, RecA_DlexO_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/c1, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), σS promoters (e.g., Lutz-Bujard LacO with alternative sigma factor σ38), σ32 promoters (e.g., Lutz-Bujard LacO with alternative sigma factor σ32), and σ54 promoters (e.g., glnAp2); negatively regulated $B.$ $subtilis$ promoters such as repressible $B.$ $subtilis$ GA promoters (e.g., Gram-positive IPTG-inducible, Xyl, hyper-spank) and GB promoters. Other inducible microbial promoters may be used in accordance with the present disclosure.

Figure 8:
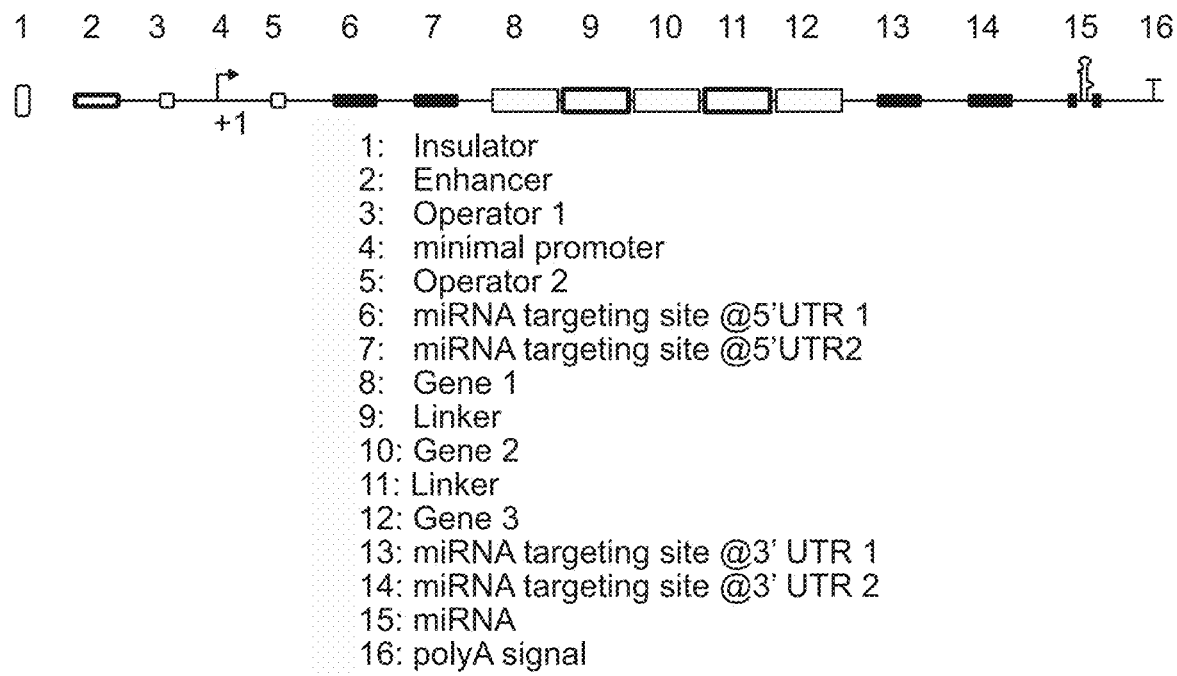
FIG. 8: Genetic elements in each genetic circuit of the cell state classifier.

In some embodiments, each of the genetic circuits of the cell state classifier comprises additional genetic elements (e.g., as shown in FIG. 8). In some embodiments, the first sensor circuit further comprises an insulator, an enhancer, one or more operators, a nucleotide sequence encoding one or more output molecules operably linked to the promoter of the first sensor circuit, a nucleotide sequence encoding a microRNA, and/or a polyadenylation signal.

In some embodiments, the first part of the second sensor circuit further comprises an insulator, an enhancer, one or more operators, a nucleotide sequence encoding one or more output molecules operably linked to the promoter of the first part of the second sensor circuit, a nucleotide sequence encoding a microRNA, and/or a polyadenylation signal. In some embodiments, the second part of the second sensor circuit further comprises an insulator, an enhancer, one or more operators, a nucleotide sequence encoding one or more output molecules operably linked to the promoter of the second part of the second sensor circuit, a nucleotide sequence encoding a microRNA, and/or a polyadenylation signal.

In some embodiments, the first signal circuit further comprises an insulator, an enhancer, one or more operators, a nucleotide sequence encoding one or more output molecules operably linked to the promoter of the first signal circuit, a nucleotide sequence encoding a microRNA, and/or a polyadenylation signal. In some embodiments, the second signal circuit further comprises an insulator, an enhancer, one or more operators, a nucleotide sequence encoding one or more output molecules operably linked to the promoter of the second signal circuit, a nucleotide sequence encoding a microRNA, and/or a polyadenylation signal.

In some embodiments, the regulatory circuit further comprises an insulator, an enhancer, one or more operators, a nucleotide sequence encoding one or more output molecules operably linked to the promoter of the regulator circuit, a nucleotide sequence encoding a microRNA, and/or a polyadenylation signal. In some embodiments, the control circuit further comprises an insulator, an enhancer, one or more operators, a nucleotide sequence encoding one or more output molecules operably linked to the promoter of, a nucleotide sequence encoding a microRNA, and/or a polyadenylation signal.

A "genomic insulator" refers to a class of DNA sequence elements that possess a common ability to protect genes from inappropriate signals (e.g., enhancing signal or repression signal) emanating from their surrounding environment, i.e., establishing boundaries for gene expression. In some embodiments, a genomic insulator has one or more proteins associated with the DNA sequence elements when exerting its function (e.g., as described in Yang et al., $Adv$ $Cancer$ $Res.$ 2011; 110: 43-76; and in West et al., $Genes$ $&$ $Development$ 16:271-288, 2002, incorporated herein by reference). Certain genomic insulators, e.g., chicken HS4 insulator (cHS4) have been shown to enhance the expression of a transgene integrated into the chromosome by a retroviral vector (e.g., as described in Revilla et al., $J.$ $Virol.$ May 2000 vol. 74 no. 10 4679-4687, incorporated herein by reference). Genomic insulators that may be used in accordance with the present disclosure may be from different organisms, e.g., $Saccharomyces$ $cerevisiae,$ $Drosophila$ $melanogaster$, or a vertebrate such as a chicken or a mammal. In some embodiments, the mammal is human. Non-limiting, exemplary genomic insulators that may be used in accordance with the present disclosure are listed in Table 2. In some embodiments, the genomic insulator is a cHS4 insulator.

TABLE 2

Genomic Insulators (adapted from West et al., *Genes & Development* 16: 271-288, 2002, incorporated herein by reference)

| Genomic Insulator | Enhancer Blocking (E) or Barrier (B) Activities | In situ Function | Associated Proteins |
|---|---|---|---|
| *Saccharamyces cerevisiae* HMR tRNA$^{Thr}$ | B | Shown to restrict the spread of Sir-mediated-silencing from HMR silencers | RNAP III complex, Smc1, Smc3, and Med1 cohesins |
| Cha1 UAS | B | Proposed to overcome Sir-mediated silencing from the HML1 silencer following serine induction | Cha4 |
| UAS$_{rpg}$ | B | Found in the promoters of many ribosomal protein genes, may restrict silencing to specific domains | Rap1 |

TABLE 2-continued

Genomic Insulators (adapted from West et al., *Genes & Development* 16: 271-288, 2002, incorporated herein by reference)

| Genomic Insulator | Enhancer Blocking (E) or Barrier (B) Activities | In situ Function | Associated Proteins |
|---|---|---|---|
| STAR | B | Located between the X and Y subtelomeric repeat, shown to constrain telomeric silencing to limited areas | Tbfl, Reb1 |
| *Drosophila melanogaster* scs scs' | E | Putative boundary elements flanking the 87A7 hsp70 locus | Zw5, BEAF |
| gypsy | E | Retrotransposable element | su(Hw), mod(mdg4) |
| Fab-7, Fab-8 | E | Maintain the functional independence of the lab-7 enhancer at the abdominal-B locus | Unknown |
| fa$^{swb}$ | E | Chromosomal interband between 3C6 and 3C7, Protects the Notch gene against position effect | Unknown |
| eve promoter | E | Proposed to facilitate activation by distant enhancers | (GAGA) |
| *Parancentrotus lividus* sns | E | Proposed to define the downstream boundary of the H2A modulator enhancer | Unknown |
| *Hemicentrotus pulcherrimus* UR1 | E B | Located upstream of Ars gene, proposed to shield upstream genes from the arylsulfatase C15 enhancer | Unknown |
| *Xenopus laevis* RO | E | Proposed to restrict the action of 60/81 enhancers to create single 40S rRNA gene expression units | CTCF |
| *Gallus* Lys 5' A | E B | The 5' boundary of the lysozyme gene domain in macrophages, associates with nuclear matrix preparations | Unknown CTCF |
| HS4 | E B | Proposed to prevent cross-talk between the β-globin LCR and upstream folate receptor gene enhancers Proposed to prevent silencing of the β-globin genes from an upstream region of condensed chromatin | CTCF Unknown |
| 3'HS | E | Proposed to prevent cross-talk between the β-globin LCR and downstream olfactory receptor gene enhancers | CTCF |
| *Mus musculus* BEAD-1 | E | Proposed to separate the TCR α/β locus into distinct regulatory domains controlled by the Eδ and TCR α enhancers | CTCF |
| HS2-6 | E | Proposed to separate the regulatory domains of the TCR α genes and the ubiquitous antiapopstosis Dadl loci | Unknown |
| DMD/ICR | E | Located between the reciprocally imprinted Igf2 and H19 genes, shown to block the access of Igf2 to downstream endodermal enhancers on the maternally inherited allele | CTCF (sensitive to CpG methylation) |
| *Homo sapiens* 5'HS5 | E | Located upstream of β globin locus control region, may limit the action of the LCR to the downstream globin genes | Unknown |

TABLE 2-continued

Genomic Insulators (adapted from West et al., *Genes & Development* 16: 271-288, 2002, incorporated herein by reference)

| Genomic Insulator | Enhancer Blocking (E) or Barrier (B) Activities | In situ Function | Associated Proteins |
|---|---|---|---|
| DMD/ICR | E | (See mouse DMD/ICR above) | |
| apoB (−57 kb) | E | Proposed to form the 5' boundary of the apolipoprotein 8 chromatin domain in intestinal tissues | CTCF |
| apoB (+43 kb) | B | Proposed to form the 3' boundary of the apolipoprotein B chromatin domain | Unknown |
| DM1 | E | Located between the DMPK and SIX5 genes, proposed to block access of the DMPK gene to the SIX5 enhancer | CTCF (sensitive to CpG methylation) |

In some embodiments, one or more genomic insulators may be used in the genetic circuits of the present disclosure. For example, 1, 2, 3, 4, 5, 6, 7, 8, 9, 10 or more genomic insulators may be used. In some in embodiments, each genomic insulator may be linked with another genomic insulator by a oligonucleotide linker, e.g., a linker of 3-10 nucleotides long. One skilled in the art is familiar with oligonucleotide sequences that may be used as linkers.

An "enhancer," as used herein, refers to a transcriptional enhancer. The terms "enhancer" and "transcriptional enhancer" are used interchangeably herein. An enhancer is a short (50-1500 bp) region of DNA that can be bound by activators to increase the likelihood that transcription of a particular gene will occur. Enhancers are cis-acting and can be located up to 1 Mbp (1,000,000 bp) away from the gene, upstream or downstream from the transcription start site. Enhancers are found both in prokaryotes and eukaryotes. There are hundreds of thousands of enhancers in the human genome.

An "operator," as used herein, refers to a segment of DNA to which a repressor binds to regulate gene expression by repressing it. In the lac operon, an operator is defined as a segment between the promoter and the genes of the operon. When bound by a repressor, the repressor protein physically obstructs the RNA polymerase from transcribing the genes, thus repressing transcription of the gene.

A "polyadenylation signal," as used herein, refers to a sequence motif recognized by the RNA cleavage complex that cleaves the 3'-most part of a newly produced RNA and polyadenylates the end produced by this cleavage. The sequence of the polyadenylation signal varies between groups of eukaryotes. Most human polyadenylation sites contain the AAUAAA sequence.

A transcriptional terminator typically occurs after a polyadenylation signal in any of the genetic circuit of the present disclosure. A "transcriptional terminator" is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, inclusion in the various nucleic acid constructs and circuits described herein of a terminator that ends the production of an RNA transcript is contemplated. A terminator may be necessary in vivo to achieve desirable output expression levels (e.g., low output levels) or to avoid transcription of certain sequences.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only.

In prokaryotic systems, terminators usually fall into two categories (1) rho-independent terminators and (2) rho-dependent terminators. Rho-independent terminators are generally composed of palindromic sequence that forms a stem loop rich in G-C base pairs followed by several T bases. Without wishing to be bound by theory, the conventional model of transcriptional termination is that the stem loop causes RNA polymerase to pause, and transcription of the poly-A tail causes the RNA:DNA duplex to unwind and dissociate from RNA polymerase.

In eukaryotic systems, the terminator region may comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in some embodiments involving eukaryotes, a terminator may comprise a signal for the cleavage of the RNA. In some embodiments, the terminator signal promotes polyadenylation of the message. The terminator and/or polyadenylation site elements may serve to enhance output nucleic acid levels and/or to minimize read through between nucleic acids.

Terminators for use in accordance with the present disclosure include any terminator of transcription described herein or known to one of ordinary skill in the art. Examples of terminators include, without limitation, the termination sequences of genes such as, for example, the bovine growth hormone terminator, and viral termination sequences such as, for example, the SV40 terminator, spy, yejM, secG-leuU, thrLABC, rrnB T1, hisLGDCBHAFI, metZWV, rrnC, xapR, aspA and arcA terminator. In some embodiments, the termination signal may be a sequence that cannot be transcribed or translated, such as those resulting from a sequence truncation.

Non-limiting examples of each genetic element in each genetic circuit of the cell state classifier shown in FIG. 8 are provided in Table 3.

TABLE 3

Genetic Elements

| Genetic Elements | Genetic Circuits | | | | |
|---|---|---|---|---|---|
| | First sensor circuit | First part of second sensor circuit | Second part of second sensor circuit | First signal circuit | Second signal circuit |
| 1: Insulator | null, cHS4x2, A2, E1, E4, F1, D1 | null, cHS4x2, A2, E1, E4, F1, D1 | null, cHS4x2, A2, E1, E4, F1, D1 | cHS4x2, A2, E1, E4, F1, D1 | cHS4x2, A2, E1, E4, F1, D1 |
| 2: Enhancer | CMV, SV40, hEF1a | null, CMV, SV40, hEF1a, | CMV, SV40, hEF1a, 1xtetO, 2XtetO, 3xtetO, 4XtetO, 5xtetO, 6XtetO, 7xtetO | 1xUAS, 2xUAS, 3xUAS, 4xUAS, 5xUAS, 6xUAS, 7xUAS, 8xUAS, 9xUAS, 10xUAS | 1xPhlF, 2xPhlF, 3xPhlF, 4xPhlF, 5xPhlF, 6xPhlF, 7xPhlF, 8xPhlF, 9xPhlF, 10xPhlF, 1xLmrA, 2xLmrA, 3xLmrA, 4xLmrA, 5xLmrA, 6xLmrA, 7xLmrA, 8xLmrA, 9xLmrA, 10xLmrA |
| 3: Operator | null, 1xBM3R1, 2xBM3R1, 3xBM3R2, 4xBM3R2 | null, 1xLmrA, 2xLmrA, 3xLmrA, 4xLmrA, 1xPhlF, 2xPhlF, 3xPhlF, 4xPhlF | null, 1xLmrA, 2xLmrA, 3xLmrA, 4xLmrA, 1xPhlF, 2xPhlF, 3xPhlF, 4xPhlF | null (2), 1xBM3R1, 2xBM3R1, 3xBM3R2, 4xBM3R2, 1xT14, 2xT14, 3xT14, 4xT14 | null, 1xBM3R1, 2xBM3R1, 3xBM3R2, 4xBM3R2, 1xT14, 2xT14, 3xT14, 4xT14, 1xBM3R1_1xLacO, 1xBM3R1_2xLacO, 1xBM3R1_3xLacO, 1xBM3R1_4xLacO, similarly for 2xBM3R1, 3xBM3R2, 4xBM3R2, 1xT14, 2xT14, 3xT14, 4xT14, . . . total 41 possible combination |
| 4: Minimal promoter | minCMV1, minCMV2, minCMV3, minCMV3, minCMV5, minCMV6, minKobi, minhEF1a | null, minCMV1, minCMV2, minCMV3, minCMV4, minCMV5, minCMV6, minKobi, minhEF1a, | minCMV1, minCMV2, minCMV3, minCMV4, minCMV5, minCMV6, minKobi, minhEF1a | minCMV1, minCMV2, minCMV3, minCMV4, minCMV5, minCMV6, minKobi, minhEF1a | minCMV1, minCMV2, minCMV3, minCMV4, minCMV5, minCMV6, minKobi, minhEF1a |
| 5: Operator 2 | null, 1xBM3R1, 2xBM3R1, 3xBM3R2, 4xBM3R2, | null, 1xLmrA, 2xLmrA, 3xLmrA, 4xLmrA, 1xPhlF, 2xPhlF, 3xPhlF, 4xPhlF, | null, 1xLmrA, 2xLmrA, 3xLmrA, 4xLmrA, 1xPhlF, 2xPhlF, 3xPhlF, 4xPhlF, | null, 1xBM3R1 (2), 2xBM3R1, 3xBM3R2, 4xBM3R2, 1xBM3R1_2xKT, 2xBM3R1_2xKT, 3xBM3R1_2xKT, 4xBM3R1_2xKT, 1xT14, 2xT14, 3xT14, 4xT14, 1xT14_2xKT, 2xT14_2xKT, 3xT14_2xKT, 4xT14_2xKT | null, 1xBM3R1, 2xBM3R1, 3xBM3R2, 4xBM3R2, 1xBM3R1_2xKT, 2xBM3R1_2xKT, 3xBM3R1_2xKT, 4xBM3R1_2xKT, 1xT14, 2xT14, 3xT14, 4xT14, 1xT14_2xKT, 2xT14_2xKT, 3xT14_2xKT, 4xT14_2xKT, similarly add 1-4xLacO . . . total 65 possible combination |
| 6: microRNA targeting site at 5'UTR 1 | null, 1x 122a, 1x 199a, 1x 138, 2x 122a, 2x 199a, 2x 138, 3x 122a, 3x 199a, 3x 138, 4x 122a, 4x 199a, 4x 138, 1x | null(3), 1x 21, 2x 21(2), 3x 21, 4x 21, | null (3), 1x 21, 2x 21(2), 3x 21, 4x 21 | null, 1x 122a, 1x 199a, 1x 138, 2x 122a, 2x 199a, 2x 138, 3x 122a, 3x 199a, 3x 138, 4x 122a, 4x 199a, 4x 138, | null, 1x 122a, 1x 199a, 1x 138, 2x 122a, 2x 199a, 2x 138, 3x 122a, 3x 199a, 3x 138, 4x 122a, 4x 199a, 4x 138, |

TABLE 3-continued

| | | Genetic Elements | | | |
|---|---|---|---|---|---|
| | 122a_1X199a, ... total 126 possible combination | | | 1x 122a_1X199a, 4x122a_4x199a_4x138 ... total 126 possible combination | 1x 122a_1X199a, 4x122a_4x199a_4x138 ... total 126 possible combination |
| 7: microRNA targeting site at 5'UTR 2 | null | null, 1x FF5, 2x FF5, 3x FF5, 4x FF5 | null, 1x FF5, 2x FF5, 3x FF5, 4x FF5 | null | null |
| 8: Gene 1 | VP16GAL4, NLS-VP16GAL4, PEST1-VP16GAL4, PEST2-VP16GAL4, NLS-PEST1-VP16GAL4, NLS-PEST2-VP16GAL4, PEST1-NLS-VP16GAL4, PEST2-NLS-VP16GAL4, VP16GAL4-NLS, VP16GAL4-PEST1, VP16GAL4-PEST2, VP16GAL4-PEST1-NLS, VP16GAL4-PEST2-NLS, VP16GAL4-NLS-PEST1, VP16GAL4-NLS-PEST2, similarly for GAL4VP16, GAL4VP64, GAL4VP65, GAL4Rta, GAL4VPR, VP64GAL4, P65GAL4, RtaGAL4, VPRGAL4, above with and without codon optimization ... total 300 possible combination | similarly for rtTA, rtTA3, Tet3G, tTA, tTAadv, codon optimized tTAadv, above with and without codon optimization ... total 150 possible combination | similarly for BM3R1, TALER14, codon optimized BM3R1-NLS, above with and without codon optimization ... total 60 possible combination | mNeonGreen | mKate2 |
| 9: Linker | null | null | null, GSGSG, P2A, T2A, E2A, F2A | GSGSG, P2A, T2A, E2A, F2A | null |
| 10: Gene 2 | null | null | null, similarly for, L7Ae, ... total 15 possible combination | similarly for, VP16PYL1, VP64PYL1, P65PYL1, RtaPYL1, VPRPYL1, PYL1VP16, PYL1VP64, PYL1P65, PYL1Rta, PYL1VPR, NLS-VP16PYL1(3), codon optimized NLS-VP16PYL1(2), codon optimized NLS-VP64PYL1, above with and without codon optimization ... total 300 possible combination | null |
| 11: Linker | null | null | null | IRES, P2A, T2A, E2A, F2A | null |
| 12: Gene 3 | null | null | null | similarly for, PhlF-ABI, LmrA-ABI, ABI-PhlF, ABI-LmrA, NLS-PhlF-ABI (2), | null |

TABLE 3-continued

| | | | | | |
|---|---|---|---|---|---|
| | | | | codon optimized NLS-PhlF-ABI, above with and without codon optimization . . . total 120 possible combination | |
| 13: microRNA targeting site at 3'UTR 1 | null, 1x 122a, 1x 199a, 1x 138, 2x 122a, 2x 199a, 2x 138, 3x 122a, 3x 199a, 3x 138, 4x 122a, 4x 199a, 4x 138, 1x 122a_1X199a, 4x122a_4x199a_4x138, . . . total 126 possible combination | null, 1x 21, 2x 21, 3x 21, 4x 21 | null, 1x 21, 2x 21, 3x 21, 4x 21 | null, 1x 122a, 1x 199a, 1x 138, 2x 122a, 2x 199a, 2x 138, 3x 122a, 3x 199a, 3x 138, 4x 122a, 4x 199a, 4x 138, 1x 122a_1X199a, 4x122a_4x199a_4x138 . . . total 126 possible combination | null, 1x 122a, 1x 199a, 1x 138, 2x 122a, 2x 199a, 2x 138, 3x 122a, 3x 199a, 3x 138, 4x 122a, 4x 199a, 4x 138, 1x 122a_1X199a, 4x122a_4x199a_4x138 . . . total 126 possible combination |
| 14: microRNA targeting site at 3'UTR 2 | null | null, 1x FF5, 2x FF5, 3x FF5, 4x FF5, | null, 1x FF5, 2x FF5, 3x FF5, 4x FF5 | null | null (5), 1xFF3, 2xFF3 (4), 3xFF3, 4xFF3 (3), 1xFF3_off target, 2xFF3_off target (2), 3xFF3_off target, 4xFF3_off target |
| 15: microRNA | null | null, miR-FF3 | null, miR-FF3 | null, miR-FF5 | null |
| 16: polyA signal | TK, rb_glob, SV40, hGH, up, Synthetic | TK, rb_glob, SV40, hGH, up, bGH, Synthetic, | null, TK, rb_glob, SV40, hGH, up, bGH, Synthetic | null, TK, rb_glob, SV40, hGH, up, bGH, Synthetic | TK, rb_glob, SV40, hGH, up, bGH, Synthetic |

| | Genetic Circuits | |
|---|---|---|
| Genetic Elements | Regulatory circuit | Control circuit |
| 1: Insulator | null, cHS4x2, A2, E1, E4, F1, D1 | null, cHS4x2, A2, E1, E4, F1, D1 |
| 2: Enhancer | null, 1xPhlF, 2xPhlF, 3xPhlF, 4xPhlF, 5xPhlF, 6xPhlF, 7xPhlF, 8xPhlF, 9xPhlF, 10xPhlF, 1xLmrA, 2xLmrA, 3xLmrA, 4xLmrA, 5xLmrA, 6xLmrA, 7xLmrA, 8xLmrA, 9xLmrA, 10xLmrA | CMV SV40 hEF1a |
| 3: Operator | null, 1xBM3R1, 2xBM3R1, 3xBM3R2, 4xBM3R2, 1xT14, 2xT14, 3xT14, 4xT14, 1xBM3R1_1xLacO, 1xBM3R1_2xLacO, 1xBM3R1_3xLacO, 1xBM3R1_4xLacO, similarly for 2xBM3R1, 3xBM3R2, 4xBM3R2, 1xT14, 2xT14, 3xT14, 4xT14, . . . total 40 possible combination | null |
| 4: Minimal promoter | null, minCMV1, minCMV2, minCMV3, minCMV4, minCMV5, minCMV6, minKobi, minhEF1a | minCMV1, minCMV2, minCMV3, minCMV4, minCMV5, minCMV6, minKobi, minhEF1a |
| 5: Operator 2 | null, 1xBM3R1, 2xBM3R1, 3xBM3R2, 4xBM3R2, 1xBM3R1_2xKT, 2xBM3R1_2xKT, 3xBM3R1_2xKT, | null |

TABLE 3-continued

| | Genetic Elements | | |
|---|---|---|---|
| | | 4xBM3R1_2xKT, 1xT14, 2xT14, 3xT14, 4xT14, 1xT14_2xKT, 2xT14_2xKT, 3xT14_2xKT, 4xT14_2xKT, similarly add 1-4xLacO . . . total 65 possible combination | |
| 6: microRNA targeting site at 5'UTR 1 | null, 1x 122a, 1x 199a, 1x 138, 2x 122a, 2x 199a, 2x 138, 3x 122a, 3x 199a, 3x 138, 4x 122a, 4x 199a, 4x 138, 1x 122a 1X199a, 4x122a_4x199a_4x138 . . . total 126 possible combination | null |
| 7: microRNA targeting site at 5'UTR 2 | null | null |
| 8: Gene 1 | null, similarly for, LmrA, PhlF, above with and without codon optimization, LmrA-PEST(2), codon optimized LmrA . . . total 60 possible combination | EBFP2, similarly for, LacI, LacI-W220F, LacI-HDAC4, LacI-W220F-HDAC4, above with and without codon optimization . . . total 120 possible combination |
| 9: Linker | null | null, IRES, GSGSG, P2A, T2A, E2A, F2A |
| 10: Gene 2 | null | null, EBFP2, similarly for, LacI, LacI-W220F, LacI-HDAC4, LacI-W220F-HDAC4, above with and without codon optimization . . . total 120 possible combination |
| 11: Linker | null | null |
| 12: Gene 3 | null | null |
| 13: microRNA targeting site at 3'UTR 1 | null, 1x 122a, 1x 199a, 1x 138, 2x 122a, 2x 199a, 2x 138, 3x 122a, 3x 199a, 3x 138, 4x 122a, 4x 199a, 4x 138, 1x 122a_1X199a, 4x122a_4x199a_4x138 . . . total 126 possible combination | null |
| 14: microRNA targeting site at 3'UTR 2 | null | null |
| 15: microRNA | null | null |
| 16: polyA signal | null, TK, rb_glob, SV40, hGH, up, bGH, Synthetic | TK, rb_glob, SV40, hGH, up, bGH, Synthetic |

* Genetic elements that are preferred (first choices) are bolded. Second, third, fourth, or fifth choices are indicated by the number 2, 3, 4, or 5 in the parentheses after the name of the element.

A large number of variants may be constructed using different genetic elements (e.g., those as provided in Table 3) for each circuit of the cell state classifier described herein. Accordingly, a combinatorial library of genetic circuits may be generated and used in the cell state classifiers. The performance of these genetic circuits and the resulting cell state classifiers vary and may be verified in functional assays (e.g., live cell assays).

The different genetic circuits of the cell state classifier may be included in one or more (e.g., 2, 3, 4, 5, 6, 7, 8, 9, 10, or more) nucleic acid molecules (e.g., vectors) and introduced into a cell. A "nucleic acid" is at least two nucleotides covalently linked together, and in some instances, may contain phosphodiester bonds (e.g., a phosphodiester "backbone"). A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine. Nucleic acids of the present disclosure may be produced using standard molecular biology methods (see, e.g., Green and Sambrook, *Molecular Cloning, A Laboratory Manual,* 2012, Cold Spring Harbor Press).

In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

In some embodiments, different genetic circuits of the cell state classifier are delivered to a cell on one or more (e.g., 2, 3, 4, 5, 6, 7, 8, 9, 10, or more) vectors. A "vector" refers to a nucleic acid (e.g., DNA) used as a vehicle to artificially carry genetic material (e.g., an engineered nucleic acid) into a cell where, for example, it can be replicated and/or expressed. In some embodiments, a vector is an episomal vector (see, e.g., Van Craenenbroeck K. et al. *Eur. J. Biochem.* 267, 5665, 2000, incorporated by reference herein). A non-limiting example of a vector is a plasmid. Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector (e.g., retroviral, adenoviral, adeno-association, helper-dependent adenoviral systems, hybrid adenoviral systems, herpes simplex, pox virus, lentivirus, Epstein-Barr virus). In some embodiments, the viral vector is derived from an adeno-associated virus (AAV). In some embodiments, the viral vector is derived from an herpes simplex virus (HSV).

The nucleic acids or vectors containing the genetic circuits of the cell state classifier may be delivered to a cell by any methods known in the art for delivering nucleic acids. For example, for delivering nucleic acids to a prokaryotic cell, the methods include, without limitation, transformation, transduction, conjugation, and electroporation. For delivering nucleic acids to a eukaryotic cell, methods include, without limitation, transfection, electroporation, and using viral vectors.

Cells containing the cell state classifiers are also provided herein. A "cell" is the basic structural and functional unit of all known independently living organisms. It is the smallest unit of life that is classified as a living thing. Some organisms, such as most bacteria, are unicellular (consist of a single cell). Other organisms, such as humans, are multicellular.

In some embodiments, a cell for use in accordance with the present disclosure is a prokaryotic cell, which may comprise a cell envelope and a cytoplasmic region that contains the cell genome (DNA) and ribosomes and various sorts of inclusions. In some embodiments, the cell is a bacterial cell. As used herein, the term "bacteria" encompasses all variants of bacteria, for example, prokaryotic organisms and cyanobacteria. Bacteria are small (typical linear dimensions of around 1 micron), non-compartmentalized, with circular DNA and ribosomes of 70S. The term bacteria also includes bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are gram-negative cells, and in some embodiments, the bacterial cells are gram-positive cells. Examples of bacterial cells that may be used in accordance with the invention include, without limitation, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp. In some embodiments, the bacterial cells are from *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides, cyanobacteria, Escherichia coli, Helobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus planta rum, Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes, Streptomyces ghanaenis, Halobacterium* strain GRB, or *Halobaferax* sp. strain Aa2.2.

In some embodiments, a cell for use in accordance with the present disclosure is a eukaryotic cell, which comprises membrane-bound compartments in which specific metabolic activities take place, such as a nucleus. Examples of eukaryotic cells for use in accordance with the invention include, without limitation, mammalian cells, insect cells, yeast cells (e.g., *Saccharomyces cerevisiae*) and plant cells. In some embodiments, the eukaryotic cells are from a vertebrate animal. In some embodiments, the cell is a mammalian cell. In some embodiments, the cell is a human cell. In some embodiments, the cell is from a rodent, such as a mouse or a rat. Examples of vertebrate cells for use in accordance with the present disclosure include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used.

In some embodiments, the cell is a diseased cell. A "diseased cell," as used herein, refers to a cell whose biological functionality is abnormal, compared to a non-diseased (normal) cell. In some embodiments, the diseased cell is a cancer cell.

Functionality of the Cell State Classifier

Some aspects of the present disclosure provide the functionality of the cell state classifiers and methods of using them. In some embodiments, the methods comprising delivering the cell state classifiers described herein into a cell (e.g., by any of the methods described herein and known to one skilled in the art). In some embodiments, the methods comprises maintaining the cell containing the cell state classifiers. In some embodiments, the maintaining is carried out under conditions to allow the cell state classifier to function. In some embodiments, the presence of the cell state classifier in the cell does not change the native microRNA profile of the cell.

Once introduced into a cell that has a detectable microRNA profile, the cell state classifier described herein is able to detect the microRNAs in the cell and produce an output (e.g., a detectable molecule or a therapeutic molecule) accordingly. In some embodiments, no microRNA input is detected. For example, this may occur if none of the microRNAs the cell state classifier is designed to detect (either microRNA-high or microRNA-low) are expressed in the cell (e.g., expression level is not detectable). As such, the first activator is expressed in the absence of microRNA-low inhibition, leading to activation of the first output molecule. Further, in the absence of the microRNA-high, the second activator expresses, activating the expression of the first repressor, which in turn represses the first output molecule. Thus, both an activating signal and a repression signal exist for the first output molecule in this instance. It is to be understood that in such situations, repression dominates, and the first output molecule does not express, despite the presence of the first activator.

In some embodiments, any one of the first set of microRNAs (microRNA-low) expresses (e.g., has a detectable expression level by the cell state classifier), and the first activator in the first sensor circuit (e.g., VP16GAL4 in FIG. 4) does not express because the first set of microRNAs mediate the degradation of the mRNA encoding the first activator (translational control). As such, the first activatable/repressible promoter of the first signal circuit is not activated, leading to no expression of the first output molecule (e.g., nLuc-2A-neongreen in FIG. 1 or neongreen-2A-ABA of FIG. 4). In a cell classifier where a second signal circuit is present, the second output molecule (e.g., mKate2 in FIG. 4) also does not express due the absence of the third activator (e.g., ABA in FIG. 4) that is encoded by the first signal circuit.

Figure 4:
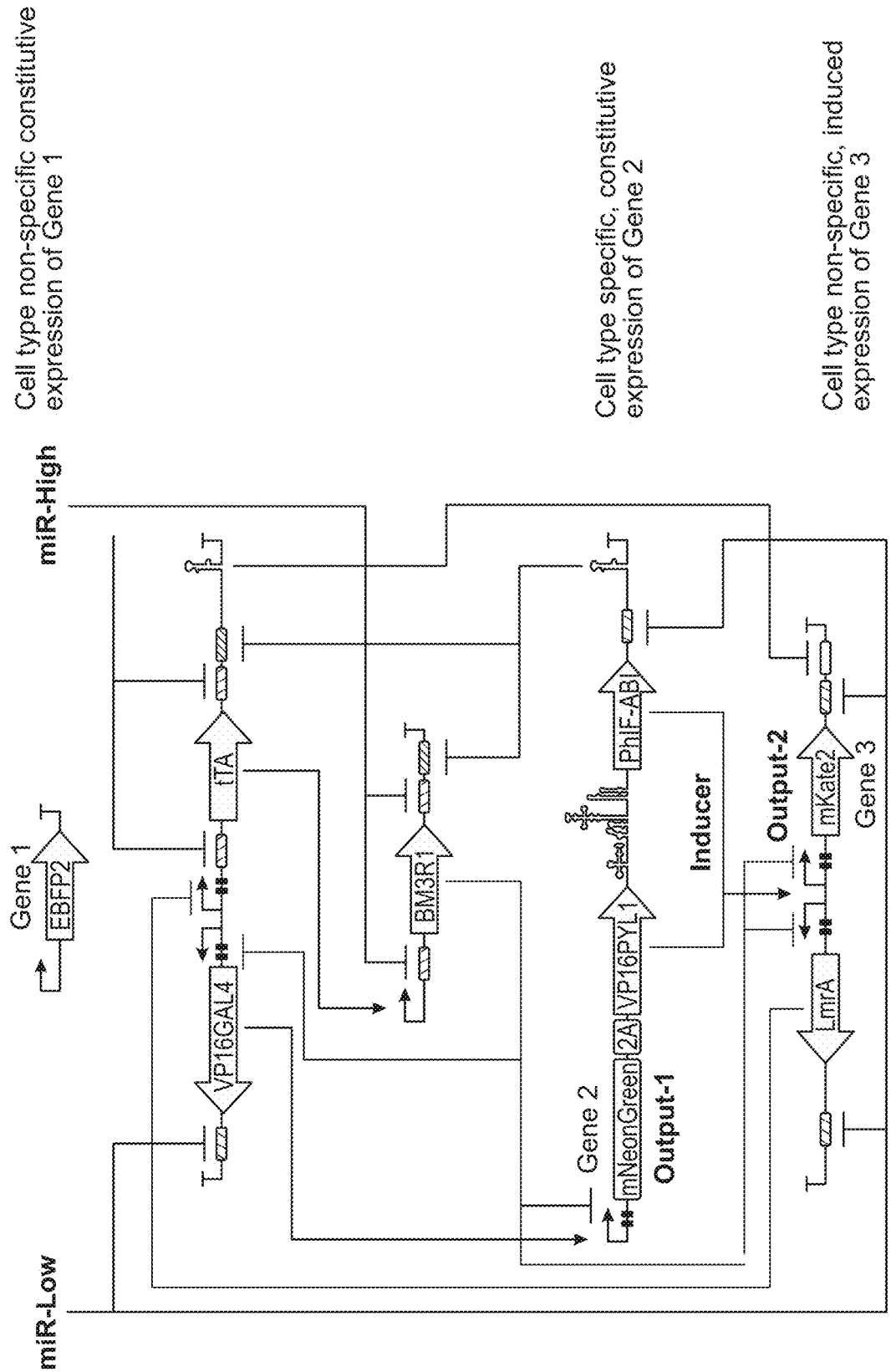
FIG. 4: Diagram of a robust two-step cell classifier. Redundant features increase performance and robustness. Feed-forward and feedback motifs are added to improve the ON or OFF states of Output-1 and Output-2. Expression of Gene 1 is constitutive and not classified. Expression of Gene 2 is classified. Expression of Gene 3 is ABA-inducible and classified. The diagram includes certain specific choices for the transcription factors. Some of the additional features include microRNA target sites in the 5' and 3' for miR-High, BM3R1 repressing expression of Node-A (VP16Gal4), miR-FF3 repressing Output-2, LmrA repressing rTA, miR-Low target site on LmrA and Output-2, and miR-FF5 repressing tTA and BM3R1.
Figure 5:
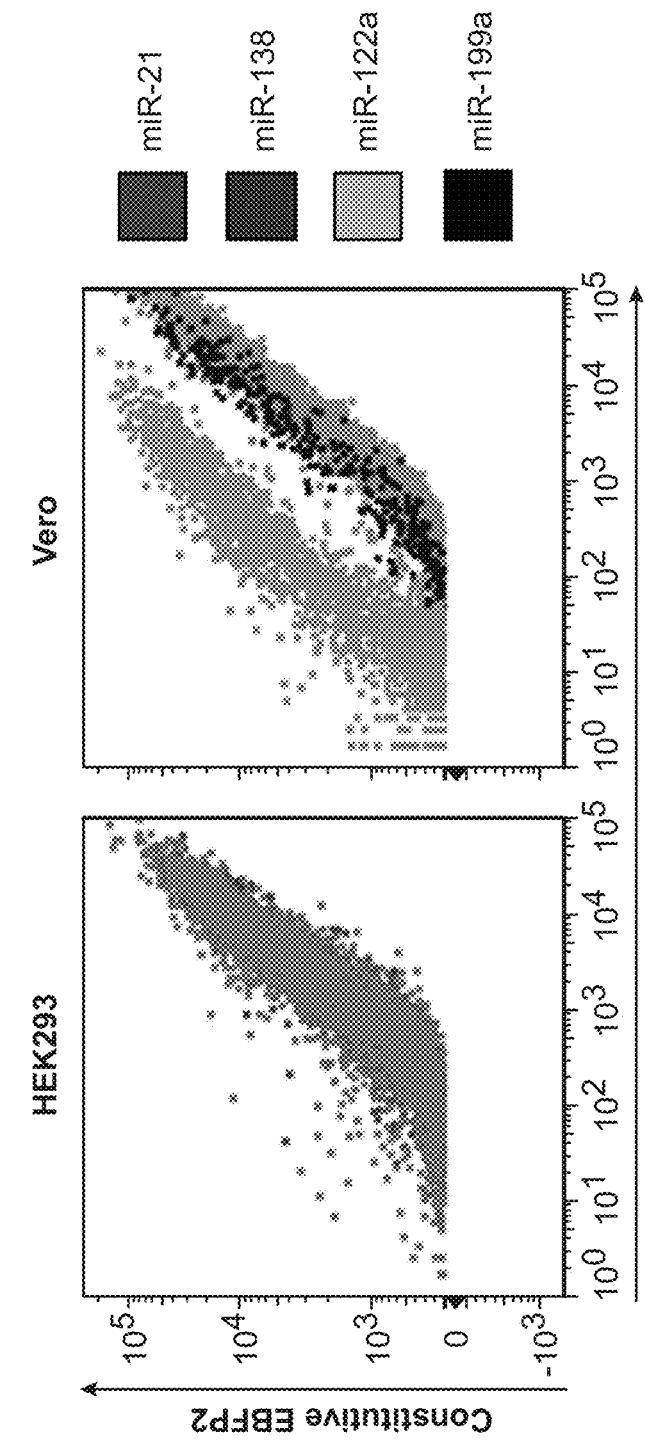
FIG. 5: Selection of miR-Low, miR-High, and cell line assays. As a proof-of-principle demonstration, a four-input cell classifier consisting of one high and three low microRNA sensors was constructed. A set of microRNAs, comprised of miR-21-5p (for use as a miR-High), and miR-199a-5p, miR-122a-5p, and miR-138-5p (for three miR-Lows), were selected, and HEK293 and Vero cells were used to evaluate high sensor performance. Plasmids were constructed with EBFP2 expressed constitutively, while mKate is regulated by the particular microRNA. All four microRNAs appeared to be low in HEK293, while miR-21 appeared high in Vero and miR-199/122a/128 are low in Vero.
Figures 6A, 6B:
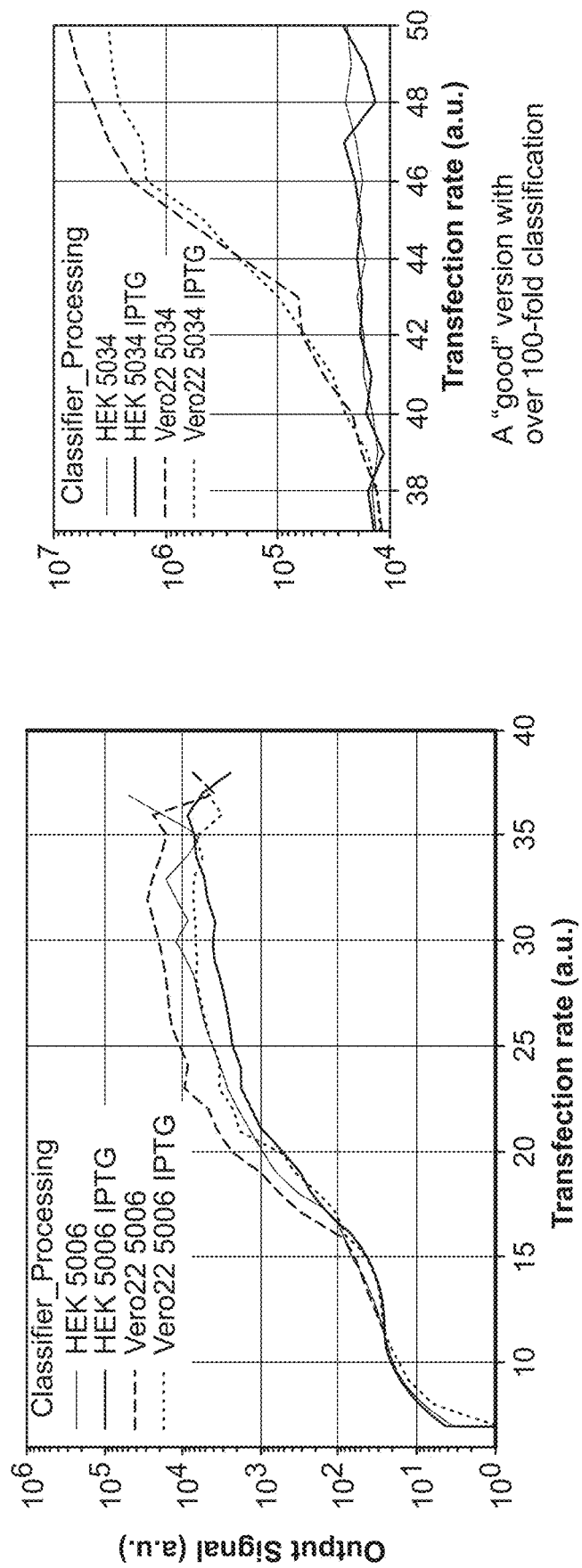
FIGS. 6A-6C: Examples of classifier candidate experimental results (representative of over 200 variants). Circuit variants were characterized by transfecting the circuits as single plasmids into HEK293 and Vero22 cell lines. HEK293 is supposed to have a non-matching microRNA profile, while Vero22 is supposed to have a matching microRNA profile. Fluorescence signals of Output-1 were measured by flow cytometry and were plotted (on the y axis) versus a transfection marker (x axis). In addition, IPTG serves as an inducer to Output-2.
Figure 6C:
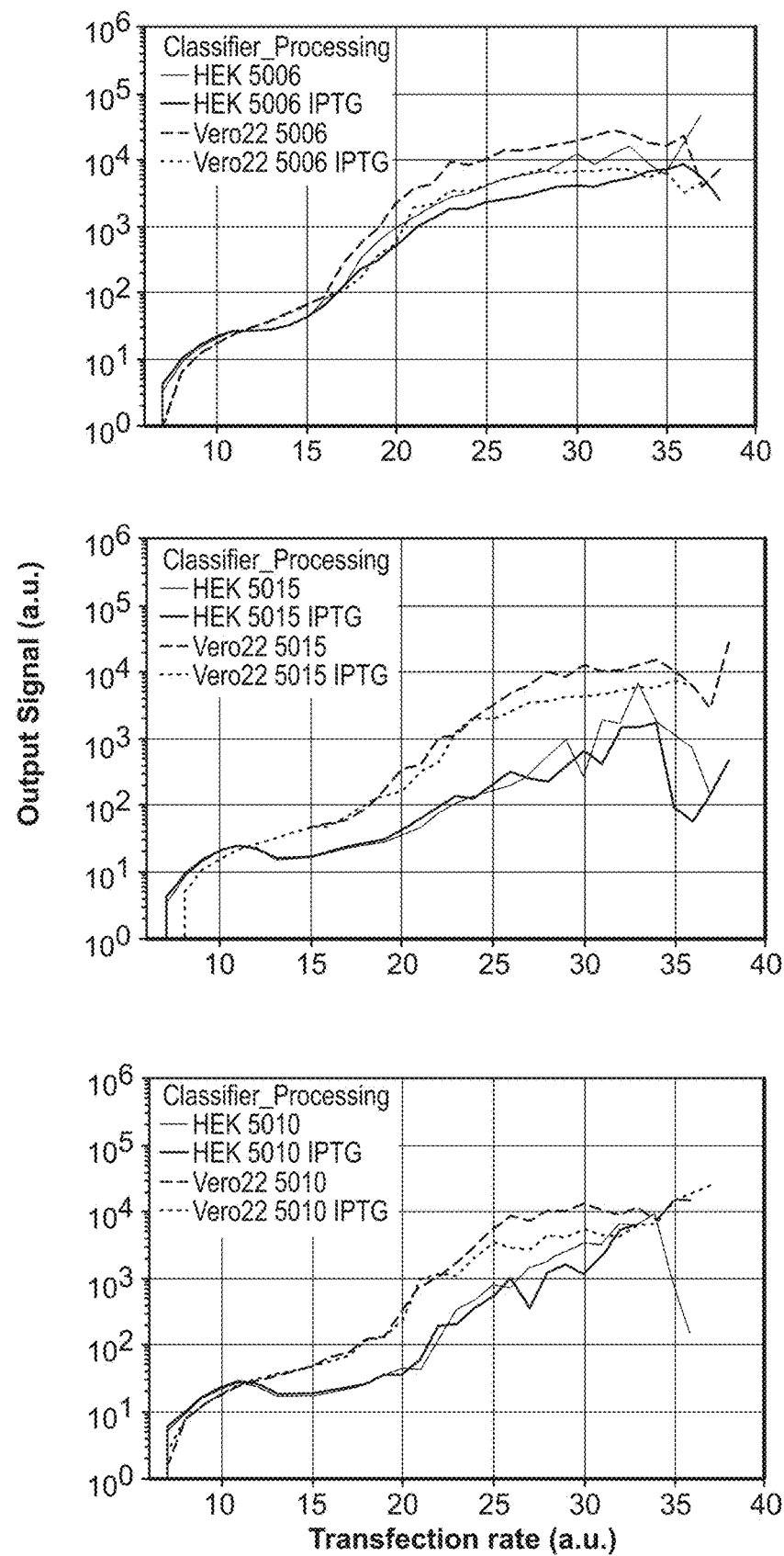
Figure 6C:
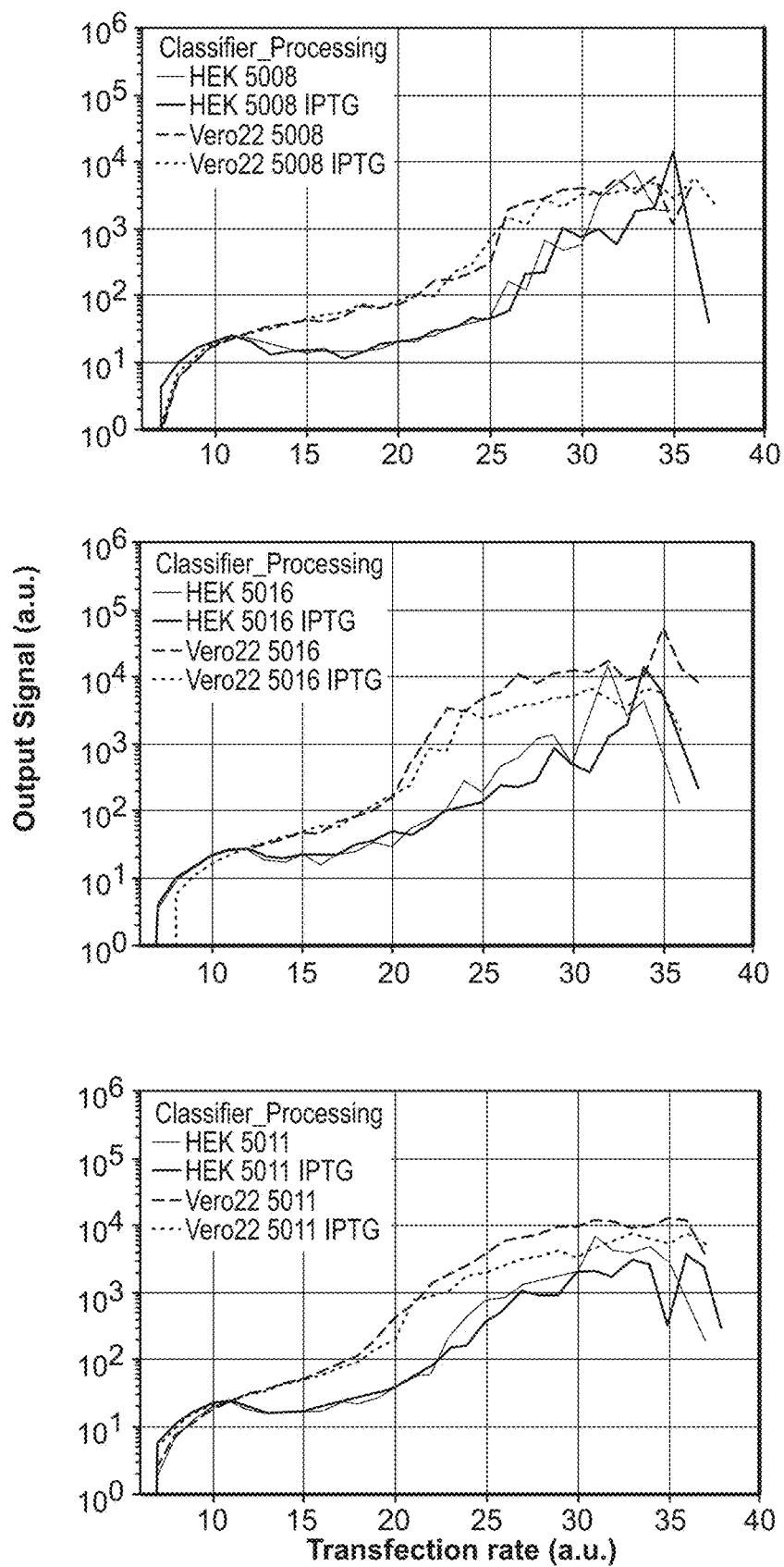
Figure 6C:
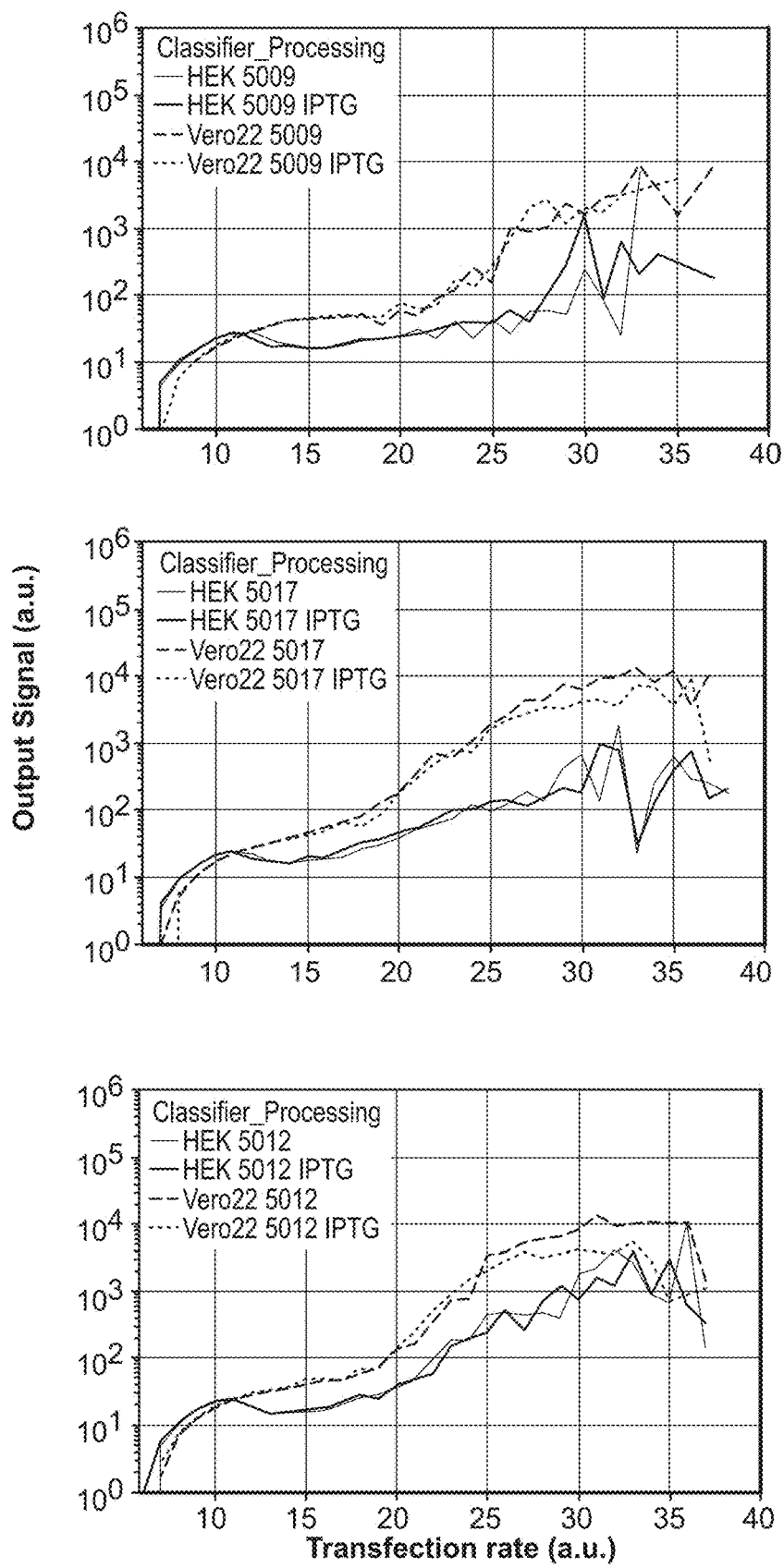
Figure 7A:
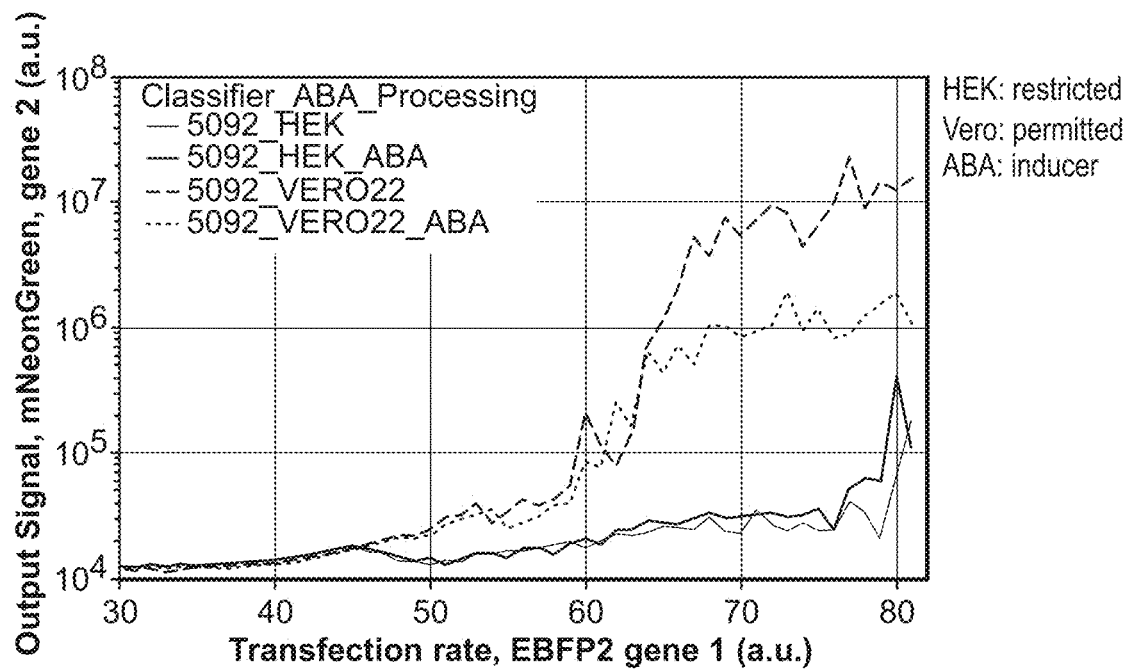
FIGS. 7A-7B: Characterization of the 2-step cell classifier with ABA as inducer.
Figure 7B:
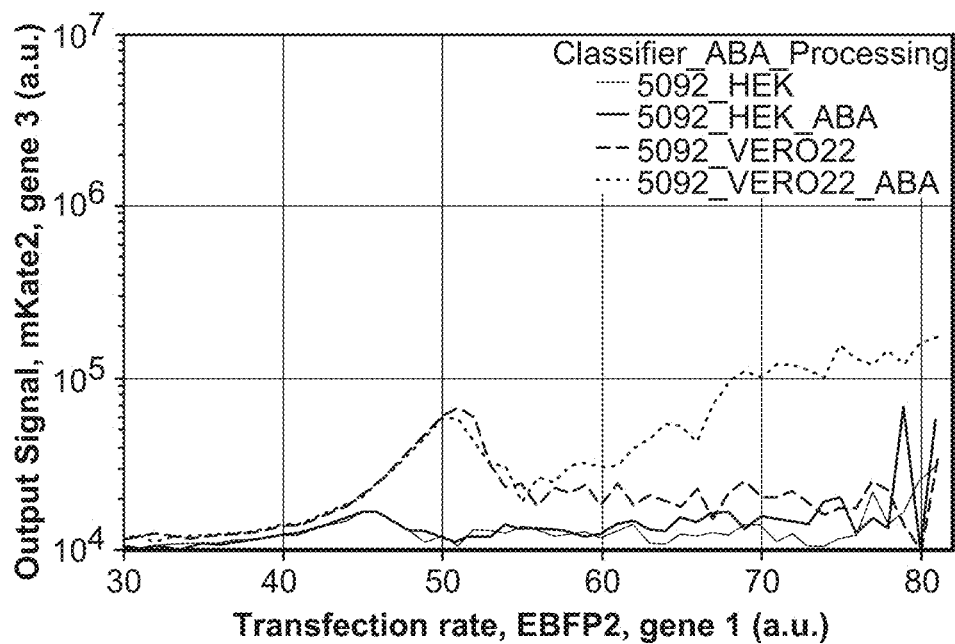

In contrast, in some embodiments, none of the microRNAs in the first set of microRNAs (microRNA-low) expresses (e.g., has a detectable expression level by the cell state classifier), and the first activator in the first sensor circuit (e.g., VP16GAL4 in FIG. 4) is expressed, activating the expression of the first output molecule (e.g., nLuc-2A-neongreen in FIG. 1 or neongreen-2A-ABA of FIG. 4). In a cell state classifier where a second signal circuit is present, the first activator activates the expression of the third activator (e.g., ABA in FIG. 4). When an inducer (e.g., an external inducer such as IPTG) is present, the second output molecule (e.g., mKate2 in FIG. 4) expresses.

In some embodiments, the second microRNA (microRNA-high) does not express (e.g., has a non-detectable expression level by the cell state classifier), and thus the second activator in the first part of the second sensor circuit (e.g., tTA in FIG. 4) expresses and activates the expression of the first repressor in the second part of the second sensor circuit (e.g., BM3R1 in FIG. 4), which in turn represses the expression of the first output molecule (e.g., nLuc-2A-neongreen in FIG. 1 or neongreen-2A-ABA of FIG. 4).

In some embodiments, the second microRNA (microRNA-high) expresses (e.g., has a detectable expression level by the cell state classifier), and thus the second activator in the first part of the second sensor circuit (e.g., tTA in FIG. 4) does not express, because the second microRNA mediates the degradation of the mRNA encoding the second activator (translational control). As a result, the first repressor (e.g., BM3R1 in FIG. 4) does not express in the absence of transcriptional activation by the first activator, and the first output molecule (e.g., nLuc-2A-neongreen in FIG. 1 or neongreen-2A-ABA of FIG. 4) expresses due to the lack of transcriptional repression by the first repressor.

In some embodiments, the cell state classifier detects the expression of the first set of microRNAs (microRNA-low) and the expression of the second set of microRNAs (microRNA-high) (e.g., via microRNA binding sites in the first or second sensor circuits). As such, the cell state classifier also has a logic function, where the cell state classifier produces an output molecule only when a matching microRNA profile is detected (e.g., in a cell, as shown in FIG. 2A). In some embodiments, a matching microRNA profile comprises: (i) none of the first set of microRNAs expresses, or the expression levels of all of the first set of microRNAs (microRNA-low) are low (e.g., undetectable by the cell state classifier); and (ii) the expression level of the second set of microRNAs (microRNA-high) is high (e.g., at least detectable by the cell state classifier), and the output molecule is produced by the cell state classifier. In some embodiments, at least one of the first set of microRNAs (microRNA low) expresses (e.g., expression level is detectable by the cell state classifier) or has high expression level, and the second set of microRNAs (microRNA-high) does not express (e.g., expression level is not detectable by the cell state classifier), and no output molecule or very low output molecule is produced by the cell state classifier. In some embodiments, none of the first set of microRNAs (microRNA low) expresses (e.g., expression level is detectable by the cell state classifier), and the second set of microRNAs (microRNA-high) does not express (e.g., expression level is not detectable by the cell state classifier), and no output molecule or very low output molecule is produced by the cell state classifier. In some embodiments, at least one of the first set of microRNAs (microRNA low) expresses (e.g., expression level is detectable by the cell state classifier) or has high expression level, and the second set of microRNAs expresses or has high expression level, and no output molecule or very low output molecule is produced by the cell state classifier.

In some embodiments, to classify the cell, the method further comprises detecting an output molecule produced by the cell state classifier. For example, the output molecule may be fluorescent protein or an enzyme that acts on a substrate. One skilled in the art is familiar with methods of detecting different detectable molecules. In some embodiments, the cell state classifier comprises a second signal circuit that produces a second output molecule in the presence of an induce. As such, in some embodiments, the method further comprises providing the cell with an inducer (e.g., by supplementing the culturing media with the inducer). In some embodiments, the method further comprises detecting the second output molecule (e.g., a detectable molecule).

In some embodiments, the performance (e.g., specificity, sensitivity, and signal robustness) of the cell state classifier is enhanced (e.g., by at least 10%, at least 20%, at least 30%, at least 40%, at least 50%, at least 60%, at least 70%, at least 80%, at least 90%, at least 100%, 2-fold, 5-fold, 10-fold, 100-fold, or more) by incorporating additional regulatory elements into certain circuits of the cell state classifier. A cell state classifier with improved sensitivity and signal robustness allows detection and reporting out of microRNAs that are naturally low in expression level. A cell state classifier with improved specificity allows accurate classification of a cell and selective production of the output molecule. In the context of therapeutic or diagnostic applications, such cell state classifier are less likely to give false positive or false negative results, and/or are more effective in providing therapy without affecting cells of other types (e.g., healthy cells).

Figure 18A:
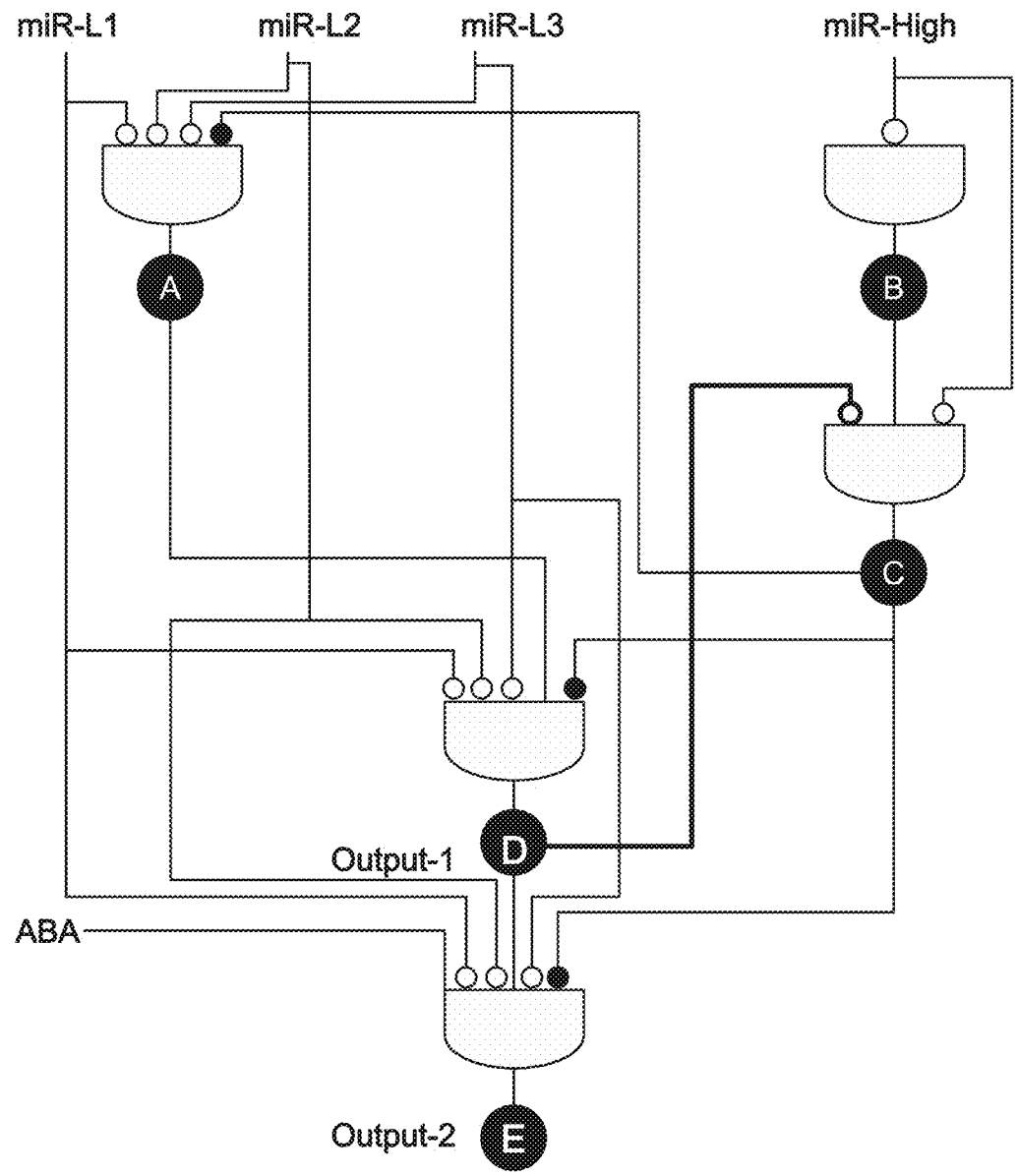
FIGS. 18A-18B: Schematics of Circuit 8.
Figure 18B:
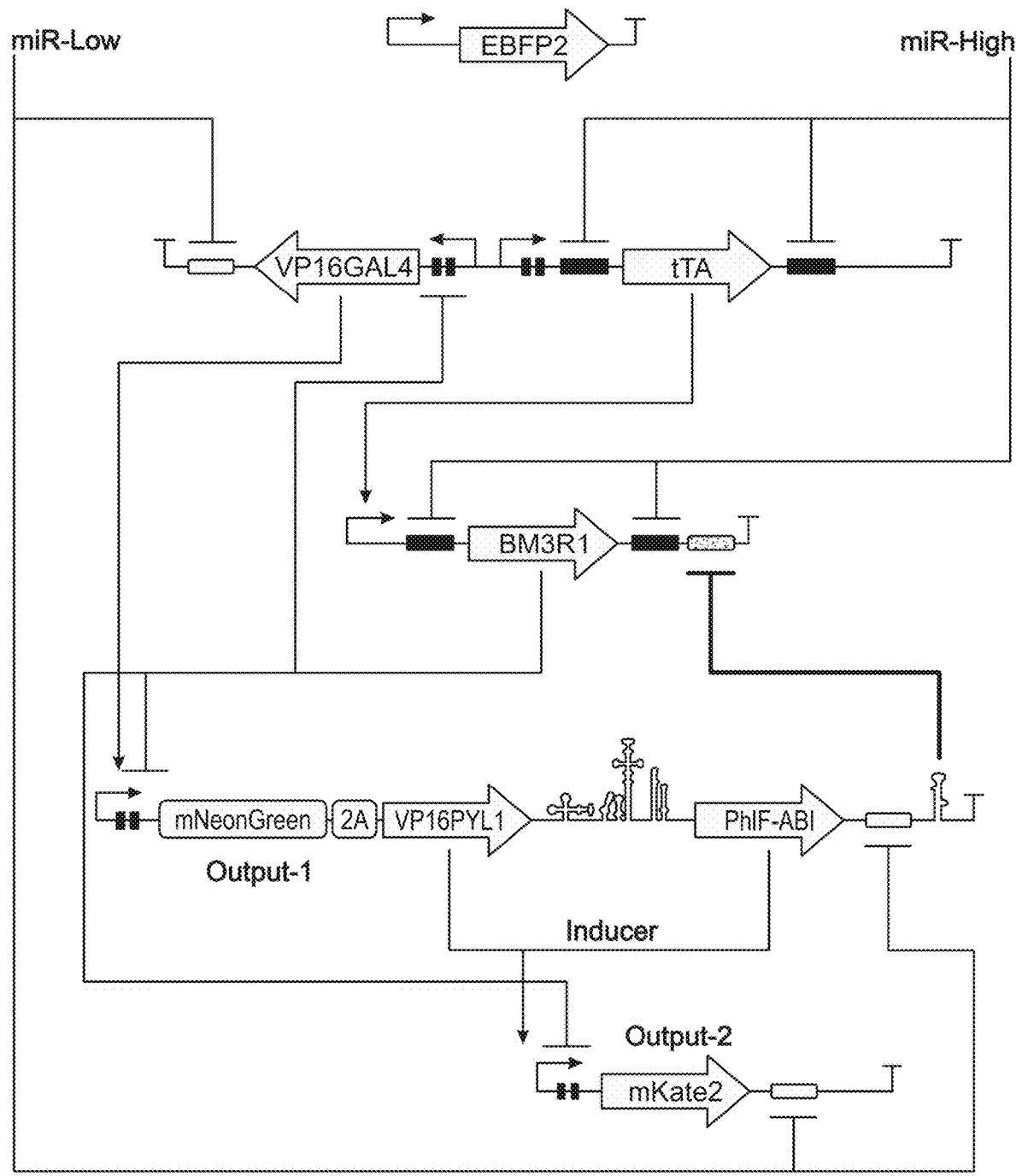
Figure 19A:
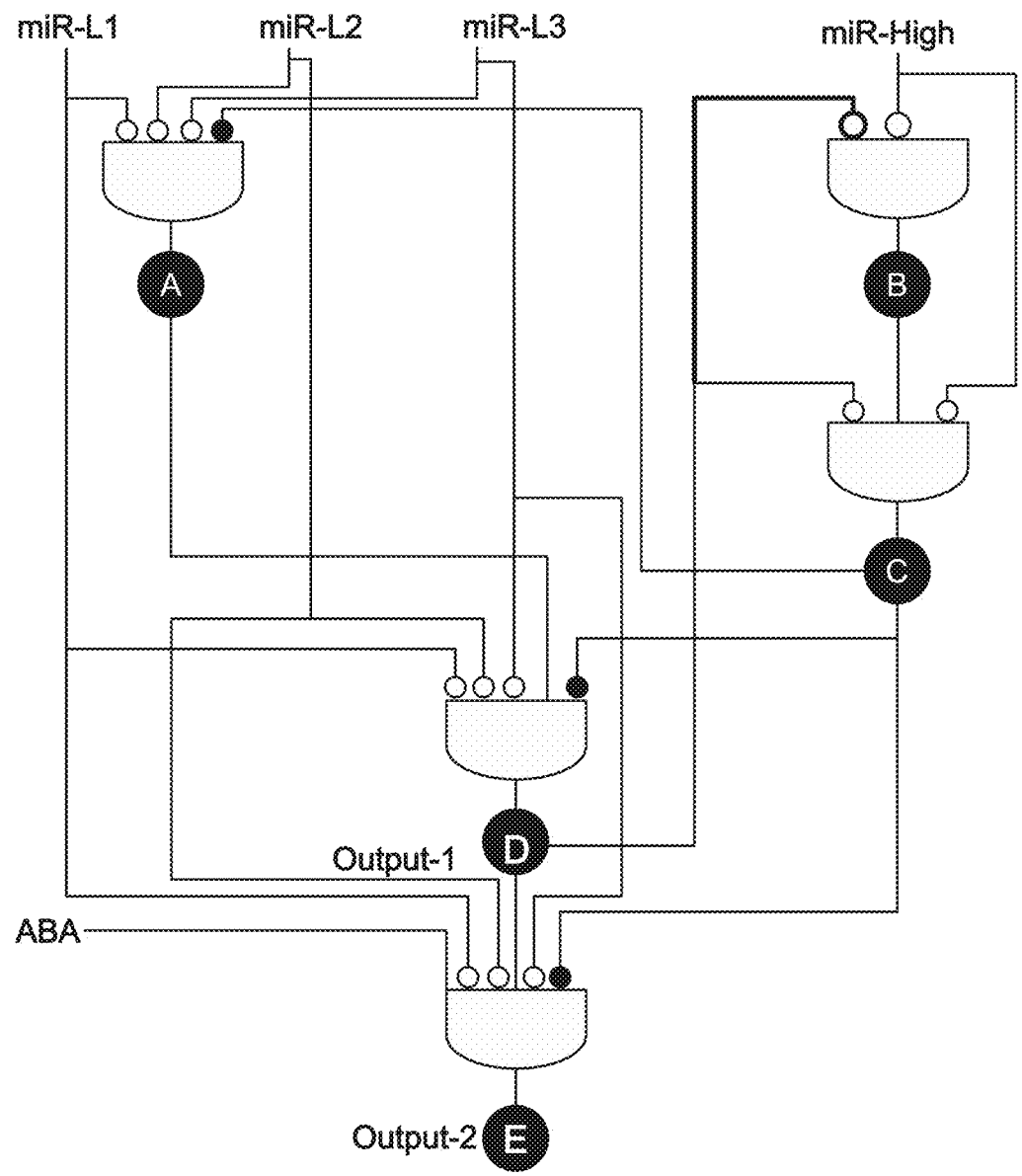
FIGS. 19A-19B: Schematics of Circuit 9.
Figure 19B:
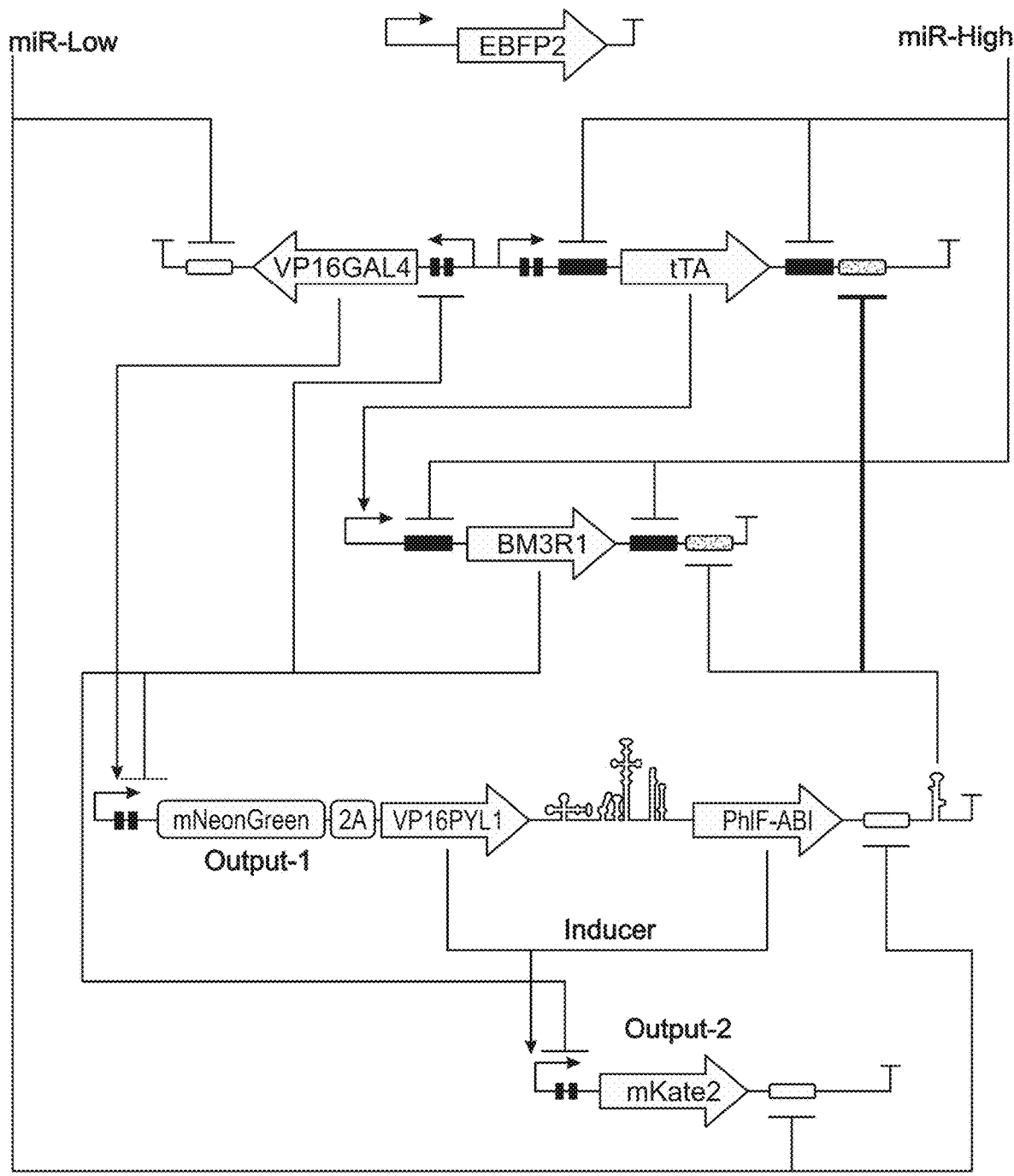

In some embodiments, a feedback loop is incorporated (e.g., as demonstrated in FIGS. 18A and 19A). For example, in some embodiments, a nucleotide sequence encoding a first regulatory microRNA (e.g., mir-FF5 in FIG. 4) may be included in the first signal circuit and the first regulatory microRNA expresses when a matching microRNA profile is detected (e.g., in a cell). Further, target sites for the first regulatory microRNA (e.g., mir-FF5 in FIG. 4) may be inserted into either part of the second sensor circuit. For example, in some embodiments, target sites for the first regulatory microRNA (e.g., mir-FF5 in FIG. 4) are inserted into the first part of the second sensor circuit (e.g., upstream, downstream, or both upstream and downstream) of the nucleotide sequence encoding the second activator. As such, the expression of the first regulatory microRNA, upon detection of a correct microRNA profile, mediates the degradation of the mRNA encoding the second activator, leading to no or reduced expression of the second activator. Thus, the first repressor does not express in the absence of the second activator, which in turn leads to increased expression of the first output molecule. In some embodiments, target sites for the first regulatory microRNA (e.g., mir-FF5 in FIG. 4) are inserted into the second part of the second sensor circuit (e.g., upstream, downstream, or both upstream and downstream) of the nucleotide sequence encoding the first repressor. As such, the expression of the first regulatory microRNA, upon detection of a correct microRNA profile, mediates the degradation of the mRNA encoding the first repressor, leading to no or reduced expression of the first repressor, which in turn leads to increased expression of the first output molecule (i.e., output molecule is amplified, leading to more robust signal and higher sensitivity). Accordingly, in some embodiments, the presence of the first regulatory microRNA (e.g., mir-FF5 in FIG. 4) in the first signal circuit enhances the expression of first output molecule (e.g., by at least 10%, at least 20%, at least 30%, at least 40%, at least 50%, at least 60%, at least 70%, at least 80%, at least 90%, at least 100%, 2-fold, 5-fold, 10-fold, 100-fold, or more), upon detection of a matching microRNA profile. In some embodiments, the cell state classifier with a transcriptional feedback loop described herein has higher sensitivity (e.g., by at least 30%, at least 40%, at least 50%, at least 60%, at least 70%, at least 80%, at least 90%, at least 100%, 2-fold, 5-fold, 10-fold, 100-fold, or more), compared to a cell state classifier without a transcriptional feedback loop. It is noted that the first regulatory microRNA is different from any one of the first set of microRNAs (microRNA-low), and is different from the second microRNA (microRNA-high).

In some embodiments, a feed forward loop is incorporated (e.g., as shown in FIGS. 11A, 13A, 14A, 15A, 16A, 20A, and 22A. In some embodiments, a nucleotide sequence encoding a second regulatory microRNA (e.g., mir-FF3 in FIG. 4) may be incorporated in the second sensor circuit and operably linked to the promoter of the second sensor circuit. As such, the second regulatory microRNA (e.g., mir-FF3 in FIG. 4) expresses when the second microRNA (microRNA-high) does not express (e.g., has an expression level that is not detectable by the cell state classifier). Further, target sites for the second regulatory microRNA (e.g., mir-FF3 in FIG. 4) may be inserted into the second signal circuit (e.g., upstream, downstream, or both upstream and downstream) of the nucleotide sequence encoding the second output molecule. As such, when the second microRNA (microRNA-high) does not express (e.g., has an expression level that is not detectable by the cell state classifier), the second regulatory microRNA (e.g., mir-FF3 in FIG. 4) expresses, in turn mediating the degradation of the mRNA encoding the second output molecule (e.g., mKate2 in FIG. 4), resulting in the reduction of possible background expression (or basal expression) of the second output molecule. In some embodiments, the cell state classifier with a transcriptional feed forward loop described herein has higher specificity (i.e., an output molecule is not produced in the absence of a matching microRNA profile), compared to a cell state classifier without a transcriptional feed forward loop. It is noted that the second regulatory microRNA is different from any one of the first set of microRNAs (microRNA-low), is different from the second microRNA (microRNA-high), and is different from the first regulatory microRNA.

In some embodiments, the second signal circuit further comprises one or more target sites for any one of the first set of microRNAs (microRNA-low). As such, the expression of any one of the first set of microRNAs (microRNA-low) leads to the degradation of the mRNA encoding the second output molecule and represses the expression of the second output molecule (e.g., reducing background or basal expression of the second output molecule and enhance the specificity of the cell state classifier).

In some embodiments, further regulatory control is exerted by the regulatory circuit of the cell state classifier described herein. For example, when any one of the first set of microRNAs (microRNA-low) expresses, the expression of the second repressor is reduced, in turn depressing the promoter in the second part of the second sensor circuit, leading to increased expression of second activator, which in turn reduces the expression of the first and/or second output molecule Conversely, in some embodiments, when the second microRNA (microRNA-high) expresses, the second activatable/repressible promoter of the regulatory circuit is activated by the third activator (in the presence of an inducer). Activation of the second activatable/repressible promoter of the regulatory circuit leads to the expression of the second repressor (e.g., LmrA in FIG. 4), which in turn represses the promoter of the first part of the second sensor circuit, leading to reduced or no expression of the second activator. This mimics the effects of the expression of the second microRNA (microRNA-high), thus enhancing the effects of the expression of the second microRNA (microRNA-high).

In some embodiments, the promoter of the second signal circuit is a second activatable/repressible promoter, which is activated by the third activator in the presence of an inducer and is repressed by the first repressor. Thus, in some embodiments, expression of the second microRNA (microRNA high) leads to the expression of the third activator, activating the second output molecule. In some embodiments, when the second microRNA (microRNA-high) does not express, the first repressor is expressed, repressing the expression of the first output molecule, the second output molecule, as well as the second repressor (e.g., LmrA in FIG. 4).

In some embodiments, the first repressor directly represses the promoter of the first sensor circuit, further enhancing the effects of expression of the second microRNA (microRNA-high) and reducing the effects of the expression of any one of the first set of microRNAs (microRNA-low).

In some embodiments, by placing the target sites for the first or second microRNA (microRNA-low or microRNA-high) in different circuits of the cell state classifier, additional functions of the cell state classifiers can be provided. For example, if the first sensor circuit comprises target sites for the second microRNA (miRNA-high) and the second sensor circuit comprising target sites for the first microRNA (miRNA-low), then the output of the cell state classifier circuit would be reversed such that output would be produced only in cells in which miRNA-low, but not miRNA-high, is expressed.

In some embodiments, the rules stated in the descriptions of FIGS. 11A-11B to FIGS. 22A-22B can be used to design modifications of the cell state classifiers and circuits described herein, such as in methods for producing improved cell state classifiers and circuits. The improvements in cell state classifiers and circuits can be increased performance of the cell state classifiers and circuits, while keeping the same logic of the cell state classifiers and circuits. For example, improvements in performance can be improvements in therapeutic index, specificity, ON/OFF, robustness, resistance to mutation, etc. The rules to be applied include: additions of coherent feed-forward loop(s), replacing endogenous activation with synthetic activation, increasing performance by addition of miRNA repression sites on same target, addition of feedback loop(s), and/or addition of several connections at once to create a new node to replicate or replace some or all of the regulation of another node. Using the rules described herein, one can design and test cell state classifiers and circuits having the same function but having increased performance. In some instances, the higher performance is obtained via additions of redundant functions of the parts of the cell state classifiers and circuits.

Applications

The cell state classifier described herein may be used for a variety of applications. In some embodiments, the cell state classifier may be used for diagnostic purposes. For example, in some embodiments, the cell state classifier may be designed to detect the microRNA profile in a diseased cell (e.g., a cancer cell). As such, if an output signal is detected when such cell state classifier is delivered to a cell, the cell may be classified as a diseased cell (e.g., cancer cell). For diagnostic purposes, the output molecules of the cell state classifier (e.g., the first or second cell state classifier) is typically a detectable molecule (e.g., a fluorescent protein or chemiluminescent protein). In some embodiments, the cell is also provided (e.g., contacted with) with an inducer. In some embodiments, a second output molecule also is detected (e.g., a fluorescent protein or chemiluminescent protein). Depending on the cell type to be detected and the specific microRNA profile, in some embodiments, the expression of the first and/or second output molecule indicates a diseased cell. In some embodiments, the lack of expression of the first and/or second output molecule indicates a diseased cell.

In another example, the cell state classifier is used for therapeutic purposes. For example, in some embodiments, the cell state classifier may be designed to detect the microRNA profile in a diseased cell (e.g., a cancer cell) and to produce an output molecule that is a therapeutic molecule (e.g., a therapeutic protein or RNA). Upon detecting of a matching microRNA profile in the diseased cell, the cell state classifier produces the therapeutic molecule, thus treating the disease. Such therapeutic methods are highly specific to the diseased cell and have low impact on healthy cells because the cell state classifier will not detect a matching microRNA profile in a healthy cell and thus will not produce the output molecule. Further, the therapeutic effect of the cell state classifier is long lasting. For example, the cell state classifier will continuing to produce the therapeutic molecule until the diseased cell no longer has a matching microRNA profile that fit the disease (e.g., cancer). Once therapeutic effects have taken place, the cell state classifier can sense the change in the microRNA profile (e.g., from cancer profile to normal profile) and stop the production of the therapeutic molecule.

For either diagnostic or treatment purposes, the cell may be in vitro (e.g., cultured cell), ex vivo (e.g., isolated from a subject), or in vivo in a subject. For in vivo applications, in some embodiments, the method comprises administering an effective amount of a composition comprising the cell state classifier described herein to a subject in need thereof. The composition can further comprise additional agents (e.g. for specific delivery, increasing half-life, or other therapeutic agents). In some embodiments, the composition further comprises a pharmaceutically acceptable carrier. The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" is a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

Some examples of materials which can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as peptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient," "carrier," "pharmaceutically acceptable carrier" or the like are used interchangeably herein.

An "effective amount" refers to the amount of the cell state classifier or composition comprising such required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a disorder. Alternatively, sustained continuous release formulations of agent may be appropriate. Various formulations and devices for achieving sustained release are known in the art.

An effective amount of the cell state classifier or composition comprising such agents may be administered repeatedly to a subject (e.g., 2, 3, 4, 5, 6, 7, 8, 9, 10 times or more). In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the agents used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the agent (such as the half-life of the agent, and other considerations well known in the art).

For the purpose of the present disclosure, the appropriate dosage of the cell state classifiers compositions as described herein will depend on the specific agent (or compositions thereof) employed, the formulation and route of administration, the type and severity of the disorder, previous therapy, the subject's clinical history and response to the agents, and the discretion of the attending physician. Typically the clinician will administer an agent until a dosage is reached that achieves the desired result. Administration can be continuous or intermittent, depending, for example, upon the recipient's physiological condition, and other factors known to skilled practitioners. The administration of an agent may be essentially continuous over a preselected period of time or may be in a series of spaced dose, e.g., either before, during, or after developing a disorder.

A "subject" refers to human and non-human animals, such as apes, monkeys, horses, cattle, sheep, goats, dogs, cats, rabbits, guinea pigs, rats, and mice. In one embodiment, the subject is human. In some embodiments, the subject is an experimental animal or animal substitute as a disease model. A "subject in need thereof" refers to a subject who has or is at risk of a disease or disorder (e.g., cancer).

The cell state classifiers of the present disclosure may be delivered to a subject (e.g., a mammalian subject, such as a human subject) by any in vivo delivery method known in the art. For example, engineered nucleic acids may be delivered intravenously. In some embodiments, engineered nucleic acids are delivered in a delivery vehicle (e.g., non-liposomal nanoparticle or liposome). In some embodiments, the cell state classifiers are delivered systemically to a subject having a cancer or other disease and produces a therapeutic molecule specifically in cancer cells or diseased cells of the subject. In some embodiments, the cell state classifiers are delivered to a site of the disease or disorder (e.g., site of cancer).

Non-limiting examples of cancers that may be treated using the cell state classifiers and methods described herein include: premalignant neoplasms, malignant tumors, metastases, or any disease or disorder characterized by uncontrolled cell growth such that it would be considered cancerous or precancerous. The cancer may be a primary or metastatic cancer. Cancers include, but are not limited to, ocular cancer, biliary tract cancer, bladder cancer, pleura cancer, stomach cancer, ovary cancer, meninges cancer, kidney cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer. In some embodiments, the tumor is a melanoma, carcinoma, sarcoma, or lymphoma.

EXAMPLES

Described herein are synthetic genetic circuits that determine whether the cell state matches a pre-specified miRNA expression profile (of low and high miRNAs) with high level of precision, which generate transcribed product only if the profile is matched. A large combinatorial library of circuit variants were generated based on new circuit topologies and the best performing candidates were verified using a living cell assay.

The miRNA profile of each cell type serves as an excellent cellular input for a genetic circuit designed to produce outputs only when operating in the cell type of interest. A genetic circuit that performed this operation is termed herein as a "cell state classifier." A typical genetic circuit is composed of multiple transcription units wired together by transcriptional or translational control. In a cell state classifier circuit, the intracellular activity of miRNAs of interest is detected via engineered downregulation of gene expression by these miRNAs. Multiple inputs can be sensed simultaneously by coupling their detection to different portions of the genetic circuit in such a way that circuit output is produced only when the correct input profile of low and high miRNAs is detected.

For the design of a genetic circuit, a detectable output, such as fluorescent or bioluminescent proteins, is employed. In designing the classifier genetic circuit, various transcriptional activator and repressor proteins and other genetic parts (e.g., promoters) that are typically available from a library of variants are selected. Specific choices include the incorporation of nuclear localization signals or degradation tags in proteins, promoters with various operators driving expression of activators or repressors, and a promoter that drives expression of the output. In addition to the large-scale design variations, each design admits many smaller-scale variations such as where and how many miRNA target sites to include.

To test the performance of a classifier circuit, various properties can be measured (e.g., the expressed fluorescence in a range of different cell lines, robustness of the genetic circuit, or selectivity and sensitivity of the circuit). The performance can also be evaluated in different contexts (e.g., in vitro vs. in vivo). The key parameter in evaluating a cell classifier circuit is the ON/OFF ratio and dynamic range (the range of the output fluorescence in the cell of interest vs. other cell lines). A large dynamic range can help minimize false positives (output fluorescence in cells other than permissive cells) and false negatives (lack of output fluorescence in the desired cell type).

Example 1: Cell State Classifiers

A multi-input classifier gene circuit was previously described, which expresses output protein only if the miRNA profile of low and high miRNAs was matched (US Patent Application, US20130202532, incorporated herein by reference). In the new genetic circuit designs described herein, the performance of the genetic circuit was greatly improved. For instance, a greater than 100 fold expression was detected in 4T1 breast cancer cells versus HEK293 negative control cells (robust signal). These improvements enable in vivo applications of the cell state classifiers described herein, including effectively regulating replication of oncolytic viruses.

The new circuit designs are described in progression from simpler to more complex and the performance of the genetic circuit successively improves as additional genetic circuit design features were added. Specific genetic circuit parts were also provided and can be used in the various positions within the overall system design. The specific choices of both topologies and genetic circuit parts determine the performance of the cell state classifier. The combinatorial search space for these variants is tremendous and they cannot be searched at present either experimentally or with existing computational tools.

In all cases, miR-Low inputs are required to be low and miR-High is required to be high in order for the output to be activated. In these examples, multiple miR-Low elements can be connected to the same specified nodes. However, each miR-High input needs to be kept separate. To include additional high miRNAs, the corresponding sensor branch (e.g., Node-B and Node-C in FIG. 1A) needs to be duplicated.

Methods

Parts List

The genetic elements that may be included in each transcriptional unit (circuit) is shown in FIG. 8. The list of options for each genetic element for each circuit are provided in Table 3.

Parts Construction

I. PCR
  Obtaining the source: insulator, promoter, 5' UTR, gene, 3' UTR, polyA were cloned by PCR from genomic DNA, cDNA library, or plasmid DNA.
  Oligo design: DNA oligos containing unique 4 bp overhangs were designed and purchased from Integrated DNA Technology.
  Each basic part for each position is flanked by unique 4 bp overhangs.
  1.25 µL of each oligo (10 µM) was mixed with 0.5 µL of template DNA, 9.5 µL of 2× Q5 High Fidelity Polymerase Master Mix with High GC Buffer, and 12.5 µL of sterile water.
  PCR reaction was run on a thermocycler according to the manufacturer's suggested program.
  PCR product was confirmed by gel electrophoresis.
  A correct sized band was purified by Zymo DNA extraction Kit. The PCR product was eluted with 10 µL of sterile water.
  8.5 µL of the elution was digested by mixing with 1 uL of buffer and 0.5 µL of BsaI and incubating for 15 min.
  The digested product was purified by Zymo PCR clean up kit and eluted with 10 µL of water.
  8 µL of the eluted product was ligated with 0.5 µL of appropriate pre-digested position vector by mixing with 1 µL of buffer and 0.5 µL of T4 ligase.
  Stellar competent cells were transformed by the ligated product, rescued, and then plated on agar plate with 100 µg/mL spectinomycin II. gBlock
  Obtaining the source: when DNA template was not available, DNA sequence was obtained from various sources including literatures or data base.
  gBlock design: DNA gBlock flanked by unique 4 bp overhangs were designed and purchased from Integrated DNA Technology. Each basic part for each position is flanked by unique 4 bp overhangs.

The gBlock was reconstituted with 10 µL of water. 8.5 µL of the reconstituted gBlock was digested by mixing with 1 µL of buffer and 0.5 µL of BsaI and incubating for 15 minutes.

The digested product was purified by Zymo PCR clean up kit and eluted with 10 µL of water. 8 µL of the eluted product was ligated with 0.5 µL of appropriate pre-digested position vector by mixing with 1 uL of buffer and 0.5 µL of T4 ligase.

Stellar competent cells were transformed by the ligated product, rescued, and then plated on agar plate with 100 µg/mL spectinomycin Circuit Assembly Each circuit and the cell state classifier described herein may be assembled using known methods, including, without limitation: TU assembly, Golden gate reaction, or Gibson assembly according to manufacturer's instructions.

For example, for Golden Gate assembly reactions: 0.4 µl of TypeIIS enzyme (either BsaI from NEB, or BpiI from Fermentas), 0.2 µl of T4 Ligase HC+1 µl of T4 Ligase HC buffer (Promega), 1 µl of 10× bovine serum albumin (NEB), 40 fmol for all vectors used in the reaction, ddH20 up to a final total volume of 10 µl. The thermocycler program used for all assemblies included: 1 step of 15 min at 37° C.; then 50 cycles of [2 min at 37° C. followed by 5 min at 16° C.]; 1 step of 15 min at 37° C., 1 step of 5 min at 50° C. and 1 final step of 5 min at 80° C.

For Gibson assembly, the manufacturer's protocol may be found at sgidna.com/documentation/HiFi/Manual-HiFi/GA-_HiFi_Detailed_Manual.pdf Circuit Characterization HEK293FT and HEK293 cell lines were purchased from Invitrogen. HeLa (CCL.2), CHO, COS, hESC cell lines were obtained from ATCC. HEK293FT, HEK293, HeLa and CHO cells were maintained in Dulbecco's modified Eagle's medium (DMEM, Cellgro) supplemented with 10% Fetal Bovine Serum (FBS, PAA), 0.045 g/ml penicillin/streptomycin and non-essential amino acids (HyClone) at 37° C., 100% humidity and 5% CO2. mESC were grown in DMEM supplemented with 15% Fetal Calf Serum (FCS, 10 ng/ml LIF/ESGRO (Millipore), 0.1 mM MEM non-essential amino acids, 100 U/ml penicillin, 100m/ml streptomycin and 100 µM Mercaptoethanol. COS cells were grown in DMEM supplemented with 10% FCS and 0.045 g/ml penicillin/streptomycin. hESC (CHB8, gift of George Daley, Harvard Medical School) were grown on Matrigel-coated plates in mTeSR-1 (Stem Cell Technologies, Vancouver, Canada). HEK293FT and HEK293 transfections were carried out in 24-well plates using Attractene reagent (Qiagen), 200000 cells and 200-300 ng total DNA per well. Media were changed 24 h after transfection. mESC were transfected using Metafectene Pro (Biontex, Germany). Transfection was performed in 6-well plates using 800000 cells and 2 µg of DNA. COS cells were transfected using Metafectene Pro. Transfection was performed in 6-well plates using 600000 cells and 2 µg of DNA. For Hela, CHO, and hESC, 4D Nucleofector (Lonza, Switzerland) were used to electroporate the vectors. For hESC, used 600000 cells, 800 ng total of DNA and the nucleofection program CA-137 (Buffer P2) were used. For CHO, 600000 cells, 600 ng total of DNA and the nucleofection program DT-133 (Buffer SF) were used. For HeLa, 800000 cells, 800 ng total of DNA and the nucleofection program CN-114 (Buffer SE) were used.

Fluorescence microscopy images of live cells were taken in glass-bottom dishes or 12-well plates using Zeiss Axiovert 200 microscope and Plan-Neofluar 10×/0.30 Ph1 objective. The imaging settings for the fluorophores were S430/25x (excitation) and S470/30m (emission) filters for AmCyan, and S565/25x (excitation) and S650/70m (emission) for mKate2. Data collection and processing were performed using AxioVision software (Zeiss). For the circuit library experiment, 500 cells were evaluated from three different fields of views for each replicate transfection (total of 4500 cells examined). All cells were manually marked with a specific tag corresponding to its observed phenotype and used an Adobe Illustrator automated script to sum the number of cell instances for each cell type and each field of view.

Cells were analyzed with LSRFortessa flow cytometer, equipped with 405, 488 and 561 nm lasers (BD Biosciences). About 30000-50000 events were collected using a forward scatter threshold of 5000. Fluorescence data were acquired with the following cytometer settings: 488 nm laser and 530/30 nm bandpass filter for EYFP, 561-nm laser and 610/20 nm filter for mKate2, 405 laser and 525/50 filter for AmCyan and 405 nm laser, 450/50 filter for Pacific Blue. Data analysis was performed with FACSDiva software (BD Biosciences) and FlowJo (flowjo.com). For histogram analysis, flow cytometry data in .FCS format were exported into text format using FCS Extract 1.02 software (E. F. Glynn, Stowers Institute for Medical Research) and analyzed in Microsoft Excel. Bi-exponential scales were used for visualizing fluorescence-activated cell sorting (FACS) data. For cell sorting, cells were collected directly into an 8-well micro-slide (Ibidi) by a FACSAria cell sorter.

Example 2: Improving Circuit Performance and Intermediate Circuit Variants

Figure 23A:
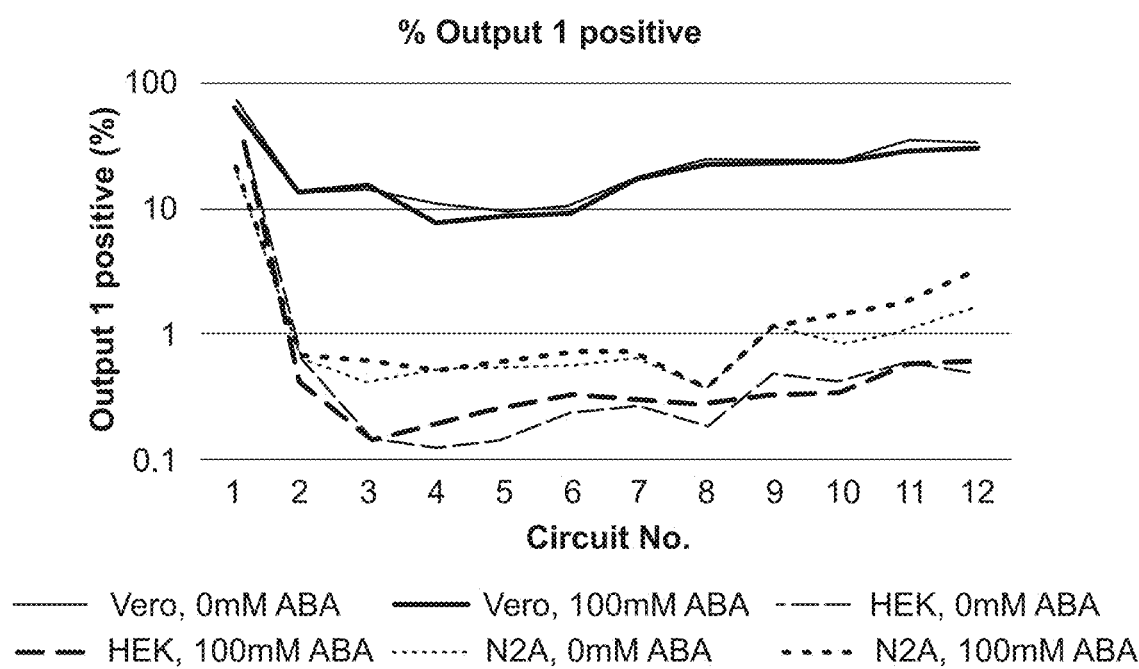
FIGS. 23A-23P: Testing circuit performance. Circuits 13 and 24 are also created by replacing the VP16PYL1 in circuits 1-12 with VP64PYL1. The performance of circuits 1-12 are shown in FIGS. 23A-23D, and 23I-23L. The performance of circuits 11 and 13-24 are shown in FIGS. 23E-23H, and 23M-23P.
Figure 23B:
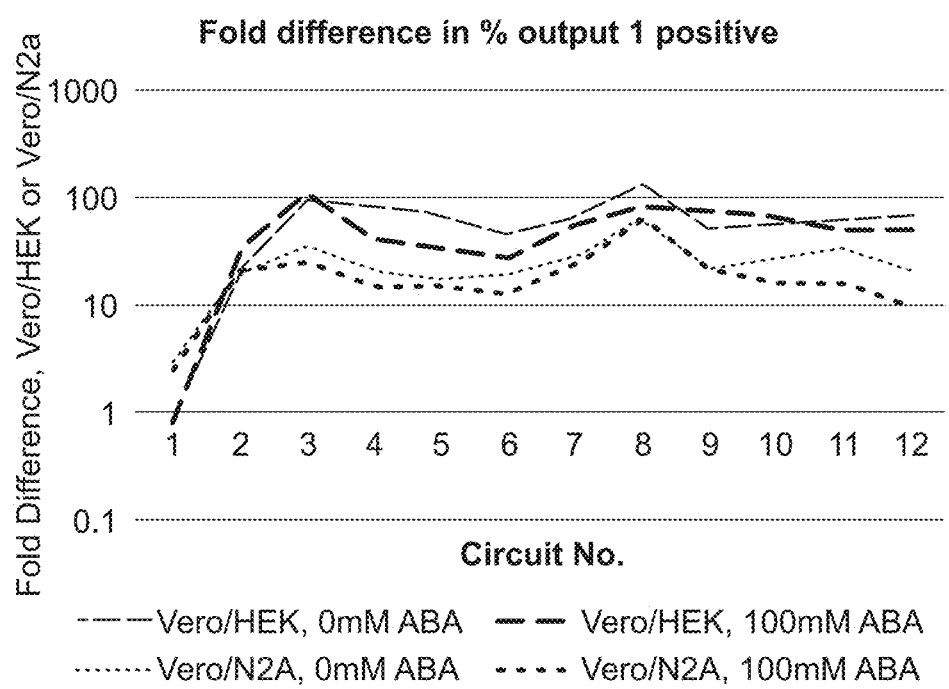
Figure 23C:
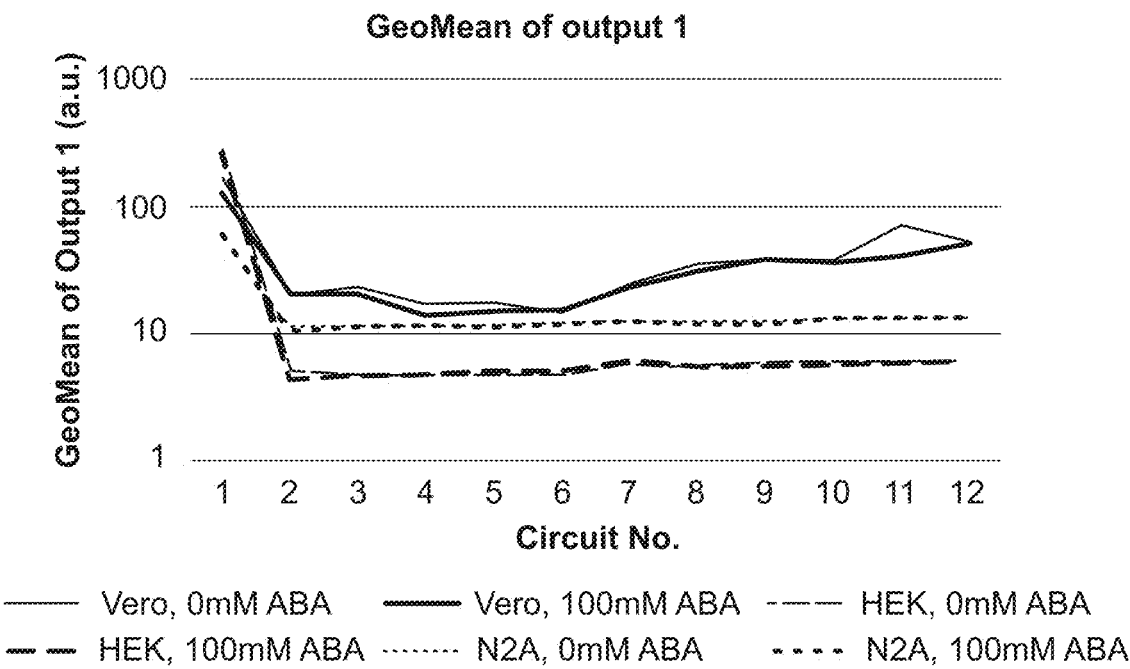
Figure 23D:
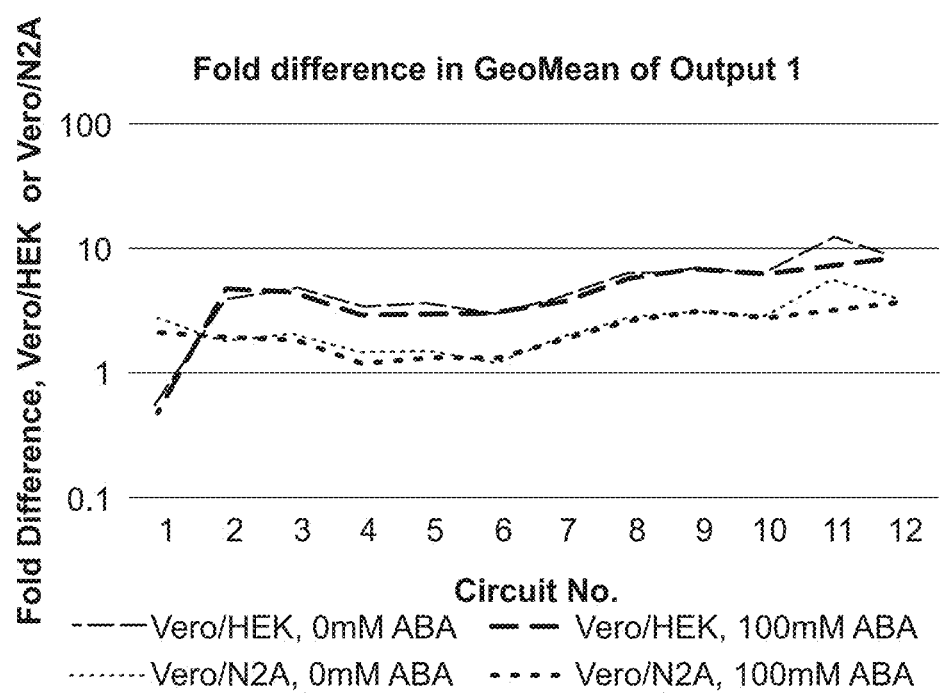
Figure 23E:
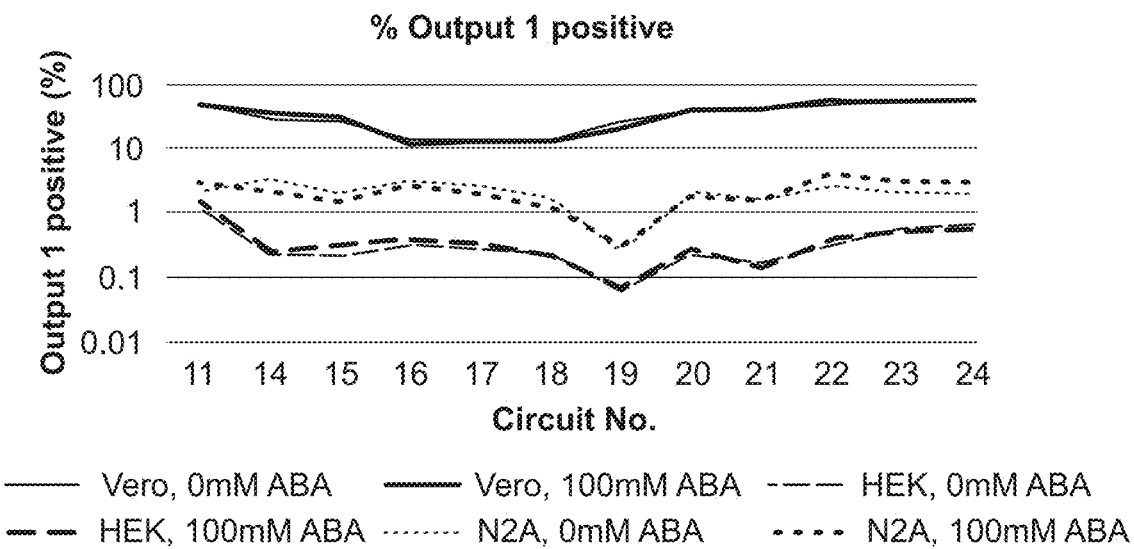
Figure 23F:
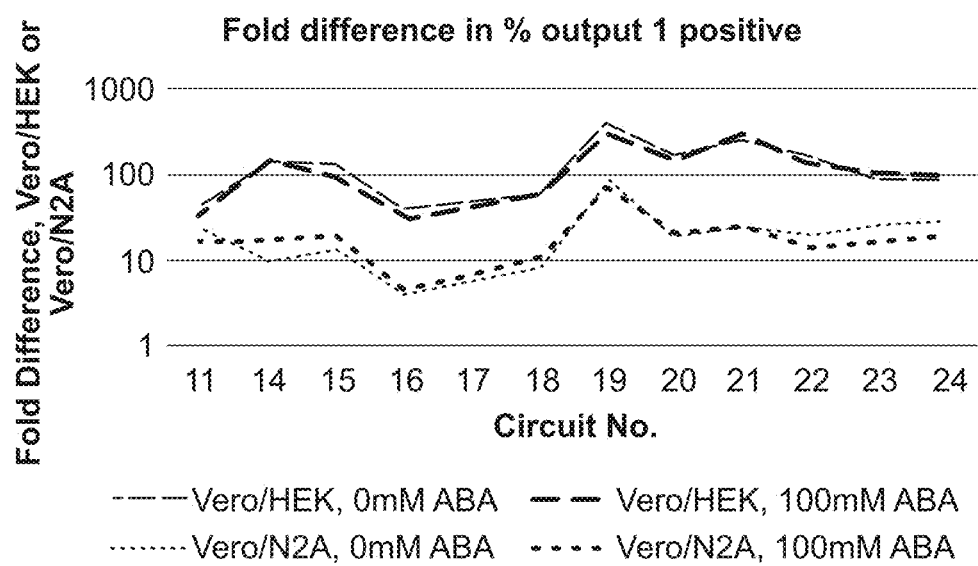
Figure 23G:
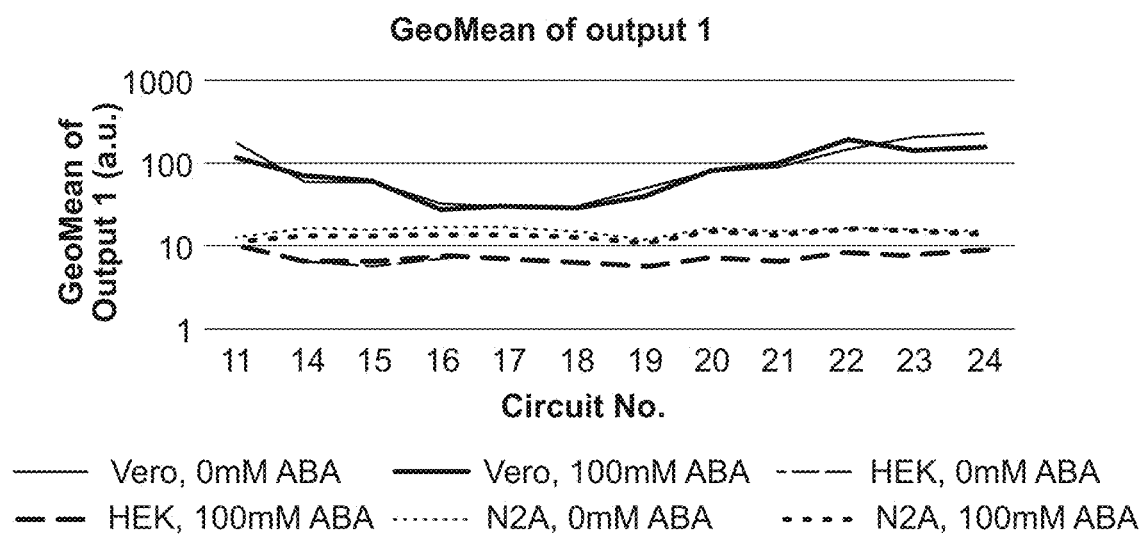
Figure 23H:
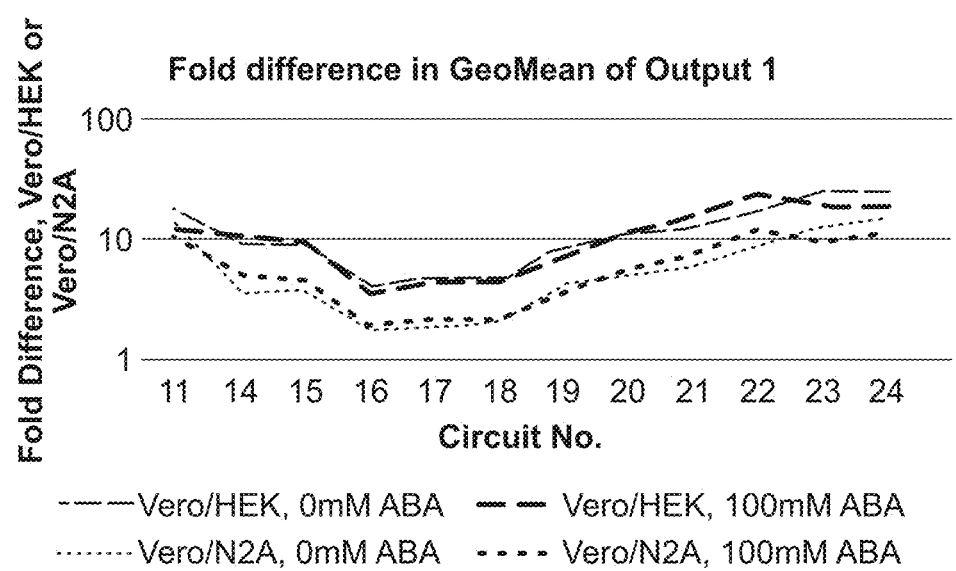
Figure 23I:
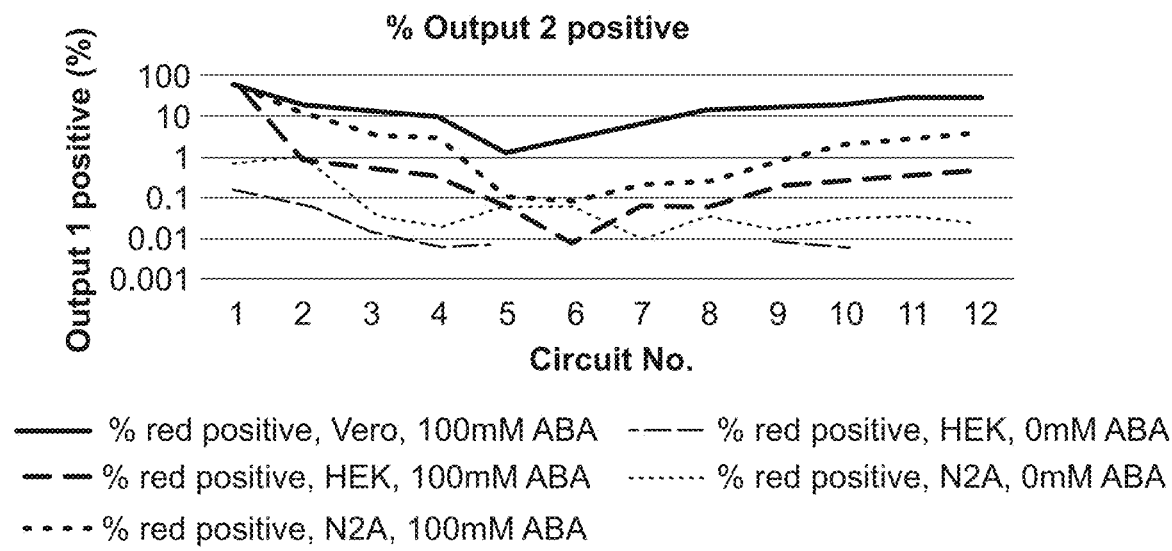
Figure 23J:
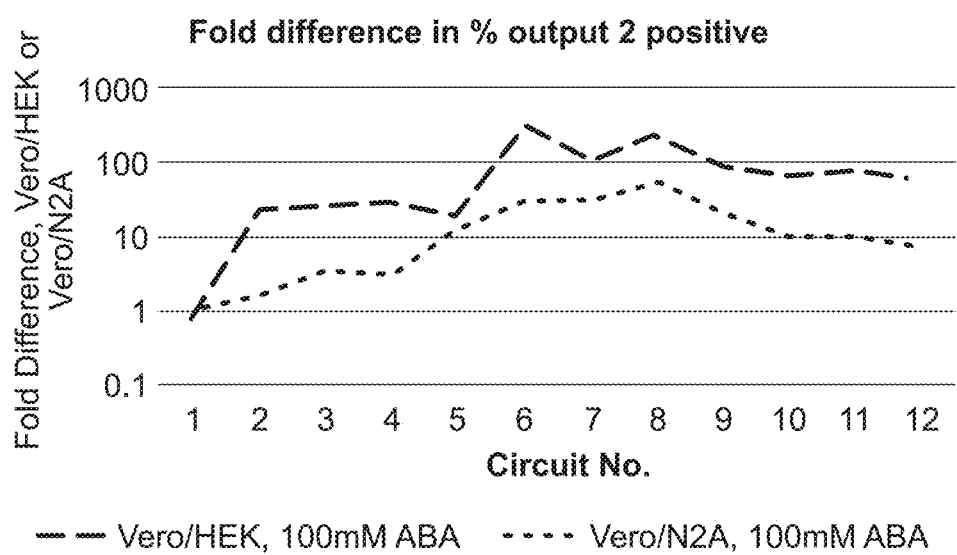
Figure 23K:
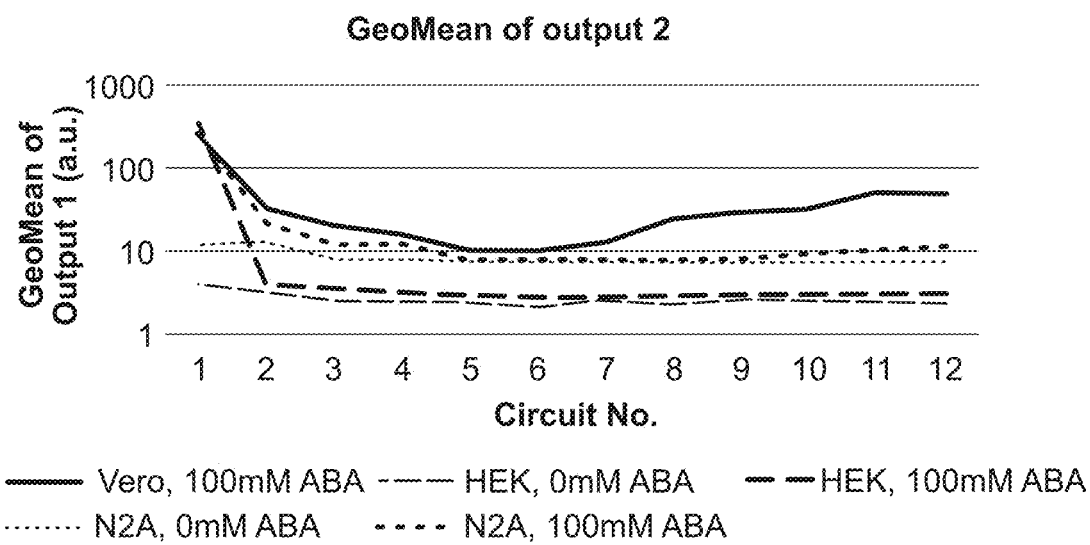
Figure 23L:
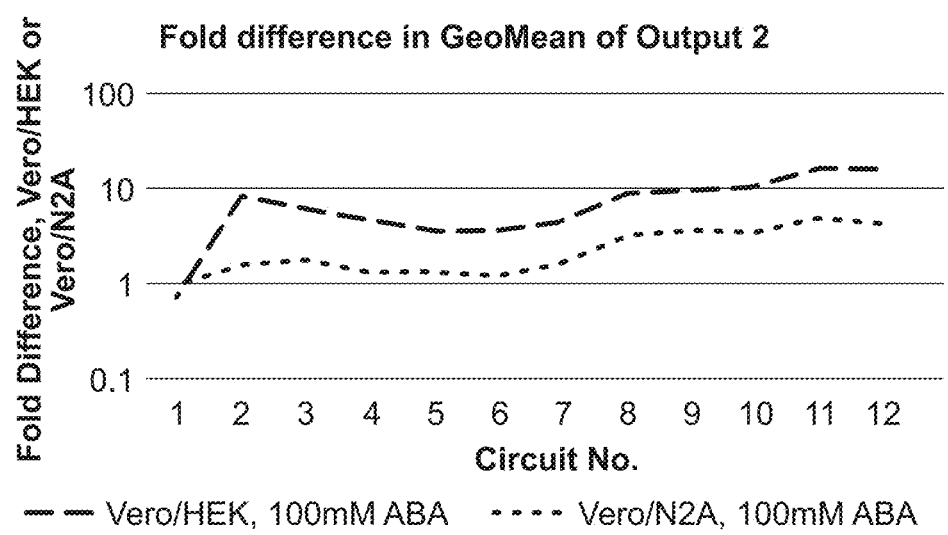
Figure 23M:
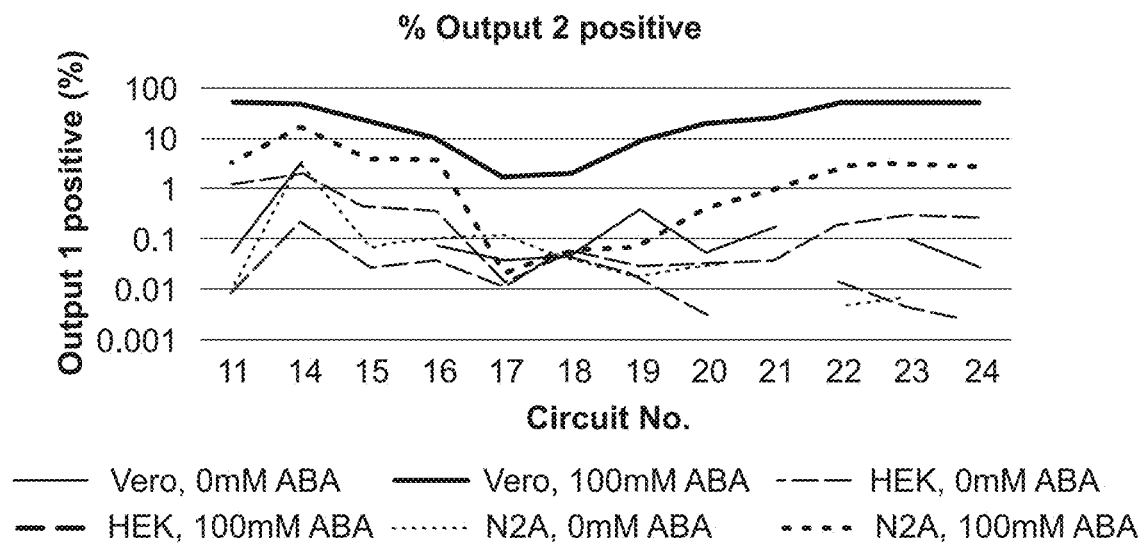
Figure 23N:
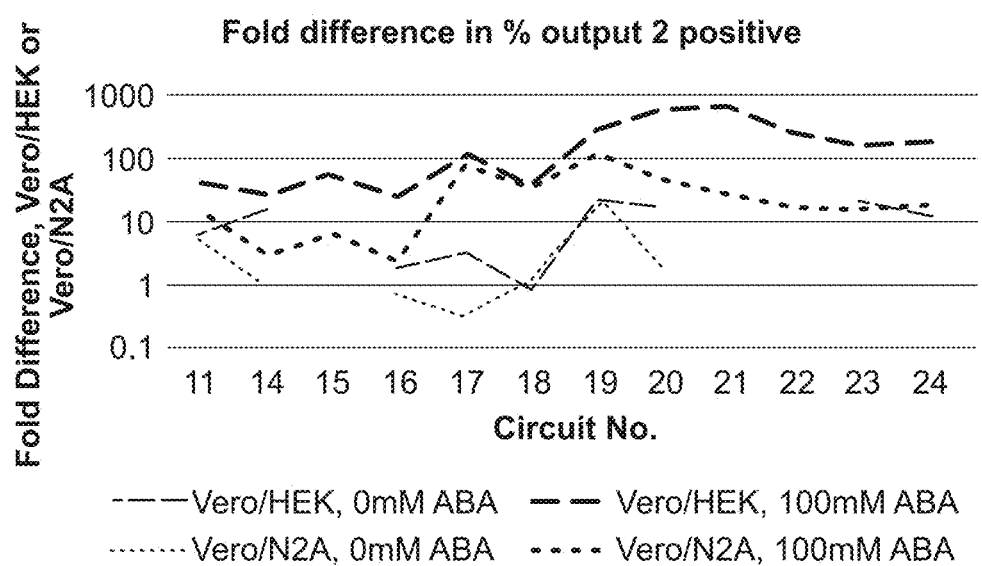
Figure 23O:
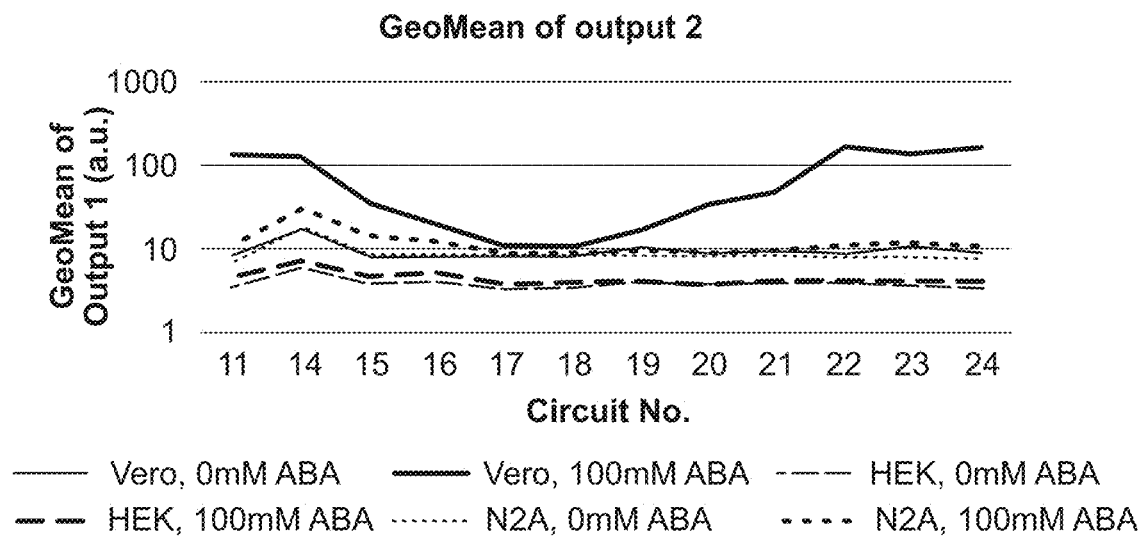
Figure 23P:
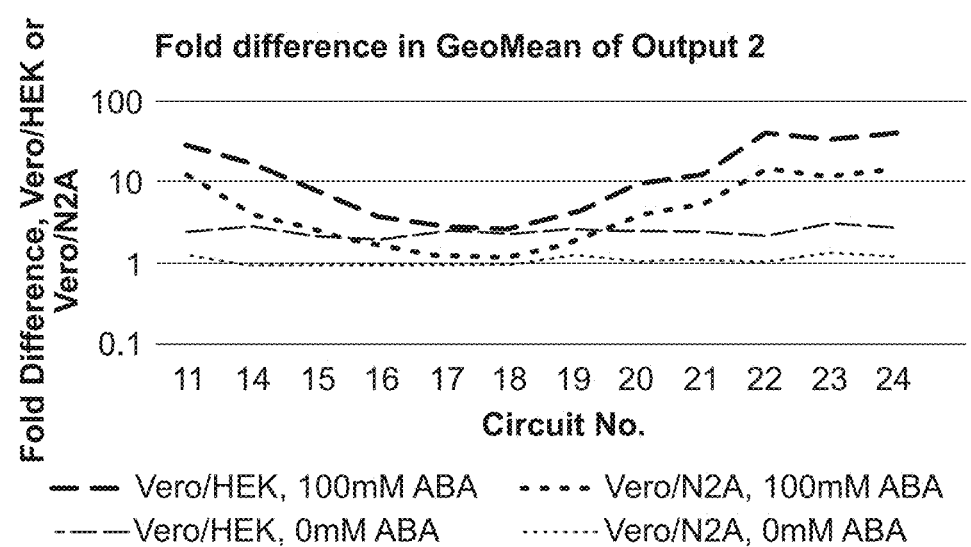

Examples of minimal cell classifier circuits are shown in FIGS. 8 and 9. Schematic and examples of circuit variants with increasing complexity are shown in FIGS. 10A-22B. In the examples of the circuit variants, the protein encoded by the first signal circuit may be VP16PYL1 (Circuits 1-12) or VP64PYL1 (Circuits 13-24). The performance of some circuit variants (circuits 1-12 and circuits and 14-24) are given in FIGS. 23A-23P.

Example 3: Implementations of the Cell State Classifier

Figures 24A, 24B:
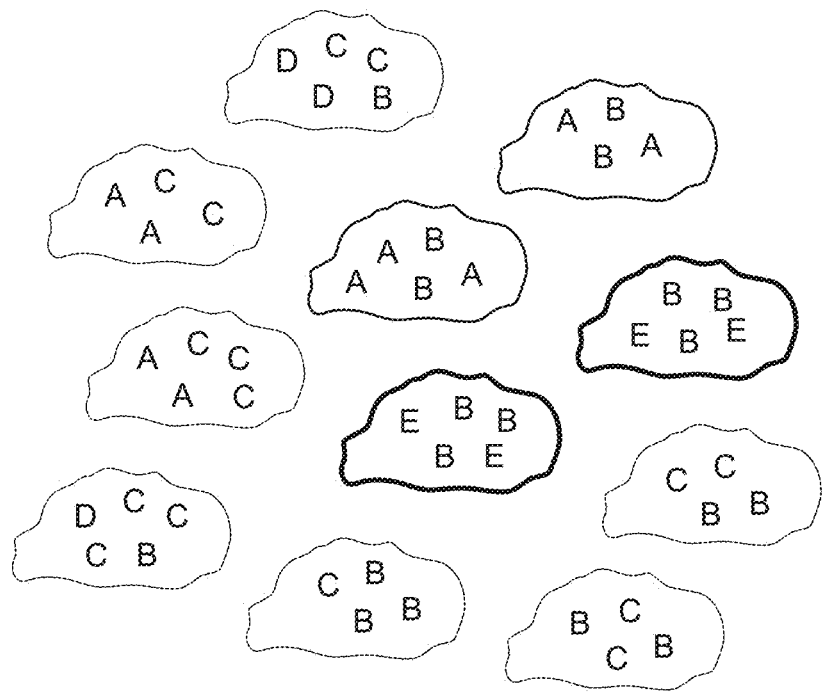
FIGS. 24A-24D: Implementation of the cell state classifiers described herein.
Figure 24C:
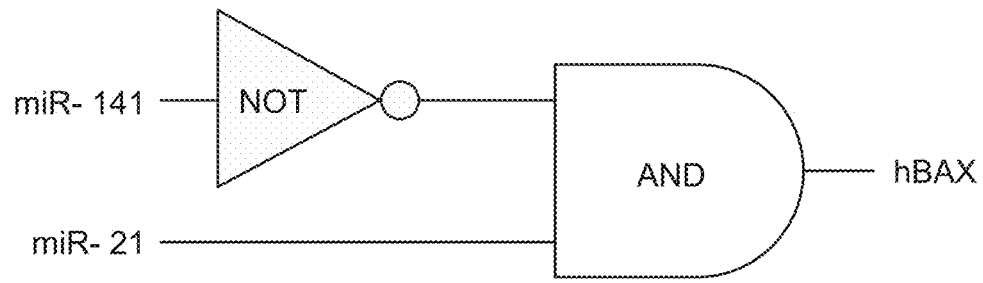
Figure 24D:
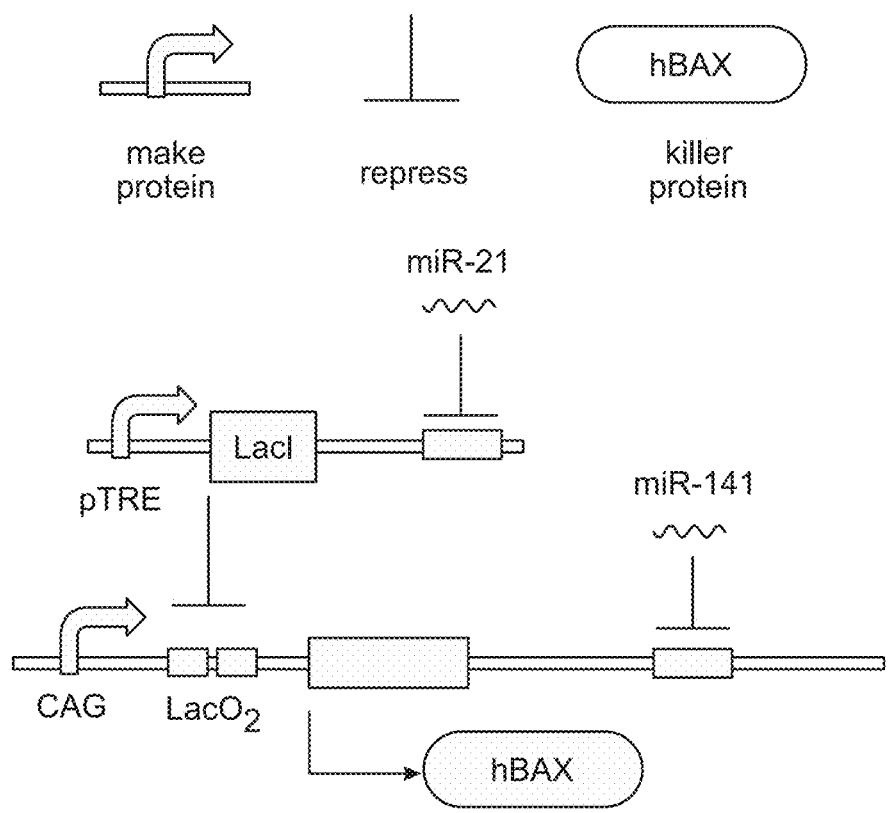

Cell state classification with multiple biomarkers provides one application of the circuits described in example 2. To identify a single cell type from many others, multiple biomarkers (e.g., microRNAs) are sometimes needed as a single biomarker may not be sufficient to identify the single cell type. As shown in FIG. 24A, cancer cell type X express biomarkers "A and B." The cell state classifier can be designed to classify a cell as cancer cell type X if "(A and B) are high" in the said cell. Logic gates (e.g., OR gates) may also be integrated into the cell state classifier. For example, the cell state classifier may be designed such that it classifies a cell as cancer cell type X and X' if "(A & B) are HIGH" OR "(E & B) are HIGH," as shown by Rinaudo, et al., Nat. Biotech, 2007). The circuits described herein can provided a bio-computer to distinguish cancer versus non-cancer cells. A simplified logic truth table illustrates how biomarkers miR141 and miR-21 can be used to distinguish HeLa cancer from all other cells. A cell will be classified as a Hela cell when miR-141 is low AND mir-21 is high (FIGS. 24B-24D)

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A cell state classifier, the cell state classifier comprising:
   (i) a first sensor circuit comprising a promoter operably linked to a nucleotide sequence encoding a first activator and one or more target sites for a first set of microRNAs;
   (ii) a second sensor circuit comprising:
      (a) a promoter operably linked to a nucleotide sequence encoding a second activator, one or more target sites for a second microRNA, and one or more target sites for a first regulatory microRNA that is different from any of the first set of microRNAs or the second microRNA;
      (b) a promoter that is activated by the second activator of (ii)(a), operably linked to a nucleotide sequence encoding a first repressor and one or more target sites for the second microRNA of (ii)(a); wherein the second activator is different from the first activator,
   (iii) a first signal circuit comprising:
      (a) a first activatable/repressible promoter that is activated by the first activator of (i) or repressed by the first repressor of (ii)(b), operably linked to a nucleotide sequence encoding a first output molecule, to a nucleotide sequence encoding a third activator, and to a nucleotide sequence encoding the first regulatory microRNA; and
      (b) one or more target sites for any one of the first set of microRNAs of (i); and
   (iv) a second signal circuit comprising:
      (a) a promoter that is activated by the third activator of (iii)(a) in the presence of an inducer, operably linked to a nucleotide sequence encoding a second output molecule, and
      (b) one or more target sites for a second regulatory microRNA that is different from any of the first set of microRNAs, the second microRNA, or the first regulatory microRNA.

2. The cell state classifier of claim 1, wherein the cell state classifier comprises a plurality of the second sensor circuit of (ii).

3. The cell state classifier of claim 1, wherein (ii)(b) of the second sensor circuit further comprises one or more target sites for the first regulatory microRNA.

4. The cell state classifier of claim 1, wherein (ii)(a) of the second sensor circuit further comprises a nucleotide sequence encoding a second regulatory microRNA operably linked to the promoter of (ii)(a), wherein the second regulatory microRNA is not the same as any of the first set of microRNAs, the second microRNA, or the first regulatory microRNA.

5. The cell state classifier of claim 1, wherein (ii)(a) of the second sensor circuit further comprises multiple target sites for the second microRNA.

6. The cell state classifier of claim 1, wherein (ii)(b) of the second sensor circuit further comprises multiple target sites for the second microRNA upstream of the nucleotide sequence encoding the first repressor.

7. The cell state classifier of claim 1, further comprising a regulatory circuit comprising a second activatable/repressible promoter that is activated by the third activator in the presence of an inducer and repressed by the first repressor, operably linked to a nucleotide encoding a second repressor and one or more target sites for the first set of microRNAs of (i).

8. The cell state classifier of claim 7, wherein the second repressor represses the promoter of (ii)(a).

9. The cell state classifier of claim 1, wherein the second signal circuit further comprises one or more target sites for any one of the first set of microRNAs.

10. The cell state classifier of claim 1, wherein the promoter of the second signal circuit is a second activatable/repressible promoter that is activated by the third activator in the presence of an inducer and repressed by the first repressor.

11. The cell state classifier of claim 1, wherein the first repressor represses the promoter of (i).

12. The cell state classifier of claim 1, further comprising a control circuit that comprises a constitutive promoter operably linked to a nucleotide sequence encoding a control signal that is different from the first output molecule or the second output molecule.

13. The cell state classifier of claim 1, wherein the first sensor circuit, (ii)(a) of the second sensor circuit, (ii)(b) of the second circuit, and/or the first signal circuit further comprises an insulator, an enhancer, one or more operators, a nucleotide sequence encoding one or more output molecules operably linked to the promoter of (i), (ii)(a), (ii)(b), and/or (iii)(a), a nucleotide sequence encoding a microRNA, and/or a polyadenylation signal.

14. A library of cell state classifiers comprising the cell state classifier of claim 1.

15. An isolated cell comprising the cell state classifier of claim 1.

16. A method, the method comprising delivering the cell state classifier of claim 1 to a cell and detecting an output molecule, wherein the cell is ex vivo or in vitro.

17. A method of treating a disease or disorder, the method comprising administering an effective amount of a composition comprising the cell state classifier of claim 1 to a subject in need thereof, wherein the output molecule is a therapeutic molecule that treats the disease or disorder.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
tttgtattca gcccatatcg                                                      20

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
tttaattaaa gacttcaagc g                                                    21

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
taattgtcaa atcagagtgc                                                      20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
tttatgagga atctctttgg                                                      20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ttcgaagtat tccgcgtacg                                                      20

<210> SEQ ID NO 6
<211> LENGTH: 22
<212> TYPE: DNA
```

```
<213> ORGANISM: Artificial Sequence
<220> FEATURE:
<223> OTHER INFORMATION: Synthetic

<400> SEQUENCE: 6
aacgatatgg gctgaataca aa                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
ccgcttgaag tctttaatta aa                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
aagcactctg atttgacaat ta                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
aaccaaagag attcctcata aa                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
cacgtacgcg gaatacttcg aa                                              22
```